United States Patent
Garidel et al.

(10) Patent No.: US 11,572,385 B2
(45) Date of Patent: Feb. 7, 2023

(54) PROCESS FOR THE PREPARATION OF CONCENTRATED LIQUID FORMULATIONS CONTAINING BIOMOLECULES

(71) Applicant: Boehringer Ingelheim International GmbH, Ingelheim am Rhein (DE)

(72) Inventors: Patrick Garidel, Biberach an der Riss (DE); Sven Bahrenburg, Biberach an der Riss (DE); Torsten Schultz-Fademrecht, Aepfingen (DE); Andrea Eiperle, Grodt (DE)

(73) Assignee: Boehringer Ingelheim International GmbH, Ingelheim an Rhein (DE)

( * ) Notice: Subject to any disclaimer, the term of this patent is extended or adjusted under 35 U.S.C. 154(b) by 0 days.

(21) Appl. No.: 16/325,763

(22) PCT Filed: Aug. 11, 2017

(86) PCT No.: PCT/EP2017/070423
§ 371 (c)(1),
(2) Date: Feb. 15, 2019

(87) PCT Pub. No.: WO2018/033482
PCT Pub. Date: Feb. 22, 2018

(65) Prior Publication Data
US 2019/0309016 A1   Oct. 10, 2019

(30) Foreign Application Priority Data
Aug. 17, 2016 (EP) .................................... 16184502

(51) Int. Cl.
*C07K 1/34* (2006.01)
*A61K 9/08* (2006.01)
(Continued)

(52) U.S. Cl.
CPC ................ *C07K 1/34* (2013.01); *A61K 9/08* (2013.01); *A61K 47/02* (2013.01); *A61K 47/12* (2013.01)

(58) Field of Classification Search
None
See application file for complete search history.

(56) References Cited

U.S. PATENT DOCUMENTS 6,712,963 B2 *  3/2004  Schick .............. A61M 1/0209
                                                  210/137
7,740,842 B2 *  6/2010  Arvinte ............ A61K 39/39591
                                                  424/130.1
(Continued)

FOREIGN PATENT DOCUMENTS

EP     0684047 A2    11/1995
EP     1386630 A1     2/2004
(Continued)

OTHER PUBLICATIONS

Pharma Excipients, Excipient Basics, https://www.pharmaexcipients.com/pharmaceutical-excipients-some-definition/, downloaded Jul. 31, 2021. (Year: 2021).*
(Continued)

*Primary Examiner* — Chester T Barry
(74) *Attorney, Agent, or Firm* — Shelley A. Jones

(57) ABSTRACT

It is disclosed an improved multi-step process for the preparation of a highly concentrated liquid formulation containing biomolecules comprising the steps of (a) a first ultrafiltration UF1; (b) a first diafiltration DF1; (c) a second diafiltration DF2; and (d) a second ultrafiltration UF2; wherein an aqueous solution of one or more salts, as liquid medium B, is used for step (b) and water or an aqueous solution of one or more salts, as liquid medium C, is used for step (c), wherein the one or more salts used for step (b) are the same or different from the one or more salts used for step (Continued)

(c) and wherein the liquid medium B has an ionic strength which is higher than the ionic strength of the liquid medium C. The process according to the present invention allows the preparation of well-defined highly concentrated formulations containing biomolecules, particularly proteins, intended for pharmaceutical or non-pharmaceutical use. Unwanted excipient(s) of the starting liquid biomolecule formulation, may be reduced under solution conditions, to very low levels or levels lower than the detection limit.

27 Claims, 11 Drawing Sheets

Specification includes a Sequence Listing.

(51) Int. Cl.
*A61K 47/02* (2006.01)
*A61K 47/12* (2006.01)

(56) References Cited

U.S. PATENT DOCUMENTS

| | | | |
|---|---|---|---|
| 7,823,584 B2 | 11/2010 | Geser et al. | |
| 7,847,072 B2 | 12/2010 | Thorne | |
| 8,387,614 B2 | 3/2013 | Geser et al. | |
| 2002/0044998 A1* | 4/2002 | Wu | A23C 9/1425 426/583 |
| 2007/0062518 A1 | 3/2007 | Geser et al. | |
| 2007/0246406 A1* | 10/2007 | Dibel | B01D 61/16 210/96.2 |
| 2008/0009042 A1* | 1/2008 | Goodey | A61P 17/02 435/71.2 |
| 2009/0098202 A1* | 4/2009 | Friedl | A61K 31/425 424/468 |
| 2011/0011393 A1 | 1/2011 | Geser et al. | |
| 2014/0370003 A1* | 12/2014 | Winter | B01D 61/16 424/133.1 |
| 2020/0291064 A1* | 9/2020 | Becker | C12M 47/10 |

FOREIGN PATENT DOCUMENTS

| | | |
|---|---|---|
| JP | 2009505703 | 2/2009 |
| JP | 201343865 A | 3/2013 |
| WO | 2002096457 | 12/2002 |
| WO | 2005073367 | 8/2005 |
| WO | 2006031560 | 3/2006 |
| WO | 2007022898 A2 | 3/2007 |
| WO | 2009073569 A2 | 6/2009 |
| WO | 2012160047 A2 | 11/2012 |
| WO | 2012160052 A1 | 11/2012 |
| WO | 2012162305 A1 | 11/2012 |
| WO | 2013038170 A2 | 3/2013 |
| WO | 2013093525 A1 | 6/2013 |

OTHER PUBLICATIONS

International Search Report for PCT/EP2017/070423 dated Dec. 4, 2017.
Flickinger, Michael C. "32.7 How Membrane Processes are Operated" (2013) Downstream Industrial Biotechnology, pp. 550-554.
Harinarayan, C. et al. "Small Molecule Clearance in Ultrafiltration/Diafiltration in Relation to Protein Interactions: A Study of Citrate Binding to a Fab" (2008) Biotechnology and Bioengineering, vol. 102, No. 6, 1718-1722.

* cited by examiner

SEQUENCE LISTING

```
<160> NUMBER OF SEQ ID NOS: 5

<210> SEQ ID NO 1
<211> LENGTH: 449
<212> TYPE: PRT
<213> ORGANISM: Artificial Sequence
<220> FEATURE:
<223> OTHER INFORMATION: Description of Artificial Sequence: Synthetic
      monoclonal antibody, heavy chain

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Gln
            20                  25                  30

Thr Ile His Trp Met Arg Gln Ala Pro Gly Gln Gly Leu Glu Trp Ile
        35                  40                  45

Gly Tyr Ile Tyr Pro Arg Asp Asp Ser Pro Lys Tyr Asn Glu Asn Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      monoclonal antibody, light chain

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Lys Ala Ser Arg Asp Val Ala Ile Ala
                20                  25                  30
Val Ala Trp Tyr Gln Gln Lys Pro Gly Lys Val Pro Lys Leu Leu Ile
            35                  40                  45
Tyr Trp Ala Ser Thr Arg His Thr Gly Val Pro Ser Arg Phe Ser Gly
        50                  55                  60
Ser Gly Ser Arg Thr Asp Phe Thr Leu Thr Ile Ser Ser Leu Gln Pro
65                  70                  75                  80
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys Arg Thr Val Ala Ala
                100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 383
<212> TYPE: PRT
<213> ORGANISM: Artificial Sequence
<220> FEATURE:
<223> OTHER INFORMATION: Description of Artificial Sequence: Synthetic
      Fc-fusion protein

<400> SEQUENCE: 3

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255
```

```
Cys Lys Val Ser Asn Lys Ala Leu Pro Ala Pro Ile Glu Lys Thr Ile
        260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
        290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Val Leu Asp Ser
                325                 330                 335

Asp Gly Ser Phe Phe Leu Tyr Ser Lys Leu Thr Val Asp Lys Ser Arg
        340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
        370                 375                 380

<210> SEQ ID NO 4
<211> LENGTH: 451
<212> TYPE: PRT
<213> ORGANISM: Artificial Sequence
<220> FEATURE:
<223> OTHER INFORMATION: Description of Artificial Sequence: Synthetic
      Rituximab HC

<400> SEQUENCE: 4

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 5
<211> LENGTH: 213
<212> TYPE: PRT
<213> ORGANISM: Artificial Sequence
<220> FEATURE:
<223> OTHER INFORMATION: Description of Artificial Sequence: Synthetic
      Rituximab LC

<400> SEQUENCE: 5

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110
```

-continued

```
Ser Val Phe Ile Phe Pro Pro Ser Asp Glu Gln Leu Lys Ser Gly Thr
        115             120                 125

Ala Ser Val Val Cys Leu Leu Asn Asn Phe Tyr Pro Arg Glu Ala Lys
    130             135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
        195                 200                 205

Asn Arg Gly Glu Cys
    210
```

PROCESS FOR THE PREPARATION OF CONCENTRATED LIQUID FORMULATIONS CONTAINING BIOMOLECULES

SEQUENCE LISTING

The present application contains a Sequence Listing which is submitted electronically in ASCII format and is hereby incorporated by reference in its entirety. Said ASCII copy, created on Apr. 24, 2019, is named 01-3195-US-1 SL.txt and is 15,765 bytes in size.

TECHNICAL FIELD

The invention relates to an improved process for the preparation of highly concentrated liquid formulations containing biomolecules.

BACKGROUND OF THE INVENTION

The ability to prepare well-defined biomolecule solutions is an essential aspect during biomolecule-based pharmaceutical formulation development. Biomolecule stability, ionic strength, pH value, and biomolecule concentration as well as biomolecule integrity are among the principal parameters to be controlled.

As a representative of possible biomolecules in particular proteins will be taken into account in the following discussion, particularly the following scientific literature and patent publication.

It is known to improve protein stability by the presence of excipients which somehow interact with protein in solution to stabilize and solubilize it and to avoid the formation of aggregates. In usual protein formulations common excipients used are, for example, salt compounds or other ionic species, sugars, and detergents.

Particularly with regard to pharmaceutical formulations the stability and solubility of the proteins depends on the formulation.

As already known the stability of protein-based pharmaceutical products is a function of solution conditions such as pH value and ionic strength and the kind and concentrations of excipients (Garidel P., Bassarab S. (2008), Impact of formulation design on stability and quality, in: Quality for Biologics: Critical Quality Attributes, Process and Change Control, Production Variation, Characterisation, Impurities and Regulatory Concerns pp. 94-113, Publishing, London, UK). This is true for both liquid and solid (e.g. lyophilized or spray-dried) protein formulations (Schersch K., Betz O., Garidel P., Muehlau S., Bassarab S., Winter G. (2013), Systematic investigation of the effect of lyophilizate collapse on pharmaceutically relevant proteins III: collapse during storage at elevated temperatures, European journal of pharmaceutics and biopharmaceutics: official journal of Arbeitsgemeinschaft für Pharmazeutische Verfahrenstechnik e.V, 85 (2), 240-252).

The interplay between protein and excipients is often very complex, and protein properties and stability usually cannot be predicted (e.g. Hoffmann C., Blume A., Miller I., Garidel P., Insights into protein-polysorbate interactions analysed by means of isothermal titration and differential scanning calorimetry, (2009), European Biophysics Journal, 38 (5), 557-568 Kamerzell T. J., Esfandiary R., Joshi S. B., Middaugh C. R., Volkin D. B. (2011), Protein-excipient interactions: Mechanisms and biophysical characterization applied to protein formulation development, Advanced Drug Delivery Reviews, 63 (13), pp. 1118-1159 and many others more).

Roberts and colleagues, for example, have studied the effects of specific ions (sodium chloride, calcium chloride, sodium sulfate, and sodium thiocyanate) and buffers (acetate, citrate, phosphate, histidine, succinate and tris) on protein-protein interactions in a monoclonal antibody (Roberts D., Keeling R., Tracka M., van der Walle C. F., Uddin S., Warwicker J., Curtis R. (2015), Specific ion and buffer effects on protein-protein interactions of a monoclonal antibody, Molecular Pharmaceutics 2015, 12, 179-193). These interactions affect protein solubility, the formation of protein particles, and overall protein colloidal stability (Garidel P., Blume A., Wagner M., Prediction of colloidal stability of high concentration protein formulations, (2015), Pharmaceutical Development and Technology, 20 (3), pp. 367-374).

In the course of manufacture, a protein solution may have to be modified several times to facilitate unit operations, storage, and/or formulation. Each stage is likely to involve solution exchanges using processes that broadly qualify as filtration-ultrafiltration (UF), size exclusion chromatography (SEC), diafiltration (DF), and counter-current dialysis—alone or in combination. These methods help to condition the protein and alter solution conditions to specified ranges (Janson H.-C. (ed.). (2011), Protein Purification, $3^{rd}$ edition, Wiley, New Jersey).

The most common method for conditioning and preparing of protein solutions, especially on industrial scale, is the combination of ultrafiltration/diafiltration (hereinafter also abbreviated as UF/DF) (see, e.g., Brose D. J., Dosmar M., Jornitz M. W. (2002), Membrane filtration, Pharmaceutical biotechnology, 14, pp. 213-279). In fact, UF/DF is used extensively in downstream processing to concentrate proteins, exchange buffer solutions, condition proteins for such downstream processes as chromatography, and recover the protein in the concentration and buffer solution required for formulation (Marshak D. R., Kadonaga J. T., Burgess R. R., Knuth M. W., Brennman W. A., Lin S.-H. (1996), Protein Purification and Characterisation, Cold Spring Harbor Laboratory Press). Ultrafiltration/diafiltration (UF/DF) is the method usually employed to adjust the pH value, alter the solution's ionic profile/excipient composition, and/or attain target protein concentrations.

UF/DF is usually performed in tangential flow filtration (hereinafter also abbreviated as "TFF") mode, which is also called cross-flow, where feed-solution flow runs parallel to the membrane and thus perpendicular to the filtrate flow. This setup sweeps retained molecules along the membrane surface, out of the membrane chamber, and back to the retentate vessel—offering significantly higher process throughput than dead-end operations (Flickinger, M. C. (ed.) (2013), Downstream industrial biotechnology, John Wiley & Sons, Hoboken Ney Jersey).

TFF often produces concentration polarization, formation of a high concentration gradient and a boundary layer of highly concentrated solutes at the membrane's upstream surface. As a result, protein adsorption, denaturation, aggregation, or precipitation may foul the membrane (Field R. (2010), Fundamentals of fouling, in: Peinemann K.-V., Pereira Nunes S., Membranes for water treatment, Volume 4, Wiley-VCH Verlag GmbH & Co. KGaA, Weinheim, chapter 1, 1-23). Ultimately, the performance of these systems depends almost entirely on the rate at which retained solutes are transported away from the membrane and back into the bulk solution (Bowen W. R., Jenner R. (1995), Theoretical descriptions of membrane filtration of colloids and fine particles: an assessment and review, Adv. Colloid Interface Sci 56, 141-200). This phenomenon is known as concentration polarization.

With reference to FIG. 1A, a schematic representation of a diafiltration (DF) step is illustrated. The diafiltration is a technique that uses permeable or porous membrane filters to remove, replace, or lower the concentration of salts or solvents from solutions containing biomolecules. The process uses the membrane filters to separate the components of solutions and suspensions based on their molecular size. The solution retained by the membrane is known as the concentrate or retentate. The solution that passes through the membrane is known as the filtrate or permeate. In diafiltration, feedstock is repeatedly circulated over the membrane and returned to the retentate vessel, where new liquid medium such as a buffer is added, while permeate removed. As shown in FIG. 1A the diafiltration medium corresponds to the feed medium added to the system, whereas the permeate is the filtration medium removed from the system.

In FIG. 1B a schematic representation of an ultrafiltration (UF) step is illustrated. Ultrafiltration per se follows the same concept and is based on the same schematic setup as shown for the diafiltration in FIG. 1A, but without the addition of new liquid medium.

Ultrafiltration as well as diafiltration processes are widely known and described in prior art:

For example, Marichal-Gallardo P. A., Alvarez M. M. (2012), State-of-the-art in downstream processing of monoclonal antibodies: Process trends in design and validation, Biotechnology Progress, 28, 899-916 and WO 2014/130064 A1 discloses buffer-exchange procedures in which a solution containing the protein of interest is diafiltered against water.

Furthermore, in CA 2 643 508 A1 a process is described for obtaining a human albumin solution, with a high capacity for binding molecules which comprises:
a) a first dialysis (diafiltration);
b) the stabilisation of the solution with NaCl and one or more amino acids, without the addition of fatty acids;
c) heating the solution (pasteurisation); and
d) a second dialysis (diafiltration).

That is, a combination of diafiltration steps, for example, used to detoxify albumin in the blood or plasma of a patient, with the aim to remove substances that are bound to albumin. In between these two diafiltration steps, the albumin is heated, i.e. a step of virus inactivation by pasteurisation is performed, with the albumin stabilised in the presence of at least one amino acid and sodium chloride. This process allows removing compounds bound to the albumin such as lipids, fatty acids, because these compounds reduce the binding capacity of albumin. A heating of the solution between a first and a second diafiltration is not performed in the present invention.

Further, WO 91/00290 A1 relates to a method for purifying a protein from multivalent metal ions bound thereto, these ions being released from the protein by exchanging the ions with monovalent metal ions, whereafter the multivalent metal ions are removed. The release and removal of these ions are effected, in particular by methods of diafiltration or gel filtration. Especially, for cleansing proteins such as albumin and gammaglobulin from multivalent metal ions, e.g. aluminium, iron or lead, which are bound to the proteins, it is used a combination of two gel-filtration steps including water and salt solutions up to 1 M, in order to remove the multivalent metal ions and exchanging them against sodium, potassium or ammonium ions. However, from the analysis of the presented figure related to the description of this process, it is unclear how the gel-filtration process is run. Furthermore, the document describes the cleansing of metal ions, but it is completely silent with regard to organic ions e.g. anions, such as phosphate, succinate, acetate ions, and the conditioning of protein solutions containing such organic ions.

According to WO 2002/051979 A2 it is provided a method to remove citrate, aluminium, multivalent ions and contaminants from proteins by adjusting the pH of a solution containing the protein to a pH from about 7 to about 10, diafiltering the aqueous solution against pure water to thereby provide a filtrate comprising the multivalent ions and a retentate comprising the protein. In one embodiment it is described a very specific way of performing two diafiltration steps in the same vessel (see claim 11). The process parameters used as well as the diafiltration steps combined with ultrafiltration steps and in particular the order of the sequence of the process steps as disclosed in the present invention is not clearly described.

Furthermore, some documents of the prior art are related to a process to concentrate macromolecules:

For example, WO 02/096457 A2 is directed to stable liquid formulations of antibodies suitable for parenteral administration. Also provided are aqueous solutions which have high concentrations of therapeutical antibodies which may be used to produce therapeutical liquid formulations, uses, such as medical uses, of the stable liquid formulations and processes for the production of the stable liquid formulations. A process for the preparation of a therapeutical liquid formulation comprises an antibody at a concentration of more than 50 mg/ml, wherein in a first step an antibody solution in a suitable buffer is concentrated to a concentration in the range from about 10 mg/ml to about 50 mg/ml; in a second step, the concentrated solution obtained in the first step is diafiltered with an aqueous solution of at least one acidic component, optionally containing $MgCl_2$ and/or $CaCl_2$ and/or further suitable additives; and, in a third step, the solution obtained in the second step is further concentrated to a concentration of more than 50 mg/ml. Therefore, the process uses the sequence of a concentration step/a diafiltration step/a concentration step. The concentration step may be performed with an ultrafiltration system. In order to provide less turbid solutions a further 5-step process is described that involves concentration/diafiltration/concentration/diafiltration/concentration in order to adjust the final formulation containing additives such as $MgCl_2$ and/or $CaCl_2$ and/or further additives.

In WO 2004/042012 A2 it is also presented a process to concentrate macromolecules. It is provided a method for concentrating a macromolecule from an aqueous starting solution having solution components, the solution components comprising the macromolecule and an organic polymer, the method comprising:
(1) subjecting the aqueous starting solution to ultrafiltration to concentrate the macromolecule such that a first retentate solution is produced,
(2) adjusting the conductivity of the first retentate solution such that precipitation of the solution components induced by the organic polymer is substantially prevented or substantially reversed to produce a second retentate solution, and
(3) subjecting the second retentate solution to ultrafiltration to further concentrate the macromolecule such that a concentrated solution is produced. According to an embodiment the conductivity may be adjusted by diafiltration against water, suitable diluent or buffer so that the process may run as a combination of ultrafiltration (UF)/diafiltration (DF)/ultrafiltration (UF) steps. The starting material comprises the macromolecule and an organic polymer such as Pluronic F-68.

Further, it is known that a combination of ultrafiltration (UF)/diafiltration (DF) can be used to concentrate antibodies, as shown exemplarily by WO 2006/031560 A2. In this document it is described a process for preparing highly concentrated antibody compositions comprising: a first ultrafiltering of a first antibody preparation to provide a second antibody preparation; diafiltering the second antibody preparation to provide a diafiltered intermediate antibody preparation; and a second ultrafiltering of the diafiltered intermediate antibody preparation to provide a third antibody preparation; wherein one or more of the first ultrafiltering, second ultrafiltering, and the diafiltering are accomplished at about 30° C. to about 50° C. Therefore, it is proposed a process for concentrating proteins including an ultrafiltration (UF), a diafiltration (DF) and a second ultrafiltration (UF) sequence, whereby all steps are performed at elevated temperatures, such as above about 30° C., a specific temperature to be observed during the process steps is essential.

In addition, WO 2009/073569 A2 discloses an aqueous formulation comprising water and a protein, and methods of making the same. The aqueous formulation of the invention may be a high protein formulation and/or may have low levels of conductivity resulting from the low levels of ionic excipients. It is also provided a method of preparing an aqueous formulation comprising a protein and water, the method comprising:
a) providing the protein in a first solution; and
b) subjecting the first solution to diafiltration using water as a diafiltration medium until at least a five fold volume exchange with the water has been achieved to thereby prepare the aqueous formulation.

Therefore, pure water during the diafiltration (DF) step was also used in a DF/UF sequence to generate a solution of highly concentrated protein with a low conductivity. According to our experience, however, even large diafiltration volumes may not be sufficient to completely remove anionic excipients when the biomolecule is positively charged.

Therefore, a conventional UF/DF process known from prior art as already described typically includes three steps. This known 3-step UF/DF process is illustrated in FIG. 2. It is shown a schematic representation of an UF/DF process for conditioning and concentrating a protein solution using two ultrafiltrations UF1 and UF2 and between these both ultrafiltration steps one diafiltration step DF1.

The three steps of FIG. 2 are:
1. UF1: ultrafiltration concentrating the protein solution to, for example, a third to a half of the final target value;
2. DF: diafiltration, usually performed in several cycles thereof, against pure water to remove initial excipients; and
3. UF2: ultrafiltration to concentrate the protein solution to the desired final level.

With regard to such an UF/DF process, the process developers and formulators have generally assumed that a) the excipient profile of the resulting solution will be well-defined, b) the final excipient profile will match that of the medium-exchange solution or diafiltration medium, and c) ultrafiltration will remove residual excipients while diafiltration will avoid residual carryover altogether.

However, the conventional three-step UF/DF process of prior art has been found to have an inadequate performance. While the above assumptions may hold for protein concentrations which are very low, e.g. <<80 mg/mL, our studies have shown that the three-step UF/DF known using a diafiltration step against water to attain high protein concentrations suffers from the disadvantage that residual levels of initial buffer ions at concentrations of e.g. 4 to 10 mM still remain in the solution. However, many biomolecules produced, for example monoclonal antibodies, require a highly concentrated formulation (e.g. 70 mg/mL or more) with defined excipient contents. Thus, the known UF/DF process does not provide the standard of quality which is desired and the permanent increasing requirements during biomolecule-based or protein-based formulation development will not be fulfilled.

Furthermore, as already shown and demonstrated in prior art it is not straightforward to remove charged ions from biomolecule-containing such as protein-containing solutions. As discussed in studies (e.g. Donnan F. G. (1911), The theory of membrane equilibrium and membrane potential in the presence of a non-dialyzable electrolyte, A contribution to physical-chemical physiology, Zeitschrift für Elektrochemie and angewandte physikalische Chemie 17(10), 572-581; Donnan F. G. (1927), Concerning the applicability of thermodynamics to the phenomena of life, J. General Physiology 8, 685-688) the asymmetric distribution of charged ions across a semipermeable membrane creates an electrical potential; the impact depends on total ion concentration and, more precisely, on ion activity in the system (Stoner M. R., Fischer N., Nixon L., Buckel S., Benke M., Austin F., Randolph T. W., & Kendrick B. S. (2004), Protein-solute interactions affect the outcome of ultrafiltration/diafiltration operations, J. Pharm. Sci. 93, 2332-2342). In the case of low total diffusible ion concentrations, the effect of electrostatic interactions between excipient ions and proteins is relatively large (including even the formation of protein-excipient complexes) and clearing excipient ions becomes difficult. In short, a transmembrane electrical potential inhibits free exchange of charged buffer components. A simple separation method to remove these ions is therefore expected to be not successful.

Diafiltration with constant retentate volume, as shown in FIG. 1A, is the most common approach. Assuming a constant sieving coefficient, mass-balance considerations of the different solutes led to development of a model for calculating the clearance of small molecules (Van Reis R., Zydney A. L. (2013), Protein ultrafiltration, in: Flickinger M C. (ed.) Downstream industrial biotechnology: recovery and purification, 1$^{st}$ ed, John Wiley & Sons):

$$c = c_0 \exp(-N \cdot S) \quad (1)$$

where c is the final protein concentration in g/L, $c_0$ is the initial protein feed concentration in g/L, N is the number of diavolumes, and S is the small-molecule sieving coefficient. The diavolume is the ratio between the total collected filtrate or permeate volume and the constant feed volume (Kurnik R. T., Yu A. W., Blank G. S., Burton A. R., Smith D., Athalye A. M., Van Reis R. (1995), Buffer exchange using size exclusion chromatography, countercurrent dialysis, and tangential flow filtration: Models, development, and industrial application, Biotechnology and Bioengineering, 45 (2), 149-157). The sieving coefficient describes the ratio of solute concentrations in the filtrate and retentate. In the ideal case of free solute flow, the permeation of small molecules shows a linear solute decrease as a function of diavolumes on a logarithmic scale with a sieving coefficient reaching 1. Equation 1 is typically used to determine the number of diavolumes or cycles required to reduce small molecules and impurities to a specified level (Harinarayan C., Skidmore K., Kao Y., Zydney A. L., Van Reis R. (2009), Small molecule clearance in ultrafiltration/diafiltration in relation to protein interactions: Study of citrate binding to a fab, Biotechnology and Bioengineering, 102 (6), 1718-1722). However, this equation does not consider non-equilibrium states.

In the case medium exchange involves the addition of a new component i, c is calculated according to:

$$c = c_i[1 - \exp(-N)] \qquad (2)$$

where $c_i$ is the bulk concentration of component i added during diafiltration. S is assumed to be 1.

In practice, however, dialfiltrations often require many more diavolume exchanges than Equations 1 and 2 would suggest to reduce impurities to a given level. However, increasing the number of diafiltration cycles increases processing time and, depending on the protein, can impair protein stability and trigger aggregate formation.

As Harinarayan et al. (loc.cit.) reported, protein-excipient interactions and protein-impurity interactions may affect small-molecule clearance rates. For example, Raibekas et al. (Raibekas A. A., Bures E. J., Siska C. C., Kohno T., Latypov R. F., Kerwin B. A. (2005), Anion binding and controlled aggregation of human interleukin-1 receptor antagonist, Biochemistry, 44 (29), 9871-9879) described the binding of anions like pyrophosphate, citrate, and phosphate to a human recombinant interleukin-1 receptor antagonist (IL-1ra). The estimated dissociation constants were in the millimolar range, and the strength of binding correlated with anion size and the number of ionized groups per molecule. These investigations identified the binding sites as specific positively charged lysine amino acids on a single IL-1ra cluster (Raibekas et al. loc. cit.). Other proteins—including calmodulin, lactic dehydrogenase, citrate synthase, fumarase, and malate dehydrogenase—are known to bind citrate (Neufeld T., Eisenstein M., Muszkat K. A., & Fleminger G. (1998), A citrate-binding site in calmodulin, Journal of Molecular Recognition 11, 20-24). Such excipient-protein interactions may even lead to a phase separation: Esue et al. (Esue O., Kanai S., Liu J., Patapoff T. W., Shire S. J. (2013), Carboxylate-dependent gelation of a monoclonal antibody, Pharm. Res. 26 (2009) 2478-2485) described the carboxylate-dependent gelation of a monoclonal antibody.

Shao and Zydney (Shao J, Zydney A. L. (2004a), Optimization of ultrafiltration/diafiltration processes for partially bound impurities, Biotechnology and Bioengineering, 87 (3), 286-292; Shao J., Zydney A. L., (2004b), Retention of small charged impurities during ultrafiltration, Biotechnology and Bioengineering, 87 (1), 7-13) showed how binding interactions between impurities and large molecules (like proteins) significantly reduce impurity clearance rates. As a consequence, large increases in the number of diavolumes are required to obtain a given level of impurity removal. They proposed an analytical expression for calculating optimal diafiltration steps that accommodate protein-excipient interactions. They also noted these interactions lower the protein concentration that can be used in an optimal diafiltration. Shao and Zydney suggested diluting the feed solution to drive the binding reaction in the reverse direction to increase concentrations of the "free" impurity, and so reduce the overall ultrafiltration/diafiltration process time.

Based on such reflections, and models derived from Equation 1, Harinarayan et al. (loc.cit) found a specific electrostatic interaction between the tested antibody fragment (Fab) and trivalent citrate (while no interaction was observed between the Fab and a monovalent acetate) (Harinarayan et al. loc.cit.).

It should also be remembered that the UF/DF step, especially when it involves highly concentrated protein formulations, increases protein charge density and thus electrostatic protein-excipient interaction. These are related to the Donnan effect, where large charged molecules collect on one side of the membrane, creating a charge gradient across it (e.g. Donnan F. G., (1927), Concerning the applicability of thermodynamics to the phenomena of life, J. General Physiology 8, 685-688; Donnan F. G. (1930), Theorie der Gleichgewichtsionenverteilung bei einem Gelsystem mit veränderlicher Mizellenverteilung, Kolloid-Zeitschrift 51, 24-27). The Donnan effect thus plays an especially prominent role in membrane equilibrium and membrane potential of non-dialysable electrolytes (Brezesinski G., Mögel H. S., Grenzflächen and Kolloide, (1993), Physikalisch-chemische Grundlagen, Spekrum Akademischer Verlag Heidelberg, Berlin, Oxford).

Various researchers have attempted to develop theoretical models incorporating the Donnan effect to better predict excipient and pH changes in protein solutions (e.g. monoclonal antibodies) (e.g. Van Reis R., Goodrich E. M., Yson C. L., Frautschy L. N., Whiteley R., Zydney A. L., (1997), Constant C(wall) ultrafiltration process control, Journal of Membrane Science, 130 (1-2), 123-140). To date, though, these efforts have not entirely succeeded, especially in cases where the biomolecule and the excipient to be removed have opposite charges.

In order to produce highly concentrated biomolecule preparations, in the prior art as already mentioned pure water in an ultrafiltration/diafiltration (UF/DF) step has been used or excipients like glycine or polyethylene glycol have been added in order to influence protein solvation. However, the conventional procedure—diafiltration with pure water to wash all excipients from a biomolecule containing solution, such as a protein solution, followed by an ultrafiltration step to concentrate the biomolecule solution—does not always lead to a clearly defined formulation. Some excipient components are carried over.

For example, a test was performed and it was found that a solution of ~10 mg/mL protein with succinate/sodium chloride retains measurable residual excipients even after conventional UF/DF with up to 20 diafiltration cycles against pure water and 10-fold to 14-fold concentration of the protein. Starting with 25 mM succinate, pH 6, this process leads to a carryover of ~4-5 mM succinate in a final ~100 mg/mL protein concentration. Another test began with a starting solution of 25 mM acetate buffer at pH 5.5; after 15 diafiltration cycles against pure water and 10-fold protein concentration, the final product still contained up to 10 mM acetate.

Thus, for the two briefly described tests, it was not possible to completely remove the initial buffer excipients. In prior art (see Steele and Arias (2014) Accounting for the Donnan Effect in Diafiltration Optimization for High-Concentration UFDF Applications, International BioProcess 12(1), January 2014, 50-54) there was used up to forty diavolumes for removing up to 99.995% of certain undisclosed excipients. This is from a practical and economic point of view not a reasonable procedure.

The degree of carryover depends, for example, on both the pH of the initial biomolecule solution, biomolecule-excipient interaction and the number of diafiltration volumes. Diafiltration with pure water, even with a large number of cycles (approximately 20-25), could not eliminate carryover of anionic excipients like succinate and acetate. In practice, the number of diavolume exchanges necessary to clear the excipients substantially exceeded the number calculated from the above-mentioned Equation 1 (a mathematical model for calculating the clearance of small molecules of a diafiltration). Furthermore, one has to keep in mind, that increasing the diafiltration cycles may have a negative impact on protein integrity and increases process time.

It is therefore an object of the present invention to overcome the deficiencies of prior art and to provide an improved process which allows the preparation of well-defined highly concentrated formulations containing biomolecules, particularly proteins, intended for pharmaceutical or non-pharmaceutical use.

A further object of the present invention is to provide a purer liquid biomolecule formulation product with the process, which may be purified easier and faster compared with the prior art processes, whereby the degree of carryover of excipients, particularly of anionic excipient(s), is reduced or even minimized.

A further object of the present invention is to provide a process, in which the number of diavolume exchanges necessary to clear the excipient(s) is in a reasonable range in order not to impair biomolecule stability and trigger aggregate formation.

A still further object of the present invention is to provide a process which is also feasible in large scale, provides the desired quality standard and operation efficiency with reasonable costs.

SUMMARY OF THE INVENTION

Surprisingly, it was found that the disadvantages known from prior art may be overcome, particularly the carryover problem may be significantly reduced or completely avoided, if an additional diafiltration step, DF1, performed with a liquid medium at a defined high ionic strength, before a second diafiltration (DF2) is employed.

Therefore, in order to overcome the above mentioned disadvantages, an improved and modified process of double ultra- and diafiltration UF/DF is provided. The process of the present invention for the preparation of a highly concentrated liquid formulation containing biomolecules comprising the steps of
  (a) a first ultrafiltration UF1;
  (b) a first diafiltration DF1;
  (c) a second diafiltration DF2; and
  (d) a second ultrafiltration UF2;
wherein an aqueous solution of one or more salts, as liquid medium B, is used for step (b) and water or an aqueous solution of one or more salts, as liquid medium C, is used for step (c), wherein the one or more salts used for step (b) are the same or different from the one or more salts used for step (c) and wherein the liquid medium B has an ionic strength which is higher than the ionic strength of the liquid medium C.

The expression "highly concentrated liquid formulation containing biomolecules" in the frame of the present invention shall be understood in the sense that the biomolecule(s) is (are) present in the liquid formulation in a concentration of 70 mg/ml or more, or 80 mg/ml or more, or 85 mg/ml or more.

The process of the present invention was found to consistently reduce levels of undesired excipient(s) present in the starting liquid biomolecule formulation, preferably below the limit of detection, and resulted in stable liquid formulations of the biomolecules contained. In case the biomolecules are selected to be proteins, the process yielded solutions with only enough exchange-medium counterions to balance proteins' inherent charge and permit the protein to self-buffer. Biomolecule integrity and biomolecule quality was generally found to be acceptable or completely unchanged.

Furthermore, it was completely unexpected that any kind of unwanted excipient(s) present in the starting liquid biomolecule formulation can be removed with the process of the present invention performed under solution conditions such as positively charged excipient(s), negatively charged excipient(s) and neutral excipient(s).

A further advantage of the process according to the invention resides in the fact that it is very mild with regard to physical stress exerted onto the proteins. This can be concluded from a high degree of monomer content throughout the steps of the process.

DETAILED DESCRIPTION OF THE INVENTION

Terms not specifically defined herein should be given the meanings that would be given to them by one of skill in the art in light of the disclosure and the context.

For example, the expressions "liquid formulation", "solution" "soluble" and "dissolved" or "solved" according to the present invention should be understood in their broadest meaning and include all kind of mixtures of a solid or liquid in a liquid medium such as true solutions, dispersions, suspensions and the like, unless otherwise stated.

The expression "highly concentrated" should be understood in the sense that the liquid biomolecule formulation is provided in a concentration which is higher than the starting concentration, preferably significantly higher than before. The exact increase of the concentration provided depends from each single case, the biomolecule and medium chosen as well as conditions and parameters of the ultrafiltration and diafiltration equipments used.

As used herein, the expression "ultrafiltration" or "UF" and similar terms refer to any technique in which a liquid formulation is subjected to a semi-permeable membrane that retains biomolecules, for example proteins, while allowing solvent and solute molecules smaller than the biomolecule to pass through. In the present invention ultrafiltration is used to increase the concentration of biomolecules, for example proteins, in a liquid formulation.

As used herein, the expression "diafiltration" or "DF" and similar terms refer to, for example, using a semi-permeable filtration membrane to remove, replace, or lower the concentration of salts or solvents from liquid formulations containing proteins, peptides, nucleic acids, or other biomolecules. There are two forms of DF, including DF in discontinuous mode and DF in continuous mode. The process of the invention may be performed according to either mode.

As used herein, the term "diafiltration step" refers to a total volume exchange (as far as possible) during the process of diafiltration.

As used herein, the terms "diafiltration/ultrafiltration" or "DF/UF" refer to any process, technique or combination of techniques that employs ultrafiltration and/or diafiltration. In the present invention ultrafiltration and diafiltration are used sequentially.

The terms "excipient" or "excipient(s)" or "excipients" refer in the present invention to one or more substances or compounds, such as auxiliary agents, ions, fragments or any kind of species that are present in the liquid biomolecule formulation besides the biomolecule itself and the solvent(s) used. The excipient(s) present in the starting biomolecule formulation are excipient(s) which shall be reduced or removed as far as possible according to the process of the present invention. These excipient(s) may be charged or neutral in aqueous solution. These excipient(s) to be removed from the starting liquid biomolecule formulation are herein also referred to as "first excipient(s)" or "starting excipient(s)". These first or starting excipient(s) present in the starting liquid biomolecule formulation will be exchanged with other (second) excipient(s) which are more easily removable from the liquid biomolecule formulation, provide better compatibility or are more acceptable due to other reasons in order to obtain a well-defined liquid biomolecule formulation. The second excipient(s) are used in step (b). Also third excipient(s) to be used in step (c) may be optionally used. For the sake of completeness also fourth excipient(s) may be optionally used, i.e. excipient(s) which may be added after completion of the process according to the present invention. Even if the term "excipient" is used in singular it always comprises one or more excipients as the context may allow.

The term "ionic excipient(s)" refers to an ion(s) that has a net charge in an aqueous solution. Examples of ionic excipient(s) include, but are not limited to, anions derived from inorganic and/or organic salts, e.g. inorganic and/or organic buffering salts, or anions or cations, e.g. derived from detergents. The ionic excipients may or may not interact with the biomolecule present.

The expression "salt" refers to an ionic compound resulting from the neutralization of an acid and a base. The salts are composed of positively charged ions, namely cations, and negatively charged ions, namely anions. These ions can be inorganic or organic. An "organic salt" is therefore a compound wherein the cation and/or the anion is an organic compound. In case the acids and bases used are pharmaceutically acceptable also the salts thereof are pharmaceutically acceptable.

The term "water" is intended to mean any type of water which may be used. Purified water may be preferred but according to some embodiments also tap water may be used. The type of water selected depends from the intended use of the obtained liquid biomolecule formulation. Purified water used according to the present invention is water that has been undergone a purification process such as distillation, reverse osmosis, carbon filtering, capacitive or electro-deionization, micro- or ultrafiltration, ultraviolet oxidation or the like to remove impurities to be suitable for use. Combinations of these processes may also be used in order to achieve water of such high purity, e.g. ultrapure water, that its trace contaminants are measured in parts per billion (ppb) or parts per trillion (ppt). In a preferred embodiment, water used in the process of the invention is ultrapure water, for example ultrapure water of type 1, according to ASTM D1193 or ISO 3696.

According to another embodiment, the water used may be sterile water suitable for administration to a subject such as water for injection (WFI). Also, distilled water, bidistilled or deionized water may be used.

The term "exchange" used throughout the present invention has to be understood in its broadest meaning which does usually not represent a complete exchange of one liquid medium containing excipient(s) against another liquid medium containing other excipient(s). It is rather a washing out or diluting of solvent and/or excipient(s). Thus, for example, the excipient succinate in water is washed out to be replaced with the excipient acetate in water (e.g. in step (b)). A variety of other examples of exchanges exists.

A "stable" formulation according to the present invention is one in which the biomolecule, preferably protein, contained therein essentially retains its physical stability and/or chemical stability and/or biological activity upon storage.

The expression "about" or "approximately" means within 20%, preferably within 10% and more preferably within 5% of a given value or range.

Furthermore, it should be noted that the chemical and biological species explicitly mentioned should not be understood to be limited to the specifically described species but those skilled in the art know the equivalent substances and compounds having a similar or comparable effect, reaction or performance which should be within the present scope of protection.

In the following the multi-step process according to the present invention is described. Optimum process conditions and parameters for each individual step may vary depending on the particular biomolecules, excipient(s), mediums and filter systems employed. Unless otherwise specified, the process conditions and parameters of each process step may be readily selected by one of ordinary skill in the art. Exemplary procedures are provided in the Examples section.

According to the present invention an improved process has been developed to prepare clearly defined biomolecule formulations, wherein the final product consists or essentially consists of a highly concentrated biomolecule formulation (biomolecule+solvent(s)) and optionally a specific amount of excipient(s) which is necessary, e.g. in view of the biomolecule used or for other reasons; e.g. ions such as counterions of the biomolecule may or must be present. In essence, it is provided a double ultra-/diafiltration in the order of sequence step (a)-step (b)-step (c)-step (d) or ultrafiltration UF1/diafiltration DF1/diafiltration DF2/ultrafiltration UF2. It is a process that adds a diafiltration against a high-ionic-strength solution (DF1) between the initial concentrating ultrafiltration (UF1) and another diafiltration against water or low-ionic-strength solution (DF2) prior to the second ultrafiltration (UF2).

With reference to FIG. 3 a schematic representation of one exemplary embodiment of an UF/DF process according to the present invention for conditioning and concentrating a liquid biomolecule formulation using two ultrafiltration and two diafiltration steps is shown. In FIG. 3 the legend is as follows:

$c_{P1}$: initial biomolecule concentration;
$c_{P2}$: biomolecule concentration after a first ultrafiltration step UF1;
$c_{P3}$: biomolecule concentration after a second ultrafiltration step UF2.

At first and prior to the first ultrafiltration step UF1 in step (a), the liquid biomolecule formulation is provided either as a commercially available product from a manufacturer on the market or it is prepared based on standard procedures known in prior art. In the initial state the biomolecule is contained in a solvent or a mixture of solvents and is present in a concentration $c_{P1}$. In the frame of the present invention the term "biomolecule" should per se encompass one or more biomolecules even if used in singular.

Besides the contained biomolecule(s), the starting liquid formulation contains a number of excipients (hereinafter also referred to as starting or first excipients), which may be generally indicated as excipients XYZ. The solvent(s) and the excipient(s) contained in the starting liquid biomolecule formulation are hereinafter indicated as liquid medium A.

The (starting or first) excipients XYZ present are, for example, auxiliary agents used to stabilize, solubilise and/or formulate a biomolecule in the starting liquid formulation. However, these excipients shall be reduced to a low level or even removed as far as possible in the final liquid formulation obtained because these excipients could negatively affect the performance, properties and behaviour of the liquid biomolecule formulation, for example, in further processing. The excipient(s) XYZ present result in a formulation which may not be exactly defined which is not desirable at all.

The starting excipients may be in any form present in the liquid formulation such as a solid, complex, ion or the like dissolved or dispersed in the solvent(s) present. It is a matter of course that the excipient(s) are herein understood to mean only those excipient(s) which are present in any form in solution as defined above, because not dissolved and precipitated excipients may be separated easily from the liquid formulation. The excipients XYZ are to be removed by the inventive process while the biomolecule(s) is(are) maintained in solution during the whole process in order to avoid potential biomolecule stress.

These starting or first excipient(s) are not limited according to the present invention, they may be any kind of excipient(s) known in the art which are charged or neutral in aqueous solution. The excipient(s) may be present in the starting liquid biomolecule formulation due to several reasons associated, for example, with the manufacturing, storage, pre-processing of the biomolecule, or properties of the biomolecule itself or the solvent(s) used or other reasons.

The excipient(s) to be reduced or removed as far as possible are the starting excipients which are charged or neutral in aqueous solution, for example, additives used in the preparation or processing of biomolecule; unwanted substances or compounds such as impurities contained in the starting liquid biomolecule formulation; undesired side-products formed during the manufacturing process of the biomolecule; decomposition or degradation products of starting, intermediate or biomolecule end products formed during the production of the biomolecule.

For example, the excipient(s) might be cell components or debris, degradation products of bacteria such as endotoxines, DNA, RNA, undesired lipids, HCP (Host cell proteins), lipopolysaccharides (LPS) or parts thereof; sugars; detergents such as positively charged, negatively charged and also non-ionic species; any kind of negatively or positively charged ions preferably resulting from organic and/or inorganic salts, such as organic and/or inorganic buffer salts, and detergents.

Charged excipients may be, for example, charged ions resulting from organic and/or inorganic salts dissolved in the aqueous solvent such as anions or cations, preferably anions. The charged excipients may be derived from organic and/or anorganic buffer salts. For example, ions resulting from a buffer system used to stabilize the biomolecule (starting or first ions) may be replaced with other ions (second ions).

Therefore, the starting excipient(s) to be removed may be understood as impurities of the liquid formulation. Impurities are usually present in small amounts but the impurities according to the present invention might be present in high quantities, for example, an anion of the buffer system. Therefore, these impurities are herein more correctly referred to as excipient(s) (starting or first excipient(s)).

According to a preferred embodiment the biomolecule and the starting excipient(s) have opposite charges. For example, the biomolecule may be positively charged such as in case of a protein and the excipients to be removed by the process are negatively charged excipients, such as anions. Excipients which may be reduced or removed in this case may be, for example, buffering excipients such as citrate, succinate, acetate, and phosphate.

Therefore, the focus of the present invention may be particularly directed to separate organic ions such as mono- or multivalent negative ions from liquid biomolecule formulations such as liquid protein formulations but not multivalent metal ions.

The biomolecule(s) used according to the present invention is(are) not limited at all, any biomolecule(s) known by those skilled in the art may be used. A biomolecule is any organic substance that is present in living organisms, including large macromolecules such as proteins, carbohydrates, lipids, and nucleic acids, as well as small molecules such as primary metabolites, secondary metabolites, and natural products. Most biomolecules in essential consist of the elements carbon, hydrogen, oxygen, nitrogen, and optionally phosphorous and sulfur. Also other elements may be present but only in small amounts. Biomolecules may be selected from small molecules, monomers, macromolecules and others. Exemplary small molecules are lipids such as phospholipids, glycolipids, sterols; vitamins; hormones; neurotransmitter. Monomers which may be mentioned, but without restriction, are amino acids, nucleotides, monosaccharides etc. Macromolecules or so-called biopolymers, which may be used according to the present invention are, for example, proteins or peptides such as oligopeptides; nucleic acids such as DNA, RNA; oligosaccharides, polysaccharides such as glycogen, starch, chitin, cellulose, fructane, dextrane. Particularly preferred biomolecules are biopolymers, particularly selected from proteins or peptides e.g. oligopeptides, nucleic acids, oligosaccharides, and polysaccharides. Most preferred are proteins or peptides.

The terms "polypeptide" or "protein" are used interchangeably. These terms refer to polymers of amino acids of any length. These terms also include proteins that are post-translationally modified through reactions that include, but are not limited to glycosylation, glycation, acetylation, phosphorylation, oxidation, amidation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with similar or modified properties. Amino acid modifications can be prepared for example by performing site-specific mutagenesis or polymerase chain reaction mediated mutagenesis on its underlying nucleic acid sequence.

The terms "polypeptide" and "protein" thus also include, for example, fusion proteins consisting of an immunoglobulin component (e.g. the Fc component) and a growth factor (e.g. an interleukin), antibodies or any antibody derived molecule formats or antibody fragments.

Therefore, the term "protein" or "polypeptide" includes proteins, polypeptides, fragments thereof, peptides, fusion proteins all of which can be expressed in the selected host cell. Typically, the protein is a recombinant protein, i.e., a protein encoded by a recombinant DNA resulting from molecular cloning. Such proteins can be antibodies, enzymes, cytokines, lymphokines, adhesion molecules, receptors and derivatives or fragments thereof, and any other polypeptides that can serve as agonists or antagonists and/or have therapeutic or diagnostic use or can be used as research reagent. Preferably the protein is a secreted protein or protein fragment, more preferably an antibody or antibody fragment or an Fc-fusion protein. It may also be an antisense RNA, tRNA, rRNAs, other RNAs being part of riboproteins or other regulatory RNAs.

The term "antibody", "antibodies", or "immunoglobulin(s)" as used herein relates to proteins selected from among the globulins, which are formed as a reaction of the host organism to a foreign substance (=antigen) from differentiated B-lymphocytes (plasma cells). They serve to defend specifically against these foreign substances. There are various classes of immunoglobulins: IgA, IgD, IgE, IgG, IgM, IgY, IgW. Preferably the antibody is an IgG antibody, more preferably an IgG1 antibody. The terms immunoglobulin and antibody are used interchangeably. Antibody includes a polyclonal, monoclonal, monospecific, bi-specific, multi-specific, a single chain antibody, an antigen-binding fragment of an antibody (e.g., an Fab or F(ab')2 fragment), a disulfide-linked Fv, etc. Antibodies can be of any species and include chimeric and humanized antibodies.

"Chimeric" antibodies are molecules in which antibody domains or regions are derived from different species. For example the variable region of heavy and light chain can be derived from rat or mouse antibody and the constant regions from a human antibody. In "humanized" antibodies only minimal sequences are derived from a non-human species. Often only the CDR amino acid residues of a human antibody are replaced with the CDR amino acid residues of a nonhuman species such as mouse, rat, rabbit or llama. Sometimes a few key framework amino acid residues with impact on antigen binding specificity and affinity are also replaced by non-human amino acid residues. Antibodies may be produced through chemical synthesis, via recombinant or transgenic means, via cell (e.g., hybridoma) culture, or by other means.

Immunoglobulins are tetrameric polypeptides composed of two pairs of a heterodimer each formed by a heavy and light chain. Stabilization of both the heterodimers as well as the tetrameric polypeptide structure occurs via interchain disulfide bridges. Each chain is composed of structural domains called "immunoglobulin domains" or "immunoglobulin regions" whereby the terms "domain" or "region" are used interchangeably. Each domain contains about 70-110 amino acids and forms a compact three-dimensional structure. Both heavy and light chain contain at their N-terminal end a "variable domain" or "variable region" with less conserved sequences which is responsible for antigen recognition and binding. The variable region of the light chain is also referred to as "VL" and the variable region of the heavy chain as "VH".

The term "Fab fragment(s)" (Fragment antigen-binding=Fab) or "Fab" consist of the variable regions of both antibody heavy and light chains (VH and VL) which are held together by the adjacent constant regions (CH1 and CL). These may be formed by protease digestion, e.g. with papain, from conventional antibodies, but similar Fab fragments may also be produced in the meantime by genetic engineering. Further antibody fragments include "F(ab')2 fragments" or "F(ab')2", which may be prepared by proteolytic cleaving with pepsin or by genetic engineering in which both Fab arms of an antibody are still linked via inter-heavy chain disulfide bridges located within the hinge region.

The immunoglobulin fragments composed of the CH2 and CH3 domains of the antibody heavy chain are called "Fc fragments", "Fc region" or "Fc" because of their crystallization propensity (Fc=fragment crystallizable). These may be formed by protease digestion, e.g. with papain or pepsin from conventional antibodies but may also be produced by genetic engineering. The N-terminal part of the Fc fragment might vary depending on how many amino acids of the hinge region are still present.

The term "Fc-fusion protein" describes polypeptides which contain as a fusion partner a natural or modified (e.g. substitutions, deletions, insertions) Fc region of an immunoglobulin. Fc fusion proteins can be either naturally occurring proteins (e.g. antibodies) or engineered recombinant proteins (e.g. TNF receptor-Fc fusion protein or a VH region fused to an Fc region). The Fc-fusion proteins can exist either as monomers or as multimers whereby polypeptides can have identical or different sequences, might contain linker sequences between the two fusion partners and/or part of the hinge region or modified hinge regions or the polypeptide is fused directly to the CH2 domain.

Using genetic engineering methods it is possible to produce shortened antibody fragments which consist only of the variable regions of the heavy (VH) and of the light chain (VL). These are referred to as "Fv fragments" (Fragment variable=fragment of the variable part) or "Fv". Since these Fv-fragments lack the covalent bonding of the two chains by the cysteines of the constant chains, the Fv fragments are often stabilized. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a "single-chain-Fv" or "scFv". Examples of scFv-antibody proteins of this kind are known from the prior art. In addition, more than one VH and/or VL region can be linked together.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucine-zipper domains. However, there are also strategies in which the interaction between the VH/VL regions of the scFv is used for the multimerisation (e.g. dia-, tri- and pentabodies). By diabody the skilled person means a bivalent homodimeric scFv derivative. The shortening of the linker in a scFv molecule to 5-10 amino acids leads to the formation of homodimers in which an inter-chain VH/VL-superimposition takes place. Diabodies may additionally be stabilized by the incorporation of disulphide bridges. Examples of diabody-antibody proteins are known from the prior art.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a linker region. Examples of minibody-antibody proteins are known from the prior art.

By triabody the skilled person means a: trivalent homotrimeric scFv derivative. ScFv derivatives wherein VH-VL is fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures.

A nanobody also known as single-domain antibody is an antibody fragment consisting of a single monomeric variable antibody domain. Like a whole antibody, it is able to bind selectively to a specific antigen. Nanobodies have a molecular weight of about 12-15 kDa, and are therefore much smaller than common antibodies having molecular weights in the range of 150 to 160 kDa, which are composed of two heavy protein chains and two light chains. They are also smaller than Fab fragments (about 50 kDa) and single-chain variable fragments (about 25 kDa).

The term "antibody derived molecule(s)" is used interchangeably with "antibody derived fragments" or "antibody fragments" and refers to polypeptides which contain only part(s) of one or more antibody domain(s) or region(s) and/or complete domain(s) or region(s). The antibody fragments can be either a) forming a molecule on their own, b) linked with each other in different combinations, c) fused to non-antibody sequences, d) fused or linked to non-polypeptide (e.g. radionucleotides) or d) any combination of the above. These polypeptides can exist either as monomers or as multimers whereby polypeptides can have identical or different sequences.

However, the proteins to be used per se as biomolecule shall not be limited to the use in the pharmaceutical and biotechnology sectors but any kind of protein in any type of application field can be used. Proteins are also known to be used in a variety of non-pharmaceutical applications, for example in the food stuff industry, animal feed industry, textile industry, chemical-technical industry, detergent industry and other sectors.

Preferred proteins are therapeutic proteins, non-therapeutic proteins, antibodies, antigen-binding fragments or nanobodies, particularly monoclonal antibodies and related compounds or formates.

The process of the present invention may be employed in a particular advantageous manner if the biomolecules are positively charged and the excipient(s) (starting or first excipients) to be removed by the process are negatively charged excipient(s).

Starting from the liquid biomolecule formulation provided steps (a) to step (d) are performed. The specific composition of the starting liquid biomolecule formulation will determine which excipients shall be exchanged or removed by the process.

In step (a) a first ultrafiltration (UF1) is performed by which the biomolecule containing liquid formulation is concentrated and a concentration up to $c_{P2}$ of the biomolecule is reached. That is, the ultrafiltration UF1 of step (a) is used to concentrate the liquid biomolecule formulation, preferably up to about 10%-70%, or, more preferably about 15%-60%, or, most preferably about 25%-50% compared with the initial concentration of the liquid biomolecule formulation. This kind of concentration has the advantage to reduce the overall process volume for the next DF step and this also leads to reduced process times.

The ultrafiltration as well as the subsequent diafiltrations selectively utilizes permeable (porous) membrane filters to separate the components of the liquid formulation based on their molecular size. Per se a membrane retains biomolecules that are larger than the pores of the membrane while smaller molecules such as salts, ions, solvents such as water, which are permeable, freely pass through the membrane. One parameter for selecting a membrane is its retention characteristics. As a general rule, the molecular weight cut-off (MWCO) of the membrane should be ⅓ to ⅙ the molecular weight of the biomolecule to be retained. It is a matter of course that the excipient(s) to be removed have a lower or even significantly lower molecular weight than the biomolecule so that the biomolecule is retained and not the excipient(s).

Subsequently to the concentration step (a) and particularly preferred without any intermediate steps in between, the further steps (b) and (c) of the present invention are performed. Therefore, the liquid biomolecule formulation used in step (a) contains a liquid medium A composed of solvent(s) and starting or first excipient(s), whereby the medium A is exchanged in step (b) with medium B, and medium B is exchanged in step (c) with medium C, whereby the liquid biomolecule formulation primarily containing liquid medium C (and probably small amounts of liquid mediums B and C) results, which has a reduced content of the starting excipient(s), being preferably lower than the level of detection.

Thus, medium A contains or consists of solvent(s) and undesired starting or first excipient(s), which are planned to be exchanged/replaced, whereby medium A is exchanged by means of liquid medium B against liquid medium C. Liquid medium B contains or consists of solvent(s) and second excipient(s), and medium C contains or consists of solvent(s) and third excipient(s), preferably solvent(s) only.

The second excipient(s) and optional third excipient(s) are the same or different from each other; both are different or at least partially different from the first excipient(s) which shall be removed. "At least partially different" has to be understood in the sense that e.g. one or more of the first excipients may be the same with one or more of the second excipients. For example, sodium chloride may be present as first excipient and also as second excipient. This does not interfere with the process to be performed. However, there is always a difference between first and second excipients in total in order to result in a real exchange of first excipient(s) by second excipient(s). In fact, the type of the excipient is not of particular importance because any type of excipient whether charged or neutral may be removed. In fact, the invention provides the possibility to remove any type of excipient(s) although strong biomolecule-excipient(s) interactions being present. By way of illustration, in an exemplary simplified embodiment the first excipient is an acetate buffer salt which is exchanged with a second excipient such as a succinate buffer salt, and the second excipient is exchanged with a third excipient e.g. chloride. Such an embodiment is possible if it is accepted to have two types of anions, namely succinate/chloride, at the same time in the end product. If only one specific excipient shall be present in the end product (highly concentrated liquid biomolecule formulation) the liquid medium C consists or essentially consists of water. However, also the reverse or another order is possible: the first excipient may be succinate, which is replaced by acetate as second excipient and so on.

The "second excipients" and "third excipients" are herein used interchangeably with "salts" whereas the "starting or first excipients" and also "fourth excipients" (which may be added to the obtained final liquid biomolecule formulation) are not only salts but may be also other substances or compounds as herein described, for example any kind of suitable auxiliary agents such as detergents, surfactants, sugars etc.

Thus, the starting or first excipient(s) present in the starting liquid biomolecule formulation are excipient(s) which are not desired to be present and shall be removed by the process according to the present invention. In order to achieve this reduced level of starting or first excipient(s) the liquid medium B used in step (b) has an ionic strength which is higher than the ionic strength of the liquid medium C used in step (c).

Mediums B and C may be selected from any liquid medium which may be used in connection with a biomolecule, which may be able to maintain the biomolecule in a liquid formulation and do not have any negative influence on the characteristics of the biomolecule used. It is a matter of course that the liquid mediums B and C (and A) used should not in any way transform or alter the biomolecule contained in it. The only interaction which may be accepted is an ionic interaction of the ions contained in the liquid medium with the biomolecule in order to stabilize it. This is in case the biomolecule and the liquid medium have opposite charges. For example, the biomolecule is a positively charged biomolecule such as a protein and the anions of the liquid medium interact with the protein to stabilize it in solution.

Mediums B and C and preferably also medium A represent an aqueous solution. Therefore, the solution always contains water. Further, the solution contains a solvent or a mixture of solvents, particularly the solution contains water and another solvent or water and a mixture of solvents. The solvent(s) may be selected from any known solvent which is miscible with water and does not in any manner adversely affect the properties of the solved biomolecule such as an antibody or nanobody. In case the biomolecule provided is intended for pharmaceutical use it is a matter of course that the solvent(s) selected shall be likewise suitable for pharmaceutical use, too.

According to a preferred embodiment the solvent or solvents is/are preferably selected from the group consisting of mixtures of water and organic solvent(s) miscible with water. As organic solvent(s) may be exemplarily mentioned but not limited to alcohols such as ethanol, methanol, glycols, sugar alcohols, e.g. glycerine, acetone, acetonitrile, methyl ethyl ketone, ethers (those which are miscible with water) such as dioxan, diglyme, dimethylformamide, N-methyl-pyrrolidone, tetrahydrofuran, and the like and mixtures thereof. The type of solvent(s) used strongly depends from the biomolecule(s) present and the intended use of the end product.

The solution may contain predominantly organic solvent(s); however, it may be preferred if the solvent is predominantly composed of water, so that water represents the main part of the solvents present. According to a further preferred embodiment the solvent used may consist or essentially consist of water alone.

The solvent(s) used in liquid mediums A, B and C may be the same or different. According to a preferred embodiment the solvent(s) used is(are) the same in all liquid mediums A, B, and C. According to a particularly preferred embodiment the solvent is water.

As liquid medium B and/or C (and also liquid medium A) aqueous salt solutions are used, organic salt solutions and/or inorganic salt solutions in water may be exemplarily mentioned. The organic and/or inorganic salts used are preferably water soluble and completely inert with regard to the biomolecule used.

In a preferred mode of the invention liquid medium B comprises sodium chloride in a concentration from about 150 to about 900 mM, increasingly preferred from about 200 to about 700 mM, from about 400 to about 600 mM, and from about 450 to about 550 mM. This mode is especially preferred when liquid medium B does not comprise a specific low molecular weight buffering agent.

Such mode is advantageous in view of the pH values of the subsequent liquid media. Probably due to the fact that sodium chloride has no buffer capacity the pH value of such process step (b) and/or one or more of the following steps varies only in minor ranges, i.e. less than about 0.4, preferably less than about 0.3 pH, even more preferred less than about 0.2 pH values. Examples 3, 6, 9, 10, 11, 12, and 13 exemplify this mode with 200 and 500 mM NaCl and a resulting pH of the liquid medium D regularly just about 0 to 0.3 pH values below the pH value of liquid medium B, i.e. slightly more acidic.

This mode of the invention is especially useful for biomolecules which are sensitive against stronger pH variations.

The organic and inorganic salts used are not limited according to the present invention if they may be used to provide a liquid formulation of the biomolecule present. The salts used in the liquid medium B and/or C may be organic and/or inorganic salts, preferably organic and/or inorganic buffer salts, e.g. usable as biological buffers.

As is known a buffer is a combination of a weak acid or a weak base and its conjugate salt form that keeps the pH from shifting out of the optimal range when added acid or base gets into the system. It is a matter of course that the buffer in the liquid medium used should not in any way react or alter or negatively interact with the biomolecule contained in it, except for the allowed ionic interactions between biomolecule and counterions. Usually the buffers used are freely soluble in water and poorly soluble in other solvents and they represent an inert system. There are a variety of different types of buffer systems available. The skilled person is able to find and select suitable buffer systems which may be used in the present invention.

Therefore, the aqueous solution in form of the liquid mediums B and or C (and also A) represents or may contain a buffer which is on basis of water as solvent or represents or may contain a buffer which is on basis of another solvent or solvents but contains water.

The organic acids and bases to prepare the buffer or the buffers per se are not limited according to the frame of the present invention but any acid, base or buffer usable in connection with the biomolecule selected may be used. In case the biomolecule is intended for a pharmaceutical use the buffer shall be also selected from pharmaceutically acceptable buffers, e.g. biological buffers.

Therefore, the buffer may be, for example, selected from one or more pharmaceutically acceptable or compatible buffers or buffering agents. In the present invention so-called biological buffers may be used, i.e. buffers which are known from prior art to be used for biological system or in the context thereof.

Exemplary biological buffers which may be used in or as liquid medium A, B, and C according to the present invention may be listed as follows but without limitation to the mentioned specific examples:

Possible buffers or buffer salts are on basis of N-(2-acetamido)-aminoethanesulfonic acid (ACES) and salts thereof, acetic acid and salts thereof, aconitic acid and salts thereof, adipic acid and salts thereof, ascorbic acid and salts thereof, N-(2-Acetamido)-iminodiacetic acid (ADA) and salts thereof, ammonia and salts thereof, ammonium chloride, 2-amino-2-methyl-1-propanol (AMP), 2-amino-2-methyl-1,3-propanediol, ammediol (AMPD), N-(1,1-Dimethyl-2-hydroxyethyl)-3-amino-2-hydroxypropanesulfonic acid (AMPSO) and salts thereof, N,N-bis-(2-hydroxyethyl)-2-aminoethanesulfonic acid (BES) and salts thereof, benzoic acid and salts thereof, bicarbonates such as sodium hydrogen carbonate, N,N'-bis(2-hydroxyethyl)-glycine (bicine), Tris buffers such as tris(hydroxymethyl)-aminomethane, [bis-(2-hydroxyethyl)-imino]-tris-(hydroxymethylmethane) (Bis-Tris), 1,3-bis[tris(hydroxymethyl)-methylamino]propane (Bis-Tris-Propane), boric acid and salts thereof, dimethylarsinic acid (Cacodylate) and salts thereof, 3-(cyclohexylamino)-propanesulfonic acid (CAPS) and salts thereof, 3-(cyclohexylamino)-2-hydroxy-1-propanesulfonic acid (CAPSO) and salts thereof, carbonic acid and salts thereof, carbonates such as sodium carbonate, cyclohexylaminoethanesulfonic acid (CHES) and salts thereof, citric acid and salts thereof, 3-[N-bis(hydroxyethyl)amino]-2-hydroxypropanesulfonic acid (DIPSO) and salts thereof, formic acid and salts thereof, gluconic acid and salts thereof, glyceric acid and salts thereof, glutamic acid and salts thereof, glycines such as glycylglycine, N-(2-hydroxyethyl)-piperazine-N'-ethanesulfonic acid (HEPES) and salts thereof, N-(2-hydroxyethyl)-piperazine-N'-3-propanesulfonic acid (HEPPS, EPPS) and salts thereof, N-(2-hydroxyethyl)-piperazine-N'-2-hydroxypropanesulfonic acid (HEPPSO) and salts thereof, imidazoles, lactic acid and salts thereof, malic acid and salt thereof, maleic acid and salts thereof, 2-(N-morpholino)-ethanesulfonic acid (MES) and salts thereof, 3-(N-morpholino)-propanesulfonic acid (MOPS) and salts thereof, 3-(N-morpholino)-2-hydroxypropanesulfonic acid (MOPSO) and salts thereof, phosphoric acid and salts thereof, piperazine-N,N'-bis(2-ethanesulfonic acid) (PIPES) and salts thereof, piperazine-N,N'-bis(2-hydroxypropanesulfonic acid) (POPSO) and salts thereof, pyridines, succinic acid and salts thereof, 3-{[tris(hydroxymethyl)-methyl]-amino}-propanesulfonic acid (TAPS) and salts thereof, 3-[N-tris(hydroxymethyl)-methylamino]-2-hydroxypropanesulfonic acid (TAPSO) and salts thereof, tartaric acid and salts thereof, taurine (2-aminoethanesulfonic acid, AES and salts thereof), triethanolamine (TEA), 2-[tris(hydroxymethyl)-methylamino]-ethanesulfonic acid (TES) and salts thereof, and N-[tris(hydroxymethyl)-methyl]-glycine (tricine).

Whereas the most buffers mentioned above are derived from organic salts also buffers on basis of inorganic salts may per se be used, such as phosphate buffers, for example, potassium hydrogen phosphate buffers and the like.

Also mixed buffers containing inorganic and organic salts may be used.

Further usable organic salts (inner salts) which are at the same time buffers, particularly biological buffers, are amino acids in aqueous solution. Amino acids which may be used are, for example, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine; particularly preferred amino acids are alanine, arginine, glutamine, glycine, histidine, lysine, and proline.

A buffer is a mixture of substances, i.e. a mixture of a weak base and the strong conjugated acid or a weak acid and the strong conjugated base, however, the buffer may be indicated in the present invention with reference to the acid or base or its respective conjugate salt form, only. For example an "acetate" or "acetate buffer" shall be understood as a buffer which contains acetic acid and acetate salt(s). Those skilled in the art may readily understand the context in which it is referred to a buffer system and which components are contained in it.

Preferred buffers which may be used as or in medium B and/or C, are exemplarily selected, but without limitation, from the group consisting of phosphoric acid and salts thereof, citric acid and salts thereof, tris, succinic acid and salts thereof, malic acid and salts thereof, tartaric and salts thereof, acetic acid and salts thereof, lactic acid and salts thereof, aconitic acid and salts thereof, ascorbic acid and salts thereof, glutamic acid and salts thereof, ammoniumchloride, triethanolamine, alanine, arginine, glutamine, glycine, histidine, lysine, and proline.

A buffer is understood according to the present invention to be composed of a solvent(s) and inorganic and/or organic salt(s), the salt(s) being present in form of dissolved ions which are herein also referred to as excipient(s).

Instead of organic and/or inorganic buffer salt(s) also other salts may be used. For example any inorganic salt(s) may be used. The inorganic salt is not limited according to the present invention, any inorganic salt which is soluble in an aqueous solution and does not interfere with the biomolecule used may be employed. The inorganic salt is for example selected from the group consisting of alkali salts or alkaline earth salts of sulfates, nitrates, phosphates, carbonates, halogenides, borates, silicates and the like.

If a pharmaceutically acceptable product shall be provided the inorganic salt as well as the organic salt shall be selected from the group of pharmaceutically acceptable salts per se known. For example, pharmaceutically acceptable inorganic salts are selected from sodium salts such as sodium halides, preferably sodium chloride, sodium sulfate, sodium borate; calcium salts such as calcium halides, preferably calcium chloride, calcium sulfate, calcium borate; magnesium salts such as magnesium halides, preferably magnesium chloride, magnesium sulfate, magnesium borate, and combinations thereof as well as other pharmaceutically acceptable inorganic salts.

A particularly preferred inorganic salt is sodium chloride due to its advantages properties. For example, sodium chloride has only a minor influence on the pH value and is present in a number of known buffer systems. A biomolecule will not be affected by sodium chloride and it is known to be harmless for animal and human.

According to the present invention a salt resulting in any type of charged ion in aqueous solution such as any mono- or multivalent ion may be used. For example mono-, divalent or trivalent ions may be used. According to one embodiment monovalent ions may be preferably used.

The condition with regard to the liquid medium B and liquid medium C according to the present invention which must be observed and fulfilled is that liquid medium B has an ionic strength which is higher than the ionic strength of liquid medium C. This requirement is an essential feature of the process provided in order to achieve the desired results.

It is known that the ionic strength of a solution is a measure of the concentration of ions in the solution. The ionic compounds dissolve in water, dissociate into ions and result in an ionic strength of the solution which is a function of the concentration of all ions present:

$$I = \frac{1}{2}\sum_{i=1}^{n} c_i z_i^2$$

In this equation $c_i$ is the molar concentration of the ion i (M, mol/L), $z_i$ is the charge number of that ion, and the sum is taken over all ions n in the solution. For sodium chloride the ionic strength is equal to the concentration, but for salts such as $MgSO_4$ the ionic strength is four times higher so that multivalent ions contribute strongly to the ionic strength.

Furthermore, it is also known how a desired ionic strength of a salt solution, for example a buffer, may be adjusted; the setting of the ionic strength of a salt solution can be done depending on the concentration and ionic potency of the salts present. Furthermore, a vast number of publications and patent documents exist in prior art so that a specific value or range of the ionic strength may be looked up in a handbook, a monograph or the like. Therefore, the skilled person is able to provide a salt solution which has the required ionic strength.

According to a preferred embodiment liquid medium B has a high ionic strength expressed in form of a concentration of at least about 20 mM or more, or, preferably, at least about 100 mM or more, or, most preferred, at least about 200 mM or more.

Furthermore, it is preferred if liquid medium C has a low ionic strength expressed in form of a concentration of about 150 mM or lower, or, preferably about 100 mM or lower, or, more preferably about 75 mM or lower, or, most preferred about 50 mM or lower.

Thus, the liquid medium B used in diafiltration DF1 has a higher ionic strength compared with the liquid medium C used in diafiltration DF2. As a matter of rule the ionic strength of liquid medium B indicated in form of a concentration may be in the range of from about 20 mM up to the limit of solubility of the salt, or, particularly preferred, from about 100 mM to 1000 mM, or, more preferred about 150 mM to 750 mM, or, most preferred from about 200 mM to 500 mM.

The limit of solubility shall be understood as the maximum solute concentration that can be dissolved at a given temperature. The extent of the solubility of a substance in a specific solvent is e.g. measured as the saturation concentration, where adding more solute does not increase the concentration of the solution and begins to precipitate the excess amount of solute. Thus, the limit of the solubility or quantitative solubility of a salt is the maximum concentration of the salt in the solvent(s) resulting in a system having just one phase.

Although the limit of solubility is dependent from temperature, pressure and the pH of the solution, the skilled person will be able to select and adjust the desired concentration based on the values known from prior art. For example, the solubility for the following salts in water (20-25° C.) is indicated:
sodium citrate=920 g/l=about 3 Mol/l
sodium chloride=359 g/l=about 6 Mol/l
sodium acetate=1233 g/l=15 Mol/l.

Thus, for example sodium chloride may be used in an ionic strength given as concentration from about 20 mM up to about 6 Mol/l.

Further, the ionic strength of liquid medium C (expressed as concentration) may be in the range of from about 0 mM to 150 mM, or, particularly preferred, from about 0 mM to 100, or, more preferred, about 0 mM to 75 mM, or, most preferred from about 0 mM to 50 mM.

In the present invention an aqueous solution of one or more salts as liquid medium B is used for step (b) and water or an aqueous solution of one or more salts as liquid medium C is used for step (c), and the liquid medium B has an ionic strength which is higher than the ionic strength of the liquid medium C. According to a preferred embodiment the difference between the ionic strength of the liquid medium B and the ionic strength of the liquid medium C indicated as concentration is preferably at least about 100 mM, or, more preferred at least about 200 mM, or, most preferred at least about 500 mM.

Therefore, if the ionic strength of the liquid medium B is selected to be about 500 mM the ionic strength of the liquid medium C is lower than about 500 mM, preferably selected to be about 400 mM or lower, or, more preferred, about 300 mM or lower, or, most preferred, about 0 mM. For example, water is a liquid medium C that has an ionic strength of about 0 mM and also an electric conductivity which is about 0 mS/cm.

Furthermore, also the starting liquid medium A preferably has a lower ionic strength than liquid medium B. But this is not in any case necessary. If the liquid medium A has a higher ionic strength than liquid medium B the process of the present invention may be adjusted accordingly in that the cycle number in step (b) and optionally also step (c) may be preferably increased, respectively. The skilled person is readily able to optimize the process steps accordingly.

If there arise problems with the stability of the biomolecule due to the ionic strength of the liquid medium being too high, it is a matter of fact that a lower ionic strength of the liquid medium has to be used and the process steps will be adapted accordingly.

Therefore, usually the ionic strength of liquid medium A is higher than the ionic strength of liquid medium B but also the reverse is possible.

The liquid medium A may be provided with an ionic strength being in the suitable range, which may be controlled by the concentration step (a). It is also possible that the liquid medium A may be diluted with water in order to obtain a lower ionic strength but this is not preferred.

In a particularly preferred embodiment the liquid medium C used for step (c) (DF2) is water. For pharmaceutical use it is preferred that any water to be used during the whole process, per se or as aqueous solution in a medium, should be very pure water in order to avoid a contamination of the liquid biomolecule formulation with ions contained in the water as already explained. Therefore, it is useful to employ ultrapure water, for example ultrapure water of type 1, according to ASTM D1193 or ISO 3696. However, for other non-pharmaceutical uses also tap water may be used.

So, the medium or solvent exchanging steps in the process according to the present invention take place via a liquid medium having high ionic strength (DF1) to a medium having low ionic strength (DF2) in order to remove the undesired excipients present. Without wished to be bound by a theory it is presumed that the transfer from higher ionic strength to lower ionic strength weakens the biomolecule-excipient(s) interactions so that these excipient(s) may be reduced or removed as far as possible.

Instead of the ionic strength the electrical conductivity which is associated with the ionic strength may be employed to determine the mediums used. An empirical method relies on a simplified linear relationship between electrical conductivity and the ionic strength. Thus, for example, a liquid medium B having an ionic strength in the range from 200 mM to 500 mM approximately has an electrical conductivity in the range from 10 mS/cm to 50 mS/cm The above values for the electrical conductivity are given only for illustrative purposes and as a control due to the simplified linear relationship, but the ionic strength (given as concentration) appears to be the accurate parameter in the present invention.

Furthermore, a low electrical conductivity may be indicative that the liquid formulation has significantly reduced excipients including ionic excipients so that the conductivity may be used to determine the purification content obtained.

Depending from the biomolecules and the liquid mediums selected the parameters and conditions of the ultrafiltration and diafiltration steps, which are per se known from prior art, can be readily selected and adapted accordingly by the skilled person. This belongs to the general knowledge of the skilled person. For example, if the biomolecule is selected to be a protein it is preferred that both diafiltration steps DF1 and DF2 will be run at a pH below the protein's isoelectric point. Details are given in the Examples section.

For example, the pH value of the liquid mediums A, B, C is not an issue in the process of the invention because the process functions at any pH value. The pH value may be of interest if a charged ion is only present in dependence from the pH adjusted. For example, the acetate anion is only present in the chemical equilibrium acetate/acetic acid if the pH>3.75. Therefore, it is a matter of course to perform the process in a suitable pH value or range where the salt or ion to be used to perform an exchange is present with the suitable charge.

In addition, it can be preferred that both diafiltrations are consecutively performed in the same diafiltration system with the same separation filter but different mediums B and C. Other embodiments are possible.

In a preferred embodiment of the invention the first diafiltration (DF1) of step (b) may be repeated several times prior to performing the subsequent step (c). That is the exchange of liquid medium B may be performed for a number of times in the form of medium cycles as may be seen in FIG. 1A. Thus, the exchange of liquid medium B may be performed with x medium cycles, whereby preferably x=2 to 10, more preferably x=2 to 8, most preferably x=2 to 6.

In other words, if x=2, step (b) is repeated 2 times, the cycle of FIG. 2A is passed 2 times and for any cycle the same liquid medium B is added as diafiltration medium with each cycle. As a rule of fist, the number of cycles will be usually increased with decreasing ionic strength (or concentration) of the liquid medium B used. The number of cycles possible also depends from the type of the biomolecule used which must tolerate the number of cycles without damage.

The first diafiltration DF1, which is preferably carried out at constant retentate volume, is therefore preferably performed against medium B in an amount to at least about two times the volume of medium B up to an amount of 10 times the volume of medium B. Thus, the process step (b) is performed with at least a determined volume exchange, for example a 2-fold volume exchange with liquid medium B.

In a further preferred embodiment of the invention the second diafiltration (DF2) of step (c) may be repeated several times prior to performing the subsequent step (d). That is the exchange of liquid medium C may be performed for a number of times in the form of medium cycles as may be seen in FIG. 1A. Thus, the exchange of liquid medium C may be performed with y medium cycles, whereby preferably y=2 to 10, more preferably y=2 to 8, most preferably y=2 to 6.

In other words, if y=4, step (c) is repeated 4 times, the cycle of FIG. 2A is passed 4 times and for any cycle the same liquid medium C is added as diafiltration medium with each cycle.

The second diafiltration DF2, which is preferably carried out at constant retentate volume, is therefore preferably performed against medium C in an amount to at least about two times the volume of medium C up to an amount of 10 times the volume of medium C. Thus, the process step (c) is performed with at least a determined volume exchange, for example a 2-fold volume exchange with liquid medium C.

The number of exchange volumes or exchange cycles highly depends on the diafiltration medium used, for example the ionic strength or concentration used. The skilled person is readily able to find out the optimum number of cycles of step (b) and step (c), respectively, by routine experimentation.

In a preferred embodiment, the second diafiltration DF2 is performed in accordance with the process of the invention using water alone as the diafiltration medium C.

In a further preferred mode of the present invention it has been found to be advantageous in step (c) (DF2), if only water is used as solvent, a small amount of a conductive salt(s) such as sodium chloride may be present to control the electrical conductivity. If only water is present the electrical conductivity is 0 mS/cm so that no measurable value is obtained. This is due to the fact that some UF/DF systems are run using conductivity probes. Therefore a small amount of e.g. 0.001 to 0.003 weight % of conductive salt is preferably added during or after step (c) (DF2) in order to better control the process. Than, the liquid medium C essentially consists of water due to the presence of a small amount of conductive salt(s).

According to a further preferred embodiment the liquid mediums B and C are the same and differ only with regard to the ionic strength used. For example, the conductive salt(s) represent the second and third excipient(s), only present in different concentrations.

In the subsequent step (d) a second ultrafiltration (UF2) is performed in order to obtain the liquid biomolecule formulation in concentrated form and a concentration up to $c_{P3}$ of the biomolecule is reached. Thus, the ultrafiltration UF2 of step (d) is used to concentrate the liquid biomolecule formulation to the desired value.

The ultrafiltrations according to step (a) and (d) can be accomplished with the same ultrafilter membrane. The ultrafiltration steps may be performed with any suitable ultrafilter apparatus or ultrafilter membrane known.

According to a preferred embodiment the process of the present invention may be used to remove negatively charged excipient(s) from the starting liquid medium A containing the biomolecule(s) as positively charged compounds. In this embodiment a part of the negatively charged excipient(s) may be used to stabilize the biomolecule in the liquid formulation. For example, a positively charged protein may be stabilized by the presence of anions. With the process of the present invention the anions will be reduced or removed as far as possible or necessary. Therefore, the anions (starting or first excipients) present in liquid medium A to stabilize the biomolecule will be replaced with anions (second excipients) present in liquid medium B so that the kind of anions in step (b) will represent the counterions of the biomolecule. The liquid medium C (third excipients, if present) having a lower ionic strength than liquid medium B will usually not result in an exchange of the anions (second excipients) already present in step (b) as counterions of the biomolecule. As a result, the anions (second excipients) present in liquid medium B will determine the counterions of the biomolecule so that the counterions may be selected accordingly. Therefore, in this exemplary case, the excipients of liquid medium B are the excipients which form a biomolecule-excipient complex obtained in step (d) of the inventive process.

Furthermore, in the process of the present invention performed under solution conditions it is possible to use any excipient(s) for the first, second or third excipients such as positively charged excipient(s), negatively charged excipient(s) and neutral excipient(s). It is a matter of course that if the first or starting excipient(s) have a specific charge that also the second excipient(s) have the same corresponding charge in order to replace the first excipient(s) if this is required for any reason. E.g. the first excipient(s) are negatively charged, interact with the biomolecule and shall be replaced, then also the second excipients have a negatively charge etc.

The second and optional third excipients may be selected depending from the biomolecules, solvents and first excipient(s) present. The second and third excipients are selected to be salts, preferably organic and/or inorganic salts, more preferably organic and/or inorganic buffer salts or ions derived thereof as herein described.

During the process it is in any case useful that excipient analyses were performed at each stage of the process in order to monitor changes in solution conditions.

In the process of the present invention the excipient(s) present in liquid medium A are reduced as far as possible or required. According to a preferred embodiment the excipient(s) present in starting liquid medium A are reduced to be lower than the level of detection. In this connection the terms "Level of Detection" (LOD) and "Level of Quantification" (LOQ) are used. These terms are used to describe the smallest concentration of a measurand that can be reliably measured by an analytical procedure. Typically a test is simply not capable of accurately measuring analyte concentrations down to zero. Sufficient analyte concentration must be present to produce an analytical signal that can reliably be distinguished from "analytical noise," the signal produced in the absence of analyte. Various analytical specifications can be applied to ensure that the LOD is meaningful and clearly distinguishable from a negative or blank sample. In this regard it is referred to the Examples section. The following LODs and LOQs have been found

| | | |
|---|---|---|
| phosphate: | LOQ = 0.05 mg/L; | |
| acetate: | LOQ = 0.7 mM | LOD = 0.1 mM; |
| citrate: | LOQ = 0.1 mM | LOD = 0.01 mM; |
| succinat: | LOQ = 0.4 mM | LOD = 0.01 mM; |
| chloride: | LOQ = 14 µM | LOD = 5 µM |

It is presumed that other excipients have the same or very similar values with regard to LOD and LOQ.

Preferably, the process steps (a) to (d) are performed at room temperature (20-25° C.). A much higher or lower temperature then room temperature should be avoided throughout the whole process due to the temperature sensibility of a number of biomolecules to be used. Temperatures in the range of about 2 to 35° C., preferably about 5 to 25° C., most preferably about 20 to 25° C. are usually acceptable. For example, heating should not be performed at all during the whole process.

Furthermore, it should be noted that the order of sequence in the process is an essential criteria of the present invention and the steps may not be exchanged with each other; otherwise the inventive benefits will not be achieved. Therefore, step (a) is step 1 or the first step to be performed in the process, step (b) is step 2 of the process, step (c) is step 3 of the process and step (d) is step 4 of the process. Another sequence of order is not intended and not desired.

According to another preferred embodiment step (b) and step (c) follow directly one after the other whereby no intermediate process step is performed in between; i.e. diafiltration DF2 follows directly after diafiltration DF1 without any intermediate step in between. Preferably also step (a) and step (b) follow directly one after the other whereby no intermediate process step is performed in between. Preferably also step (c) and step (d) directly follow one after the other whereby no intermediate process step is performed in between. Therefore, the steps (a) to (d) are preferably performed with no intermediate step in between, i.e. step (b) follows directly after step (a), step (c) follows directly after step (c) and step (d) follows directly after step (c).

The invention is also directed to a highly concentrated liquid formulation containing biomolecules prepared by a process as described above.

According to the present invention it is therefore provided a well-defined liquid biomolecule formulation which may be used in the pharmaceutical or non-pharmaceutical field or as a good starting point for the development of pharmaceutical or non-pharmaceutical compositions. The process of the present invention may be used to create a liquid biomolecule formulation to which defined excipients (fourth excipient(s)) may be added back in precise amounts allowing to provide a biomolecule formulation with precise concentrations of contents. These fourth excipient(s) are those already described above or known and described in prior art to be useful in liquid biomolecular formulations.

The advantages of the present invention are manifold:

With the inventive process an improved and modified UF/DF process for preparing clearly defined biomolecule formulations may be provided, preferably clearly defined protein formulations may be obtained.

It has been found that also with regard to problematic high biomolecule concentrations (such as 70 mg/mL or more) the process of the invention is smoothly functioning. The process provides a final formulation consisting or essentially consisting solely of a highly concentrated biomolecule solution and a reduced amount of impurities, i.e. a residue of remaining excipients such as counterions of the biomolecule, if still present.

The process according to the present invention allows the preparation of well-defined highly concentrated formulations containing biomolecules, particularly proteins, intended for pharmaceutical or non-pharmaceutical use. The obtained biomolecule formulation is provided as pure product formulation, which may be purified easier and faster compared with the prior art processes.

Furthermore, the degree of carryover of starting excipients, particularly of anionic excipients like succinate and acetate, present from the initial biomolecule formulation used as starting material is significantly reduced or even minimized.

According to the inventive process the number of diavolume exchanges necessary to clear the starting excipients is in a reasonable range so that biomolecule stability is not affected and aggregate formation not supported.

A further advantage of the process according to the invention is that the process is very mild with regard to physical stress exerted onto the proteins. This can be concluded from a high degree of monomer content which is present throughout the steps of the process.

Since the final product of the process according to the present invention is a clearly defined biomolecule formulation the further processing thereof is more simple and straightforward. In addition tailored formulations may be provided in an easier manner because the user can add the excipients of choice (fourth excipient(s)) by spiking additives to arrive at the desired defined formulation.

The process of the present invention is also feasible in large scale, provides the desired quality standard and operation efficiency with reasonable costs.

Therefore, it is provided an effective UF/DF process which allows the removal of excipients under solution conditions up to very low levels, preferably lower than the level of detection. The inventive UF/DF process may be also used in case of charged excipients and charged biomolecules. For example negatively charged excipients, such as citrate, succinate, and phosphate, may be reduced under solution conditions, to very low levels or levels lower than the detection limit. Preferred charged biomolecules are e.g. proteins, such as antibodies which may be positively charged.

Therefore, the diafiltrations allow users to condition the liquid biomolecule formulation and to replace one solution with another, by removing excipients in form of impurities, for example, remaining from preparation conditions such as fermentation or excipients required for measurement methods such as chromatography.

As a result, the process according to the present invention results in a formulation, achieved with repeated ultrafiltration concentrations and diafiltration washings which have cleared impurities or reduced them to levels that will not affect the safety, efficacy, or storage of the final product.

According to a preferred embodiment the double-diafiltration UF/DF process—incorporating two diafiltration steps, one at high ionic strength and one at low ionic strength (such as pure water)—shows that it is possible to obtain concentrated biomolecule formulations, preferably protein formulations whereby for example, anionic excipients such as phosphate, citrate, succinate, and acetate ions have been fully removed. The preferably produced highly concentrated protein solution is then, for example, composed solely of protein, water and the necessary minimum of a selected counterion, such as chloride, citrate, succinate or acetate forming e.g. a "proteinium-chloride", "proteinium-citrate", "proteinium-succinate" or "proteinium-acetate" complex.

Therefore, it is provided a process which allows to achieve a highly concentrated liquid biomolecule formulation having a defined content.

In order for this invention to be more fully understood, the following examples are set forth. These examples are for the purpose of illustrating embodiments of this invention, and are not to be construed as limiting the scope of the invention in any way.

Practical Implementation

The following are representative examples that illustrate the process of the present invention without limiting it to the specific examples as described.

Materials and Methods

In the examples, embodiments of the process of the present invention were applied to formulations of three test proteins. The proteins were provided with a variety of initial buffer ions such as succinate, citrate, acetate, phosphate. The exchange media was e.g. acetate, chloride, succinate. Final product pools of up to 200 mg/mL protein were produced. The exemplary processes were shown to consistently reduce the levels of residual initial buffer ions below the limit of detection and yielded liquid formulations with only enough exchange-medium counterions to balance the proteins' inherent charge and permit the protein to self-buffer. Protein integrity was assessed by chromatography or opalescence. In general, protein quality (as measured by monomer content) was just slightly reduced or maintained unchanged.

Protein 1 and Protein 2 studied were two humanized monoclonal antibodies, both of isotype IgG and subclass 1. Their average molecular weight was 150 kDa and with an isoelectric point (IP) at approximately pH 8.4 (cf. Karow A. R., Bahrenburg S., & Garidel P. (2013), Buffer capacity of biologics—from buffer salts to buffering by antibodies, Biotechnol. Prog. 29, 480-492). The mAbs were produced by mammalian cell culture in a CHO (Chinese hamster ovary) cell line (see Bergemann K., Eckermann C., Garidel P., Grammatikos S., Jacobi A., Kaufmann H., Kempken R., & Pisch-Heberle S. (2007), Production and Downstream Processing, in: Handbook of Therapeutic Antibodies pp. 199-237, Wiley-VCH Verlag GmbH; Jacobi A., Garidel P., Eckermann C., Knappenberger M., Presser I. & Kaufmann H. (2014), Process Development and Manufacturing of Therapeutic Antibodies, in: Handbook of Therapeutic Antibodies pp. 601-664, Wiley-VCH Verlag GmbH & Co. KGaA). For more details, it is referred to Jacobi, et al. 2014 (loc. cit.) and Garidel P., Kliche W., Pisch-Heberle S., and Thierolf M. (2010), Characterization of proteins and related analytical techniques, in: Protein Pharmaceuticals-Formulation, Analytics & Delivery (Mahler, H. C., Borchard, G., & Lueßen, H., eds.), pp. 44-89, Editio Cantor Verlag, Aulendorf, Germany), the whole disclosures thereof are incorporated by reference in the present disclosure.

Protein 3 studied was a nanobody (see e.g. Gibbs W. W. (2005), Nanobodies, Sci Am. August, 293 (2): 78-83), a trimer with an average molecular weight of 40.7 kDa and an isoelectric point at approximately pH 8.4 (theoretical)/pH 7.5 (experimental). The nanobody was produced via *E. coli* microbial fermentation and is processed and purified accordingly (cf. Arbabi-Ghahroudi M., Tanha J., MacKenzie R. (2005), Prokaryotic expression of antibodies, Cancer Metastasis Rev. December; 24 (4): 501-19; Rahbarizadeh F, Rasaee M J, Forouzandeh-Moghadam M., Allameh A. A. (2005), High expression and purification of the recombinant camelid anti-MUC1 single domain antibodies in *Escherichia coli*, Protein Expr Purif. November, 44(1): 32-8).

Protein 4 is a FC fusion protein, the amino sequence is indicated in example 11. Protein 5 is 100% identical to the published sequence of Rituximab, the heavy chain and light chain is indicated in example 12.

Both sequences are listed as SEQ ID No. 3 ("Artificial Sequence", "FC fusion protein"), SEQ ID No. 4 ("Artificial Sequence", "Rituximab HC"), and SEQ ID No. 5 ("Artificial Sequence", "Rituximab LC") in the accompanying sequence listing.

Various formulations with accepted parenteral excipients were prepared by ultrafiltration and centrifugal filtration (see Pramanick S., Singodia D., & Chandel V. (2013), Excipient selection in parenteral formulation development, Pharma Times 45, 65-77). Specific formulations will be described in the following.

All excipients were of analytical and parenteral grade. Succinic acid, trichloroacetic acid, trisodium citrate dihydrate, acetic acid, and sodium acetate were purchased from Merck KGaA; citrate acid monohydrate from Jungbunzlauer Ladenburg GmbH; disodium succinate hexahydrate and monosodium phosphate from Dr. Paul Lohmann GmbH; disodium phosphate from Chemische Fabrik Budenheim KG; sucrose from Südzucker AG; and sodium chloride from Akzo Nobel.

Protein Analytics

Protein Concentration:

Final protein concentrations of the mAb solutions were determined by spectrophotometry (Lambda 35, Perkin Elmer, Waltham, Mass., USA) via light absorption at $\lambda=280$ nm using mAb-specific extinction coefficients.

pH:

The room temperature pH of the protein solutions at each stage was assessed using a pH meter with coupled pH-electrode (Mettler Toledo SevenGo, Columbus, Ohio, USA). Before each pH measurement, it was carried out a two-point calibration with calibration solutions at pH 4 and pH 7 (Mettler Toledo SevenGo, Columbus, Ohio, USA).

Osmolality:

Osmolality was determined using a freezing-point osmometer (Osmomat 030, Gonotec, Berlin, Germany).

Protein Integrity:

The investigation of protein quality focused on particle formation, as indicated by visual inspection, opalescence, and high-performance size-exclusion liquid chromatography (HP-SEC) (Garidel et al. 2010, loc.cit.; den Engelsman J., Garidel P., Smulders R., Koll H., Smith B., Bassarab S., Seidl A., Hainzl O., & Jiskoot W. (2011), Strategies for the Assessment of Protein Aggregates in Pharmaceutical Biotech Product Development, Pharm Res 28, 920-933).

Visual Inspection:

Visual inspection was performed according to the current Pharmacopeia.

Opalescence:

Opalescence may indicate protein particle formation (Sukumar M., Doyle B. L., Combs J. L., & Pekar A. H. (2004), Opalescent appearance of an IgG1 antibody at high concentrations and its relationship to noncovalent association, Pharmaceutical Research 21, 1087-1093). An increase in opalescence is mostly linked to an increase in protein aggregation or particle concentration. Opalescence is measured in formazine nephelometric units (FNU) via photometry of 90°—scattered light at 400-600 nm. The photometer (2100AN Laboratory Turbidimeter, Hach, Loveland, Colo., USA) was initially calibrated with standards for 20 and 100 FNU, according to the European Pharmacopoeia (2013).

High-Performance Size-Exclusion Liquid Chromatography (HP-SEC):

Monomer content and levels of protein aggregates (dimers and higher species) were determined via size-exclusion chromatography (Acquity HClass and TUV detector, both from Waters Corporation, Milford, Mass., USA; columns were Waters Acquity UPLC 4.6 mm×300 mm analytical column, also from Waters Corporation, Milford, Mass., USA). The mobile phase was 200 mM L-arginine, 120 mM ammonium sulfate, and 10% isopropyl alcohol adjusted with 85% phosphoric acid to pH 7.3. The HP-SEC was performed at room temperature.

All samples were diluted to a final concentration of 5 mg/mL and an injection volume of 5 µL is injected with an isocratic flow of 0.2 mL/min. The resulting peaks, detected by absorbance at $\lambda=280$ nm by UV detector, showed the amounts of dimer and higher-order aggregates; percentage of remaining monomer was calculated.

Strong Cation Exchange Chromatography (SCX) (Corresponds to IEC Ionic Exchange Chromatography):

Analytical strong cation exchange chromatography (SCX) was used for separation and quantification of charge variants of protein 3 8prot 3). A MabPac® SCX-10 column (4×250 mm, 10 µm, Thermo Scientific 074625) was used on an Alliance HPLC-System (Waters) coupled with a UV-detector. The column was tempered to 35° C. The separated peaks were detected at an absorbance of 280 nm. Elution was caused by a gradient from 100% to 64% buffer A (10 mM $Na_2HPO_4$ with pH 7.0) in 22 minutes with a constant flow of 1 $mL*min^{-1}$. The column regeneration was caused by 100% buffer B (10 mM $Na_2HPO_4$, 1 M NaCl, pH 7) for 4 minutes at a constant flow of 1 $mL*min^{-1}$. Protein 3 was diluted with water to a concentration of 0.2 $mg*mL^{-1}$. 40 µL of the diluted protein was injected. Buffer A contained 10 mM $Na_2HPO_4$ with pH 7.0

Excipient Analytics

Carboxylic Acid Analytics (Succinate, Citrate, Acetate):

Residual excipient was determined by high pressure liquid chromatographic analysis (Äkta Micro, GE Healthcare, Little Chalfont, UK; Acclaim Organic Acid Column, 5 µm 4.0×250 mm, Thermo Fischer, Waltham, Mass., USA). The mobile phase was 100 mM sodium sulfate adjusted to pH 2.6 with 99% methane sulfonic acid. The column temperature was set to 30° C. by a column heater. Injection volume was 10 µL, and an isocratic elution with a flow rate of 0.6 mL/min was applied. Carboxyl group concentrations were measured by UV-Vis detector tuned to 210 nm. Because proteins interfere with measurements at this wavelength, the mAb was first precipitated with TCA (trichloro acetic acid) (10%) in a ratio of 3:1 (sample/TCA, V/V). A calibration curve was generated and used to determine the residual excipient levels.

The protein precipitation increases the solution's excluded volume, and this must be considered when calculating excipient concentrations. When the protein concentration is very high, these deviations can run as 15% (200 mg/mL). The limit of quantification (LOQ) and limit of detection (LOD) are: acetate LOQ=0.7 mM & LOD=0.1 mM, citrate LOQ=0.1 mM & LOD=0.01 mM, succinat LOQ=0.4 mM & LOD=0.01 mM.

Chloride and Phosphate:

Ion-specific cuvette kits (LCK 311 for chloride, LCK 350 for phosphate, Hach, Salford, UK) were used to determine chloride and phosphate concentrations. The cuvettes contain pre-dosed reagents with defined concentrations. Sample preparation included a TCA protein precipitation identical to that employed in the carboxylic acid analysis, and for the same reason: proteins would precipitate with reagents in the cuvettes and would interfere photometric evaluation.

The LCK311 test measures chloride concentrations in two ranges: 1-70 mg/L (I) and 70-1000 mg/L (II). Testing in the lower-concentration 1-70 mg/L uses a 1 mL sample volume; testing in the 70-1000 mg/L range uses a 0.1 mL sample. The sample is added to the cuvette, which is then shaken, held for 3 minutes, and then analysed with a spectral photometer (DR 3900, Hach, Salford, UK). The chloride LOQ=14 µM & LOD=5 µM.

The LCK349 test for phosphate determines ion concentration in the 2-20 mg/L range. In the analysis, 0.4 mL of sample is added to the cuvette, followed by 0.5 mL of the Solution B provided with the kit. The cuvette is then sealed with a DosiCap C. The phospate LOQ=0.05 mg/L, according to the present invention. After shaking and a hold time of 10 minutes, the samples were analysed with by spectral photometer (DR 3900, Hach, Salford, UK).

Conditioning and Preparation of Defined Protein Solutions Ultrafiltration/Diafiltration (UF/DF) Process:

A defined protein solution, with mAb concentrations up to 160 mg/mL, was prepared and conditioned using a UF/DF system according to the present invention having the four steps:

step (a): UF1, ultrafiltration to concentrate the protein solution to 25%-50% of target;

step (b) DF1, diafiltration against a buffer medium (medium B of high ionic strength and therefore high conductivity);

step (c) DF2, diafiltration against water (medium C of low ionic strength and therefore low conductivity); and step (d) UF2, ultrafiltration to concentrate the protein to the desired value.

It was used a polyethersulfone membrane, Centramate T-Series, having a cutoff of 30 kDa, A=200 $cm^2$ (membrane area) (Pall, New York, USA). The flow rate was below 0.8 $mL \cdot min^{-1} \cdot cm^{-2}$.

The UF/DF was run under the following conditions: inlet pressure=1.5 bar; outlet pressure=0.5 bar; and a transmembrane pressure of ~1 bar.

The number of exchange volumes or exchange cycles depended on the diafiltration medium used.

Excipient analyses were performed at each stage to monitor changes in solution conditions.

Centrifugal Filtration:

A second embodiment was tested to exchange the starting buffer and concentrate the protein solution. A centrifugal filtration system (regenerated cellulose, Amicon Ultra 15 mL Centrifugal Filter, Merck Millipore, Billerica, Mass., USA) was used for a Protein 3 nanobody. The process conditions were similar to those used in the UF/DF process for the Protein 1 and Protein 2 mAbs.

BRIEF DESCRIPTION OF THE DRAWINGS

The detailed process description of the experiments is given in connection with the attached drawings which are incorporated in and constitute a part of the specification, illustrating preferred embodiments of the invention without limitation to the specific embodiments described. The Drawings together with the general description and detailed description serve to explain the principles of the present invention. The drawings show as follows FIG. 1A a schematic representation of a diafiltration (DF) step;

FIGS. 1A, 1B, 2 and 3 have been already described. The examples according to the present invention are explained in connection with the FIGS. 4A to 15 in the following:

EXAMPLES

In all examples the water used is MilliQ® water.

The symbol "~" followed by a number shall be understood in that the number has been rounded up to the nearest whole number.

Example 1

-Succinate-Acetate Exchange-

According to example 1 an embodiment of the 4-step UF/DF process according to the present invention was applied to concentrate a protein and replace initial succinate buffer ions with low levels of acetate. Thus, a "proteinium-acetate" formulation is generated, with acetate as counterion.

The used biomolecule (designated as "Prot1" hereafter) was a monoclonal antibody comprising this heavy chain (amino acid single letter code, N to C-terminus):

QVQLVQSGAEVKKPGSSVKVSCKASGYTFTDQTIHWMRQAPGQGLEWIGY

IYPRDDSPKYNENFKGKVTITADKSTSTAYMELSSLRSEDTAVYYCAIPD

RSGYAWFIYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPEAAGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG and this light chain (amino acid single letter code, N to C-terminus):

DIQMTQSPSSLSASVGDRVTITCKASRDVAIAVAWYQQKPGKVPKLLIYW

ASTRHTGVPSRFSGSGSRTDFTLTISSLQPEDVADYFCHQYSSYPFTFGS

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Both sequences are listed as SEQ ID NO. 1 ("Artificial Sequence", "monoclonal antibody, heavy chain") and SEQ ID NO. 2 ("Artificial Sequence", "monoclonal antibody, light chain") in the accompanying sequence listing.

The detailed conditions of example 1 were as follows:
UF1: 10 mg·ml$^{-1}$ Prot1/25 mM Succinate/125 mM NaCl/water/pH 6.5;
DF1: 4 cycles with 500 mM Acetate/water/pH 5.0;
DF2: 6 cycles with water;
UF2 (Product Pool): 150 mg·ml$^{-1}$ Prot1/26 mM Acetate/water/pH 5.9.

Therefore, in example 1, the starting solution is 10 mg/mL Protein 1 mAb in ultrapure water which contains 25 mM sodium succinate and 125 mM sodium chloride at pH 6.5.

Figure 4A:
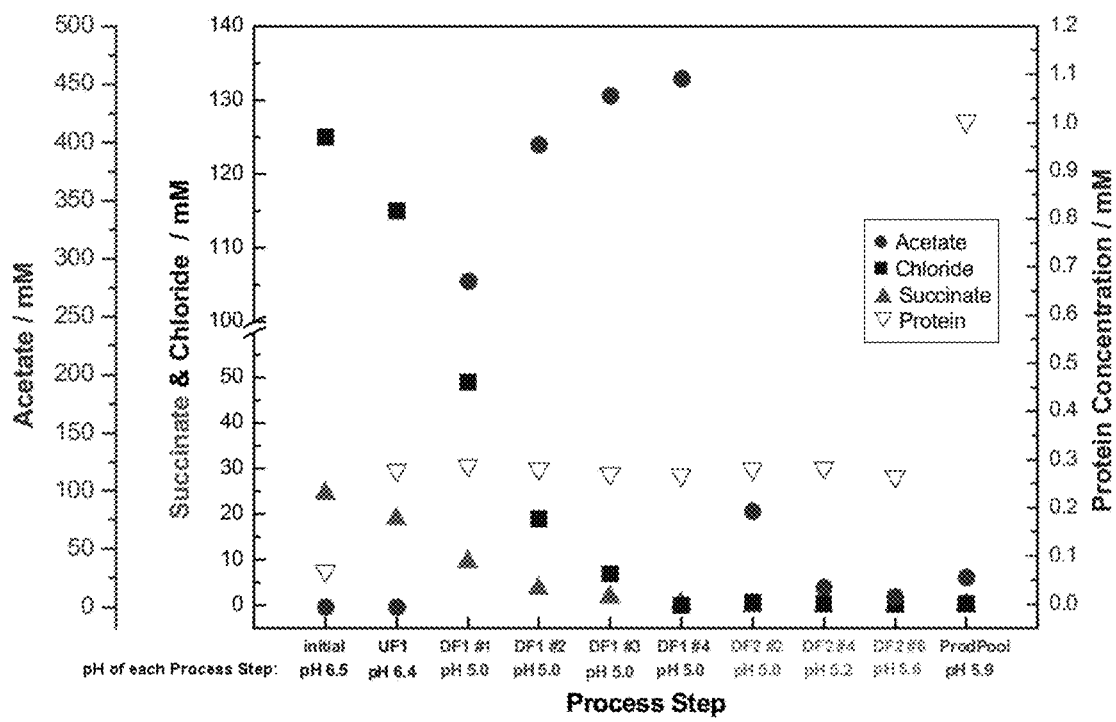
FIG. 4A a diagram of an exemplary embodiment of the ultrafiltration/diafiltration (UF/DF) process according to the present invention: the excipient and protein concentrations during the UF/DF-process of protein 1 (Prot1) (y axis) are plotted against the pH value in each process step (step (a) to step (d)) (x axis) in a succinate-acetate exchange.

FIG. 4A shows the results of the succinate-acetate exchange according to example 1. On the y axis the excipient and protein concentrations during the UF/DF-process of protein 1 (Prot1) are entered, the UF/DF-process including a diafiltration step with 4 cycles of 500 mM sodium acetate pH 5.0 (DF1) followed by 6 cycles of diafiltration with ultrapure water of type 1 (e.g. MilliQ® water of Merck Millipore) (pH 6) (DF2) to provide an entire exchange of the excipients from the initial solution towards the anion component (acetate) of DF1.

The x axis coordinates the process steps and the corresponding pH. The respective points on the x axis are: initial, end of UF1, cycle #1/#2/#3/#4 of DF1, cycle #2/#4/#6 of DF2 and the final product (ProdPool) at the end of UF2.

Figure 4B:
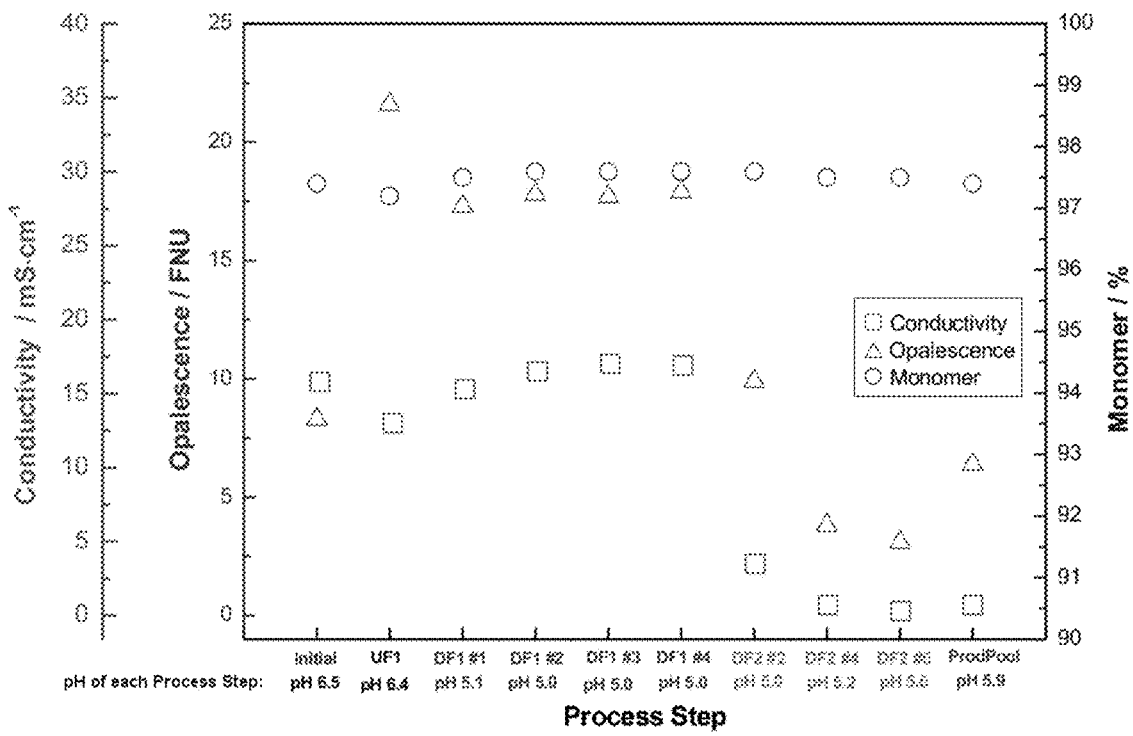
FIG. 4B a diagram wherein conductivity, opalescence and monomer content during the UF/DF-process of protein 1 (Prot1) (y axis) of FIG. 4A are plotted against the pH value in each process step (step (a) to step (d)) (x axis) in a succinate-acetate exchange.

FIG. 4B shows the results of the conductivity, opalescence and monomer content of the succinate-acetate exchange of example 1.

As can be seen from FIG. 4A, the initial, measured chloride concentration is 125 mM and succinate concentration is 25 mM. UF1 concentrates the protein to ~40 mg/mL. DF1 consists of four cycles of diafiltration against 500 mM sodium acetate at pH 5.0 to reduce succinate levels to 0.5 mM and chloride concentration below the detection limit. Increasing the number of diafiltration cycles would further reduce succinate concentration, but at the expense of process time and potential protein stress.

In DF2, six cycles of diafiltration against pure water at pH 6 then remove the last traces of succinate while greatly reducing the residual DF1 acetate, which falls to ~9 mM.

Complete removal of acetate is neither possible nor advisable. At the tested pH conditions, Protein 1 is positively charged; the residual acetate anions function as counterions, at an acetate/Protein 1 ratio of ~30:1 at the end of DF2.

UF2 follows, concentrating Protein 1 to ≥150 mg/mL. With this volume reduction, acetate concentration increases to ~26 mM. The resulting acetate/protein ratio is ~26:1, very close to the level for the 40 mg/mL Protein 1 solution at the end of DF2: this is the proportion of acetate counterions required to maintain the system's charge neutrality. The observed difference between 30:1 (after DF2) and 26:1 (after UF2) may be attributed to minor errors in measuring anion and/or protein concentrations.

At this stage, the product pool (final product) is 150 mg/mL Protein 1 mAb at pH 5.9 with ~20 mM acetate serving as counterions. Therefore, the pH of the product pool is determined and maintained by the protein's own self-buffering capacity and the counterion (Karow et al. 2013, loc.cit.).

Product quality is monitored via opalescence and HP-SEC monomer content.

Conductivity is used for process control. As expected, after DF2, conductivity decreases from 15 millisiemens per centimetre (mS·cm$^{-1}$) to close to 1 mS·cm$^{-1}$. During UF1, opalescence increases from 8 FNU at 10 mg/mL to more than 20 FNU at 40 mg/mL in the presence of succinate. Exchanging succinate for acetate in DF1 reduces opalescence to ~17 FNU. Removing acetate during DF2 further reduces opalescence to 3-4 FNU. After the final concentration of Protein 1 in UF2, opalescence increases again, but only to 6-7 FNU (cf. FIG. 4B). The protein's initial monomer content is 97.5% and remains more or less constant throughout the process.

FIG. 4B illustrates the good product quality with regard to the high degree of monomer content throughout the steps of the process.

Example 2

-Succinate-Acetate Exchange with Changed pH in DF1-

According to example 2 an embodiment of the 4-step UF/DF process according to the present invention was applied to concentrate a protein and replace initial succinate buffer ions with low levels of acetate, wherein the pH in the DF1 step was changed.

The detailed conditions of example 2 were as follows:
UF1: 10 mg·ml$^{-1}$ Prot1/25 mM Succinate/125 mM NaCl/water/pH 6.5;
DF1: 4 cycles with 500 mM Acetate/water/pH 6.0;
DF2: 6 cycles with water;
UF2 (Product Pool): 138 mg·ml$^{-1}$ Prot1/20 mM Acetate/water/pH 6.4.

Figure 5A:
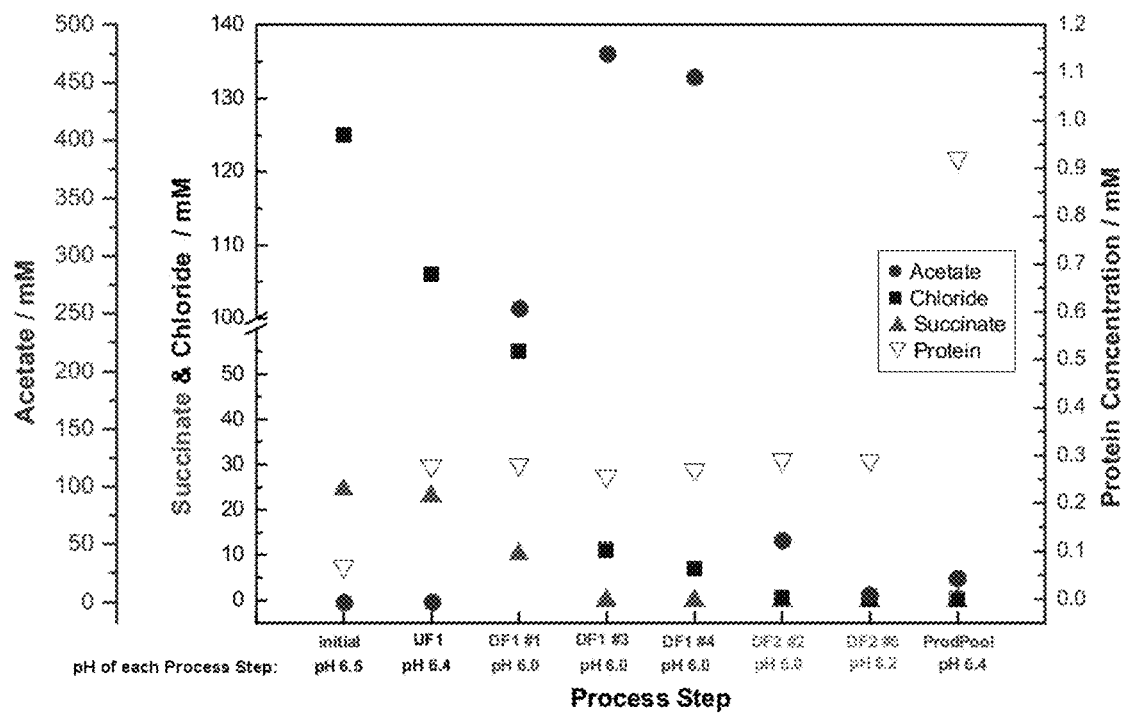
FIG. 5A a diagram of an exemplary embodiment of the ultrafiltration/diafiltration (UF/DF) process according to the present invention: the excipient and protein concentrations during the UF/DF-process of protein 1 (Prot1) (y axis) are plotted against the pH value in each process step (step (a) to step (d)) (x axis) in a succinate-acetate exchange.

FIG. 5A shows the results of the succinate-acetate exchange at higher pH according to example 2. On the y axis the excipient and protein concentrations during the UF/DF-process of protein 1 (Prot1) are entered, the UF/DF-process including a diafiltration step with 4 cycles of 500 mM sodium acetate pH 6.0 (DF1) followed by 6 cycles of diafiltration with ultrapure water of type 1 (e.g. MilliQ® water of Merck Millipore) (pH 6) (DF2) to provide an entire exchange of the excipients from the initial solution towards the anion component (acetate) of DF1. The concentration of the anion is dependent on the amount of the positive net charge of the protein, which is mainly influenced by the pH and the concentration of the protein.

The x axis coordinates the process steps and the corresponding pH. The respective points on the x axis are: initial, end of UF1, cycle #1/#3/#4 of DF1, cycle #2/#6 of DF2 and the final product (ProdPool) at the end of UF2.

Figure 5B:
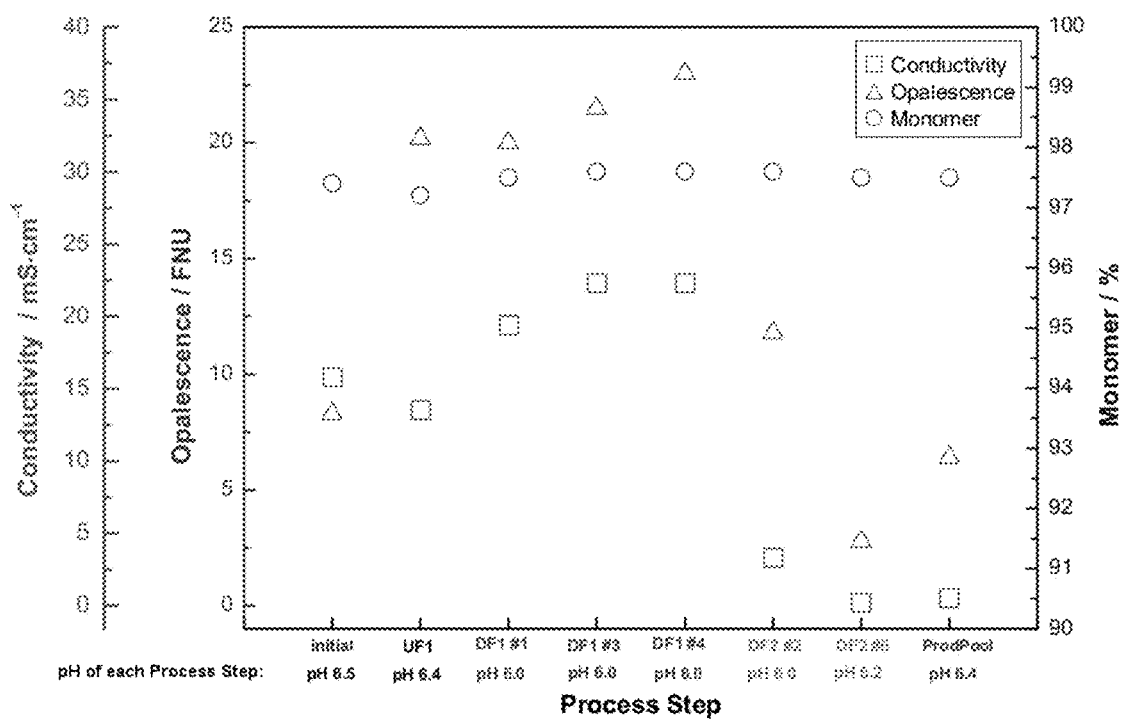
FIG. 5B a diagram wherein conductivity, opalescence and monomer content during the UF/DF-process of protein 1 (Prot1) (y axis) of FIG. 5A are plotted against the pH value in each process step (step (a) to step (d)) (x axis) in a succinate-acetate exchange.

FIG. 5B shows the results of the conductivity, opalescence and monomer content of the succinate-acetate exchange of example 2.

This embodiment of the four-step UF/DF process of example 1 was repeated but with a change in the DF1 step, i.e. diafiltering against 500 mM sodium acetate at pH 6 rather than pH 5 (FIG. 5A). Comparing FIGS. 4A and 5A shows that succinate clearance reaches similar values in both examples. In example 2, the final product pool is 138 mg/mL Protein 1 at pH 6.4 with ~20 mM acetate as counterions (acetate/protein ratio 22:1) and no detectable succinate.

The one-unit increase to pH 6 in DF1 leads to slightly higher opalescence than in example 1. The monomer content remains unchanged throughout, at the same level as in example 1 (FIG. 5B).

FIG. 5B also illustrates the good product quality with regard to the high degree of monomer content throughout the steps of the process.

Example 3

-Citrate-Chloride Exchange-

According to example 3 an embodiment of the 4-step UF/DF process according to the present invention was applied to concentrate a protein and replace initial citrate buffer ions with chloride.

The detailed conditions of example 3 were as follows:
UF1: 10 mg ml$^{-1}$ Prot1/48 mM Citrate/water/pH 6.1;
DF1: 4 cycles with 500 mM Sodium Chloride/water/pH 6.0;
DF2: 6 cycles with water;
UF2 (Product Pool): 144 mg·ml$^{-1}$ Prot1/20 mM Chloride/water/pH 5.8.

Figure 6A:
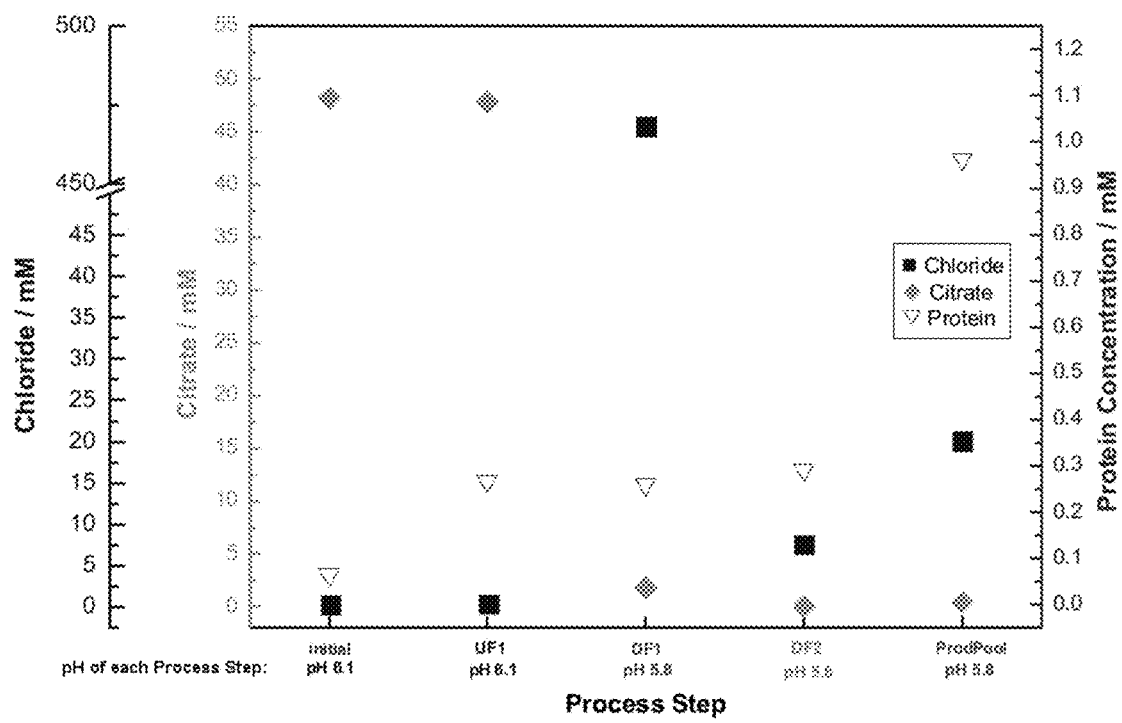
FIG. 6A a diagram of an exemplary embodiment of the ultrafiltration/diafiltration (UF/DF) process according to the present invention: the excipient and protein concentrations during the UF/DF-process of protein 1 (Prot1) (y axis) are plotted against the pH value in each process step (step (a) to step (d)) (x axis) in a citrate-chloride exchange.

FIG. 6A shows the results of the citrate-chloride exchange according to example 3. On the y axis the excipient and protein concentrations during the UF/DF-process of protein 1 (Prot1) are entered, the UF/DF-process including a diafiltration step with 4 cycles of 500 mM NaCl pH 6.0 (DF1) followed by 6 cycles of diafiltration with ultrapure water of type 1 (e.g. MilliQ® water of Merck Millipore) (pH 6) (DF2) to provide an entire exchange of the excipients from the initial solution towards the anion component (chloride) of DF1.

The x axis coordinates the process steps and the corresponding pH. The respective points on the x axis are: initial, end of UF1, end of DF1, end of DF2 and the final product (ProdPool) at the end of UF2.

Figure 6B:
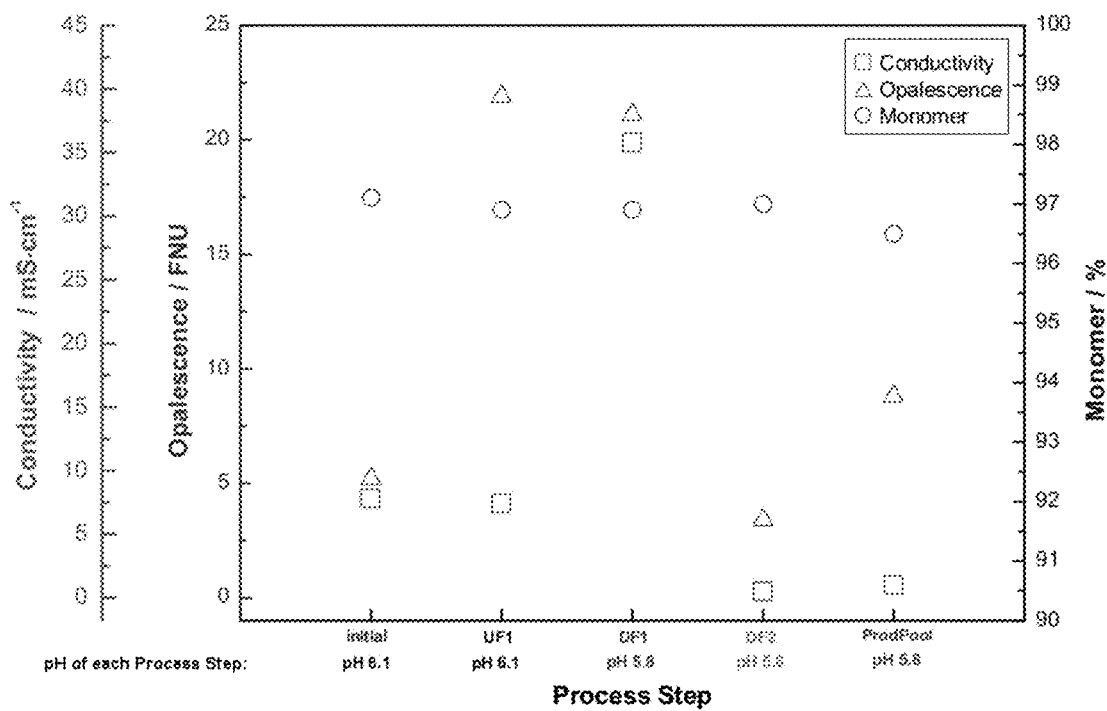
FIG. 6B a diagram wherein conductivity, opalescence and monomer content during the UF/DF-process of protein 1 (Prot1) (y axis) of FIG. 6A are plotted against the pH value in each process step (step (a) to step (d)) (x axis) in a citrate-chloride exchange.

FIG. 6B shows the results of the conductivity, opalescence and monomer content of the citrate-chloride exchange of example 3.

In example 3, citrate was cleared and exchanged for chloride (FIG. 6A). The initial protein solution is composed of 10 mg/mL Protein 1 mAb with 48 mM sodium citrate without additional salt at pH 6.5 (FIG. 6A).

After UF1 concentrated the protein to 40 mg/mL mAb, DF1 is run against 500 mM sodium chloride at pH 6.0. After 4 diafiltration cycles, citrate concentration is reduced to 2 mM.

Six DF2 diafiltration cycles against pure water at pH 6 are then sufficient to fully remove all citrate. With the current process it is thus possible to fully reduce citrate without resorting to 20, 30, or 40 diafiltration cycles that might damage the protein.

The final product pool is 144 mg/mL Protein 1 at pH 5.8 with 20 mM chloride anions as counterions (FIG. 6A), at a chloride/protein ratio of 21:1 to 26:1.

The indices of product quality (FIG. 6B) show a small (0.4%) decrease in monomer content over the course of the four steps. Such decreases are not unusual when proteins are concentrated to the 100 mg/mL level. The degree depends on the target protein concentration, the protein's sensitivity to the shear stresses of UF/DF, the buffer, and process conditions (e.g. membrane material, transmembrane pressure, and flux).

FIG. 6B also illustrates the good product quality with regard to the high degree of monomer content throughout the steps of the process.

Example 4

-Citrate-Acetate Exchange-

According to example 4 an embodiment of the 4-step UF/DF process according to the present invention was applied to concentrate a protein and replace initial citrate buffer ions with acetate.

The detailed conditions of example 4 were as follows:
UF1: 10 mg ml$^{-1}$ Prot1/48 mM Citrate/water/pH 6.1;
DF1: 4 cycles with 500 mM Acetate/water/pH 6.0;
DF2: 6 cycles with water;
UF2 (Product Pool): 160 mg·ml$^{-1}$ Prot1/23 mM Acetate/water/pH 6.4.

Figure 7A:
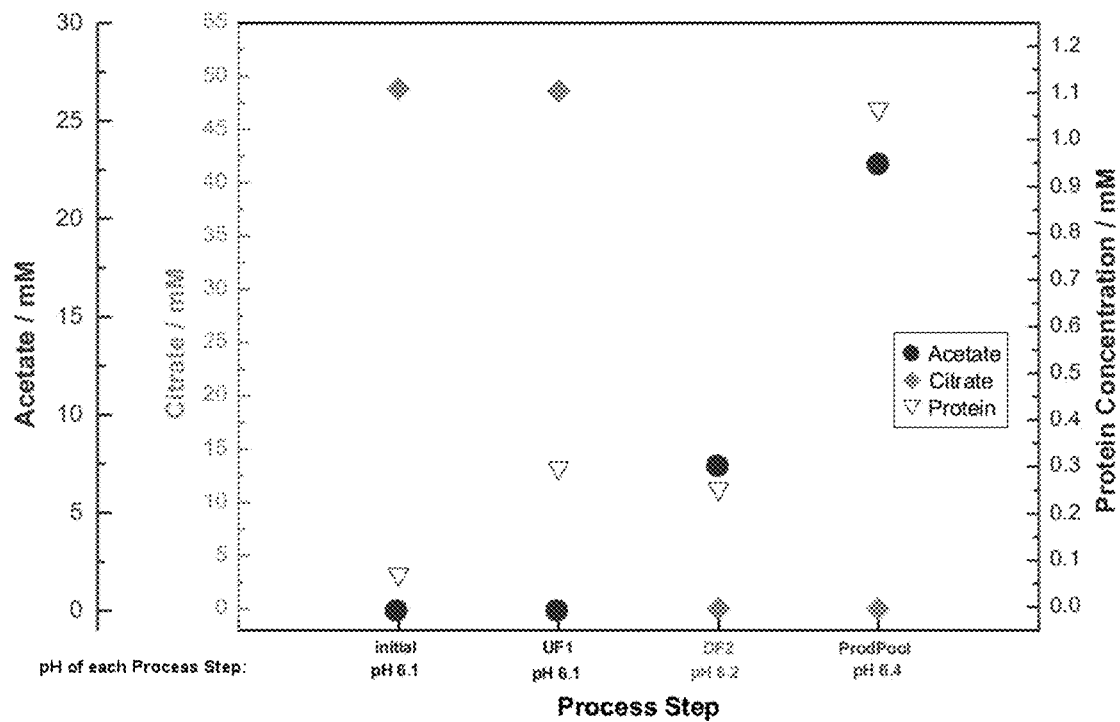
FIG. 7A a diagram of an exemplary embodiment of the ultrafiltration/diafiltration (UF/DF) process according to the present invention: the excipient and protein concentrations during the UF/DF-process of protein 1 (Prot1) (y axis) are plotted against the pH value in each process step (step (a) to step (d)) (x axis) in a citrate-acetate exchange.

FIG. 7A shows the results of the citrate-acetate exchange according to example 4. On the y axis the excipient and protein concentrations during the UF/DF-process of protein 1 (Prot1) are entered, the UF/DF-process including a diafiltration step with 4 cycles of 500 mM sodium acetate pH 6.0 (DF1) followed by 6 cycles of diafiltration with ultrapure water of type 1 (e.g. MilliQ® water of Merck Millipore) (pH 6) (DF2) to provide an entire exchange of the excipients from the initial solution towards the anion component (acetate) of DF1.

The x axis coordinates the process steps and the corresponding pH. The respective points on the x axis are: initial, end of UF1, end of DF2, and the final product (ProdPool) at the end of UF2.

Figure 7B:
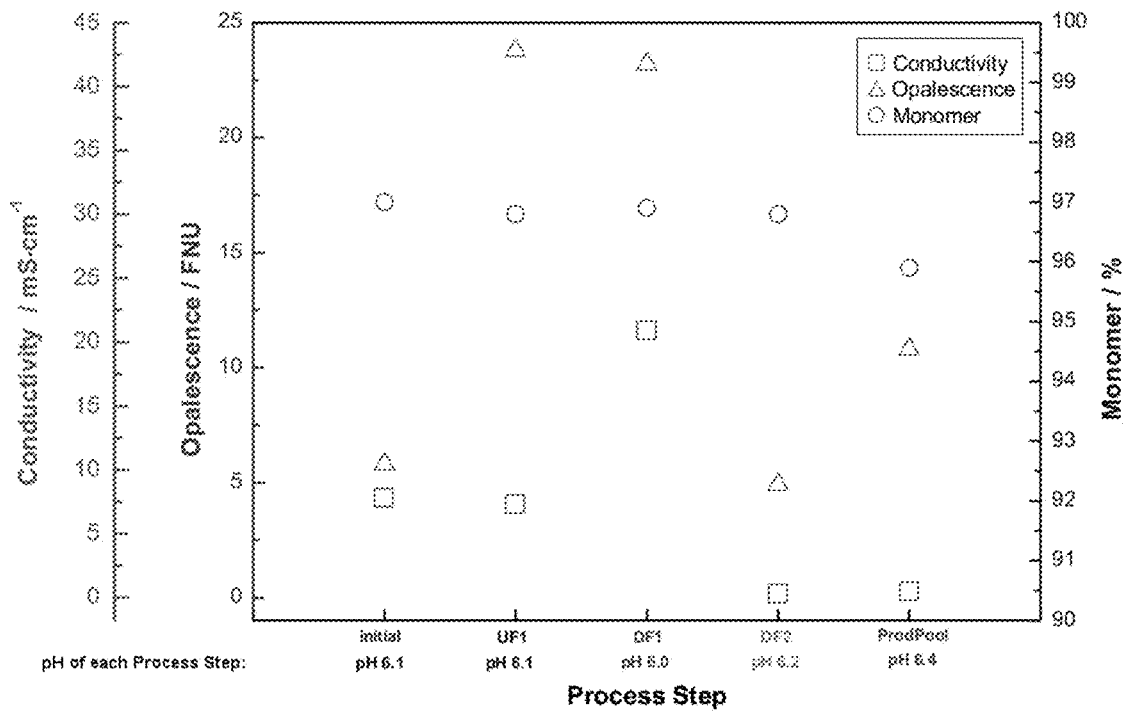
FIG. 7B a diagram wherein conductivity, opalescence and monomer content during the UF/DF-process of protein 1 (Prot1) (y axis) of FIG. 7A are plotted against the pH value in each process step (step (a) to step (d)) (x axis) in a citrate-acetate exchange.

FIG. 7B shows the results of the conductivity, opalescence and monomer content of the citrate-acetate exchange of example 4.

In example 4, the initial citrate buffer is exchanged for acetate and cleared (FIG. 7A). The initial solution is 10 mg/mL Protein 1 with 48 mM sodium citrate at pH 6.1.

In DF1, 40 mg/mL protein solution is diafiltered against 500 mM sodium acetate at pH 6.0. The citrate is easily removed, falling below the detection limit after six DF2 cycles. And after UF2, the final product pool is 160 mg/mL Protein 1 at pH 6.4 with 23 mM acetate counterions (for an acetate/protein ratio of about 22:1).

Under these UF/DF buffer conditions, monomer content decreased by about 0.9% from initial solution to final product pool (FIG. 7B). However, it would be readily possible to optimise this process variant in view of product quality so that the monomer content is only slightly reduced or maintained unchanged.

FIG. 7B also illustrates the good product quality with regard to the high degree of monomer content throughout the steps of the process.

Example 5

-Succinate-Chloride Exchange-

According to example 5 an embodiment of the 4-step UF/DF process according to the present invention was applied to concentrate a protein and replace initial succinate buffer ions with chloride.

The detailed conditions of example 5 were as follows:
UF1: 10 mg·ml$^{-1}$ Prot1/25 mM Succinate/125 mM NaCl/water/pH 6.5;
DF1: 4 cycles with 500 mM NaCl/water/pH 6.2;
DF2: 6 cycles with water;
UF2 (Product Pool): 157 mg ml$^{-1}$ Prot1/18 mM Chloride/water/pH 6.4.

Figure 8:
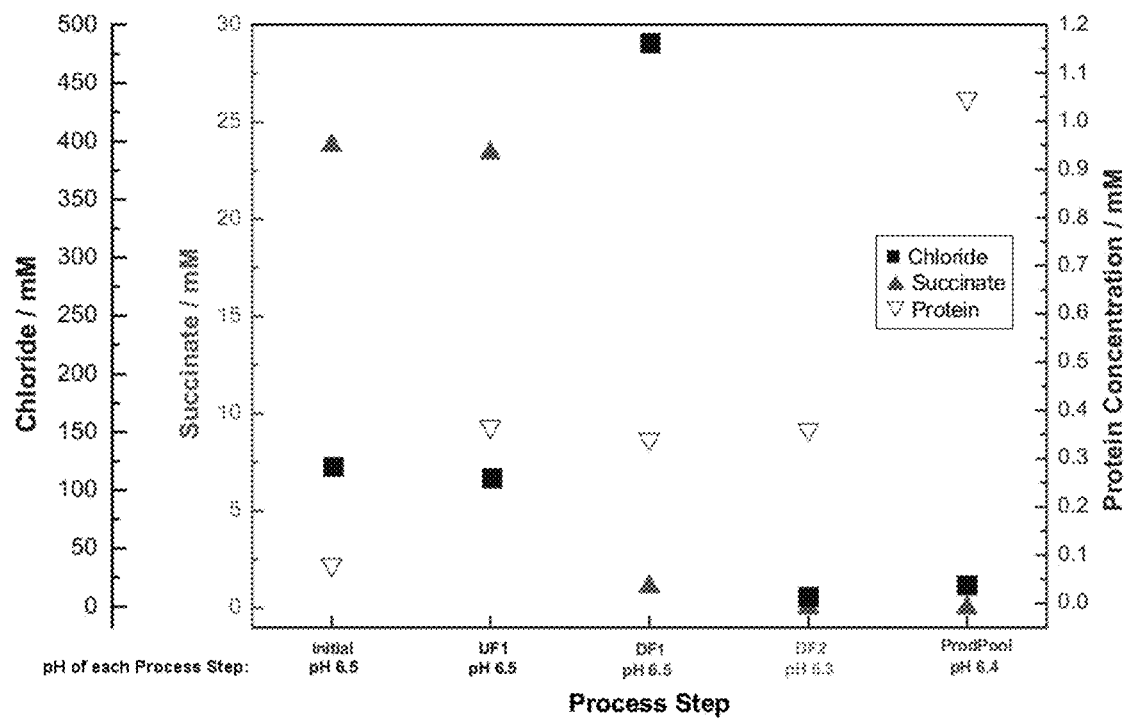
FIG. 8 a diagram of an exemplary embodiment of the ultrafiltration/diafiltration (UF/DF) process according to the present invention: the excipient and protein concentrations during the UF/DF-process of protein 1 (Prot1) (y axis) are plotted against the pH value in each process step (step (a) to step (d)) (x axis) in a succinate-chloride exchange.

FIG. 8 shows the results of the succinate-chloride exchange according to example 5. On the y axis the excipient and protein concentrations during the UF/DF-process of protein 1 (Prot1) are entered, the UF/DF-process including a diafiltration step with 4 cycles of 500 mM NaCl pH 6.2 (DF1) followed by 6 cycles of diafiltration with ultrapure water of type 1 (e.g. MilliQ® water of Merck Millipore) (pH 6) (DF2) to provide an entire exchange of the excipients from the initial solution towards the anion component (chloride) of DF1. The concentration of the anion is dependent on the amount of the positive net charge of the protein, which is mainly influenced by the pH and the concentration of the protein.

The x axis coordinates the process steps and the corresponding pH. The respective points on the x axis are: initial, end of UF1, end of DF1, end of DF2 and the final product (ProdPool) at the end of UF2.

Example 6

-Acetate-Chloride Exchange-

According to example 6 an embodiment of the 4-step UF/DF process according to the present invention was applied to concentrate a protein and replace initial acetate buffer ions with chloride.

The detailed conditions of example 6 were as follows:
UF1: 11 mg·ml$^{-1}$ Prot1/139 mM Acetate/150 mM NaCl/water/pH 5.8;
DF1: 4 cycles with 500 mM NaCl/water/pH 6.0;
DF2: 6 cycles with water;
UF2 (Product Pool): 157 mg·ml$^{-1}$ Prot1/23 mM Chloride/water/pH 5.7.

Figure 9:
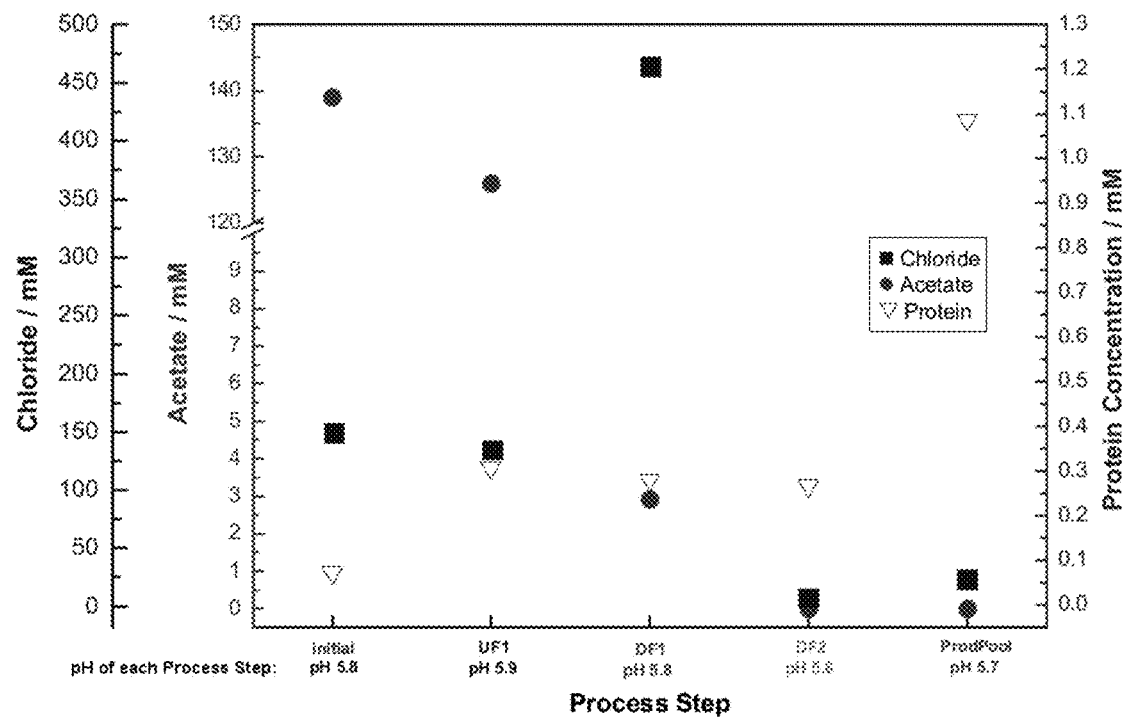
FIG. 9 a diagram of an exemplary embodiment of the ultrafiltration/diafiltration (UF/DF) process according to the present invention: the excipient and protein concentrations during the UF/DF-process of protein 1 (Prot1) (y axis) are plotted against the pH value in each process step (step (a) to step (d)) (x axis) in an acetate-chloride exchange.

FIG. 9 shows the results of the acetate-chloride exchange according to example 6. On the y axis the excipient and protein concentrations during the UF/DF-process of protein 1 (Prot1) are entered, the UF/DF-process including a diafiltration step with 4 cycles of 500 mM NaCl pH 6.0 (DF1) followed by 6 cycles of diafiltration with ultrapure water of type 1 (e.g. MilliQ® water of Merck Millipore) (pH 6) (DF2) to provide an entire exchange of the excipients from the initial solution towards the anion component (chloride) of DF1. The concentration of the anion is dependent on the amount of the positive net charge of the protein, which is mainly influenced by the pH and the concentration of the protein.

The x axis coordinates the process steps and the corresponding pH. The respective points on the x axis are: initial, end of UF1, end of DF1, end of DF2, and the final product (ProdPool) at the end of UF2.

In the examples 5 and 6 the exchange of chloride for succinate (FIG. 8) and chloride for acetate (FIG. 9) were evaluated. In each case, DF1 is run for four cycles against 500 mM sodium chloride, followed by six DF2 cycles against pure water. In both cases, the initial buffer ion is fully removed and the product pool is 157 mg/mL Protein 1, with a chloride/Protein 1 ratio of about 20:1. The indices of product quality were within expected ranges and were not impaired by the process (data not shown).

Example 7

-Phosphate-Succinate Exchange-

According to example 7 an embodiment of the 4-step UF/DF process according to the present invention was applied to concentrate a protein and replace initial phosphate buffer ions with succinate.

Figure 10A:
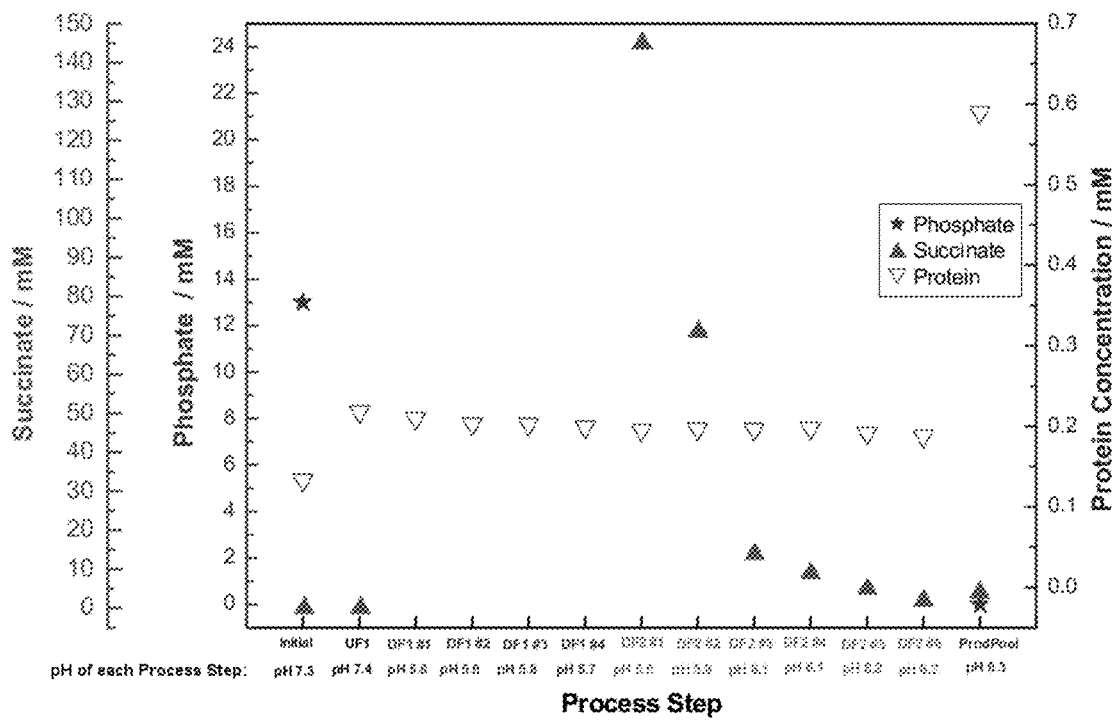
FIG. 10A a diagram of an exemplary embodiment of the ultrafiltration/diafiltration (UF/DF) process according to the present invention: the excipient and protein concentrations during the UF/DF-process of protein 2 (Prot2) (y axis) are plotted against the pH value in each process step (step (a) to step (d)) (x axis) in a phosphate-succinate exchange.
Figure 10B:
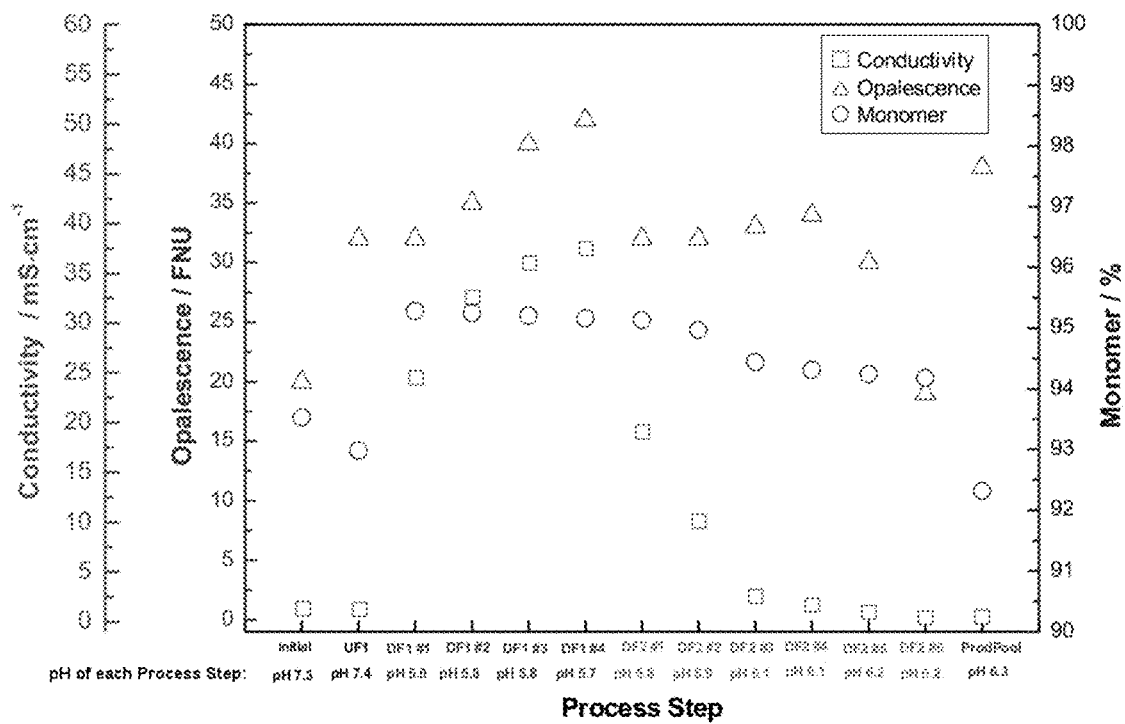
FIG. 10B a diagram wherein conductivity, opalescence and monomer content during the UF/DF-process of protein 2 (Prot2) (y axis) of FIG. 10A are plotted against the pH value in each process step (step (a) to step (d)) (x axis) in a phosphate-succinate exchange.

A second antibody, the IgG1 mAb Protein 2, was tested to investigate double-diafiltration UF/DF performance with another protein (FIGS. 10A and 10B).

The detailed conditions of example 7 were as follows:
UF1: 20 mg ml$^{-1}$ Prot2/13 mM Phosphate/146 mM Sucrose/water/pH 7.3;
DF1: 4 cycles with 500 mM Succinate/water/pH 5.7;
DF2: 6 cycles with water;
UF2 (Product Pool): 89 mg ml$^{-1}$ Prot2/4 mM Succinate/water/pH 6.3.

FIG. 10A shows the results of the phosphate-succinate exchange according to example 7. On the y axis the excipient and protein concentrations during the UF/DF-process of protein 2 (Prot2) are entered, the UF/DF-process including a diafiltration step with 4 cycles of 500 mM sodium succinate pH 5.7 (DF1) followed by 6 cycles of diafiltration with ultrapure water of type 1 (e.g. MilliQ® water of Merck Millipore) (pH 6) (DF2) to provide an entire exchange of the excipients from the initial solution towards the anion component (succinate) of DF1.

The x axis coordinates the process steps and the corresponding pH. The respective points on the x axis are: initial, end of UF1, cycle #1/#2/#3/#4 of DF1, cycle #1/#2/#3/#4/#5/#6 of DF2 and the final product (ProdPool) at the end of UF2.

FIG. 10B shows the results of the conductivity, opalescence and monomer content of the phosphate-succinate exchange of example 7.

Example 7 (FIGS. 10A and 10B) began with an initial solution of 20 mg/mL Protein 2 in 13 mM sodium phosphate and 146 mM sucrose at pH 7.3 (Wang W. (1999) Instability, stabilization, and formulation of liquid protein pharmaceuticals. International Journal of Pharmaceutics 185, 129-188.). UF1 concentrated the protein to more than 30 mg/mL. DF1, run against 500 mM sodium succinate at pH 5.7, then completely removed the phosphate. After DF2 against water and UF2, the product pool was 89 mg/mL Protein 2 with 4 mM succinate and a succinate/protein ratio below 10:1 (Note that under these pH conditions, succinate has a charge of −2.).

Succinate is associated with a strong increase of opalescence and aggregation (FIG. 10B): during the final UF2 concentration from 30 to 89 mg/mL, monomer content drops by approximately 2%. This indicates reduced protein stability at higher protein concentration for antibody-succinate formulations in the absence of sucrose (cf. Ross P. D. and Shrake A. (1988), Decrease in stability of human albumin with increase in protein concentration, Journal of Biological Chemistry 263, 11196-11202).

FIG. 10B also illustrates the good product quality with regard to the high degree of monomer content throughout the steps of the process.

Example 8

-Phosphate-Citrate Exchange-

According to example 8 an embodiment of the 4-step UF/DF process according to the present invention was applied to concentrate a protein and replace initial phosphate buffer ions with citrate.

The detailed conditions of example 8 were as follows:
UF1: 20 mg·ml$^{-1}$ Prot2/13 mM Phosphate/146 mM Sucrose/water/pH 7.3;
DF1: 4 cycles with 500 mM Citrate/water/pH 6.0;
DF2: 6 cycles with water;
UF2 (Product Pool): 64 mg·ml$^{-1}$ Prot2/1.5 mM Citrate/water/pH 7.0.

Figure 11:
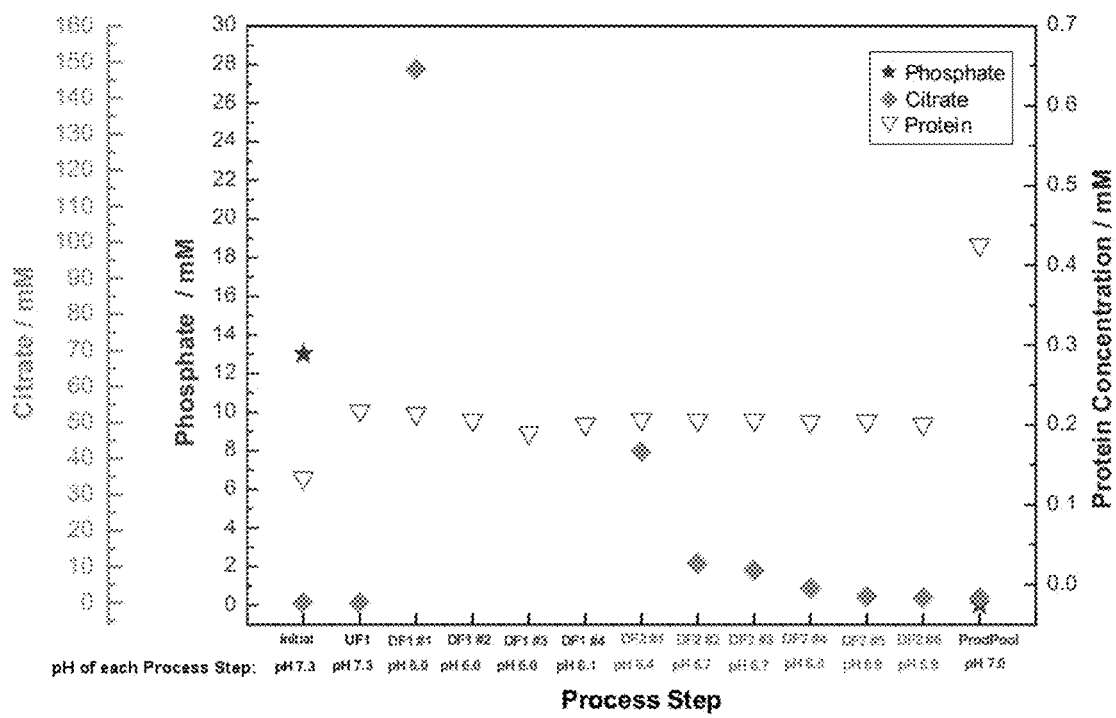
FIG. 11 a diagram of an exemplary embodiment of the ultrafiltration/diafiltration (UF/DF) process according to the present invention: the excipient and protein concentrations during the UF/DF-process of protein 2 (Prot2) (y axis) are plotted against the pH value in each process step (step (a) to step (d)) (x axis) in a phosphate-citrate exchange.

FIG. 11 shows the results of the phosphate-citrate exchange according to example 8. On the y axis the excipient and protein concentrations during the UF/DF-process of protein 2 (Prot2) are entered, the UF/DF-process including a diafiltration step with 4 cycles of 500 mM sodium citrate pH 6.0 (DF1) followed by 6 cycles of diafiltration with ultrapure water of type 1 (e.g. MilliQ® water of Merck Millipore) (pH 7) (DF2) to provide an entire exchange of the excipients from the initial solution towards the anion component (citrate) of DF1.

The x axis coordinates the process steps and the corresponding pH. The respective points on the x axis are: initial, end of UF1, cycle #1/#2/#3/#4 of DF1, cycle #1/#2/#3/#4/#5/#6 of DF2 and the final product (ProdPool) at the end of UF2.

Example 9

-Phosphate-Chloride Exchange-

According to example 9 an embodiment of the 4-step UF/DF process according to the present invention was applied to concentrate a protein and replace initial phosphate buffer ions with chloride.

The detailed conditions of example 9 were as follows:
UF1: 20 mg·ml$^{-1}$ Prot2/13 mM Phosphate/146 mM Sucrose/water/pH 7.3;
DF1: 4 cycles with 500 mM NaCl/water/pH 7.0;
DF2: 6 cycles with water;
UF2 (Product Pool): 87 mg·ml$^{-1}$ Prot2/3 mM Chloride/water/pH 7.0.

Figure 12:
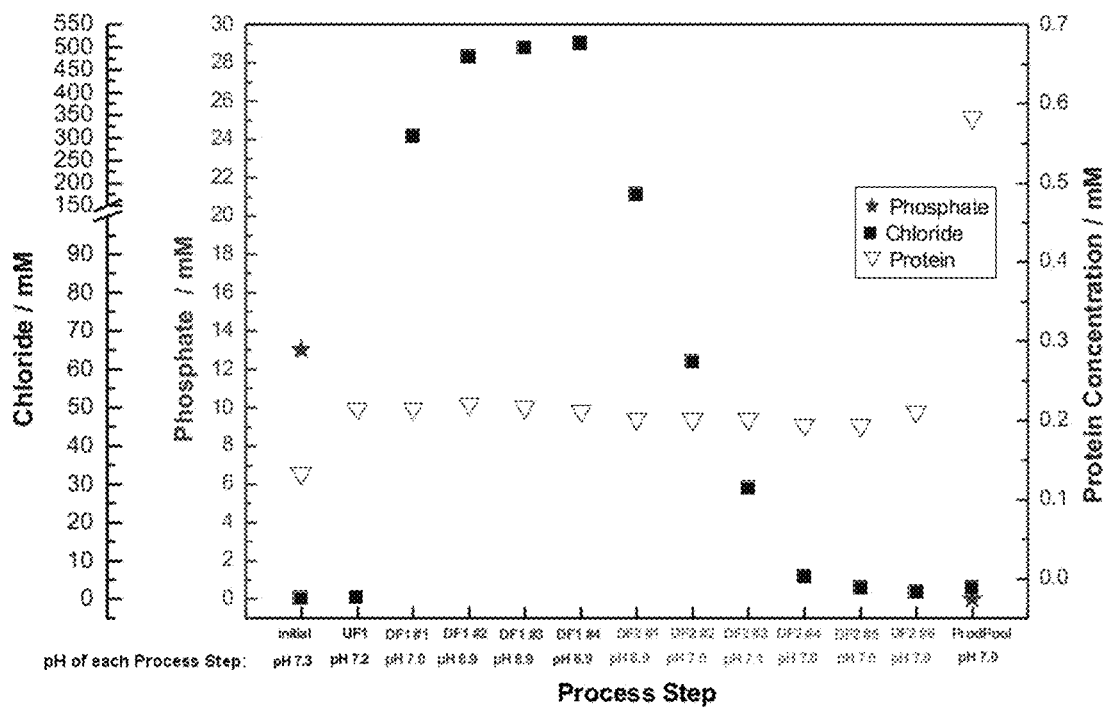
FIG. 12 a diagram of an exemplary embodiment of the ultrafiltration/diafiltration (UF/DF) process according to the present invention: the excipient and protein concentrations during the UF/DF-process of protein 2 (Prot2) (y axis) are plotted against the pH value in each process step (step (a) to step (d)) (x axis) in a phosphate-chloride exchange.

FIG. 12 shows the results of the phosphate-chloride exchange according to example 9. On the y axis the excipient and protein concentrations during the UF/DF-process of protein 2 (Prot2) are entered, the UF/DF-process including a diafiltration step with 4 cycles of 500 mM NaCl pH 7.0 (DF1) followed by 6 cycles of diafiltration with ultrapure water of type 1 (e.g. MilliQ® water of Merck Millipore) (pH 7) (DF2) to provide an entire exchange of the excipients from the initial solution towards the anion component (chloride) of DF1.

The x axis coordinates the process steps and the corresponding pH. The respective points on the x axis are: initial, end of UF1, cycle #1/#2/#3/#4 of DF1, cycle #1/#2/#3/#4/#5/#6 of DF2 and the final product (ProdPool) at the end of UF2.

Phosphate can be completely removed by exchange with either citrate or chloride (FIGS. 11 and 12). In example 8, the initial solution of Protein 2 and phosphate was diafiltered against citrate. Viscosity increased, throughput fell, and the concentration of the final product pool was just 64 mg/mL Protein 2. In example 9, in which initial phosphate solution was diafiltered against chloride in DF1, the final product pool reached a concentration of 87 mg/mL Protein 2. In general, it was observed that Protein 2 was less soluble than Protein 1 under similar conditions. Interestingly, the anion/protein ratio is below of 5:1.

Example 10

-Succinate-Chloride Exchange-

According to example 10 an embodiment of the 4-step UF/DF process according to the present invention was applied to concentrate a protein and replace initial succinate buffer ions with chloride.

The detailed conditions of example 10 were as follows:
UF1: 8 mg ml$^{-1}$ Prot3/25 mM Succinate/water/pH 4.4;
DF1: 8 cycles with 200 mM NaCl/water/pH 4.5;
DF2: 5 cycles with water;
UF2 (Product Pool): 125 mg ml$^{-1}$ Prot3/30 mM Chloride/water/pH 4.5.

Figure 13A:
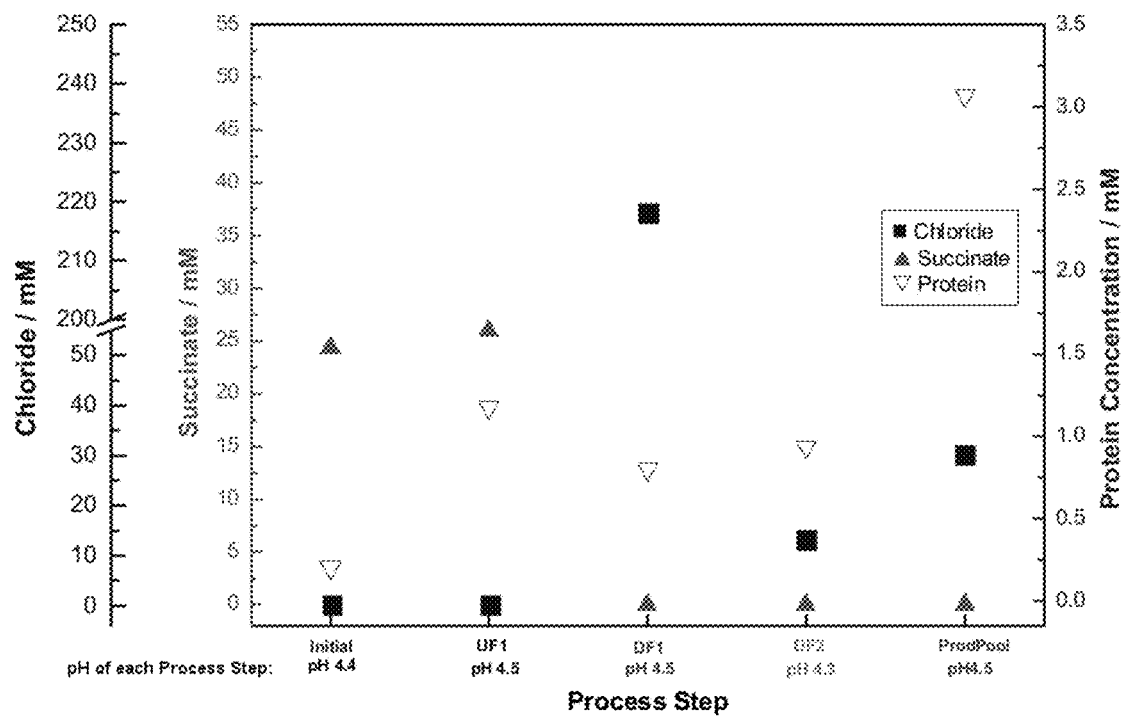
FIG. 13A a diagram of an exemplary embodiment of the ultrafiltration/diafiltration (UF/DF) process according to the present invention: the excipient and protein concentrations during the UF/DF-process of protein 2 (Prot2) (y axis) are plotted against the pH value in each process step (step (a) to step (d)) (x axis) in a succinate-chloride exchange.

FIG. 13A shows the results of the succinate-chloride exchange according to example 10. On the y axis the excipient and protein concentrations during the UF/DF-process of protein 3 (Prot3) are entered, the UF/DF-process including a diafiltration step with 8 cycles of 200 mM NaCl pH 4.5 (DF1) followed by 5 cycles of diafiltration with ultrapure water of type 1 (e.g. MilliQ® water of Merck Millipore) (pH 4.5) (DF2) to provide an entire exchange of the excipients from the initial solution towards the anion component (chloride) of DF1.

The x axis coordinates the process steps and the corresponding pH. The respective points on the x axis are: initial, end of UF1, end of DF1, end of DF2 and the final product (ProdPool) at the end of UF2.

Figure 13B:
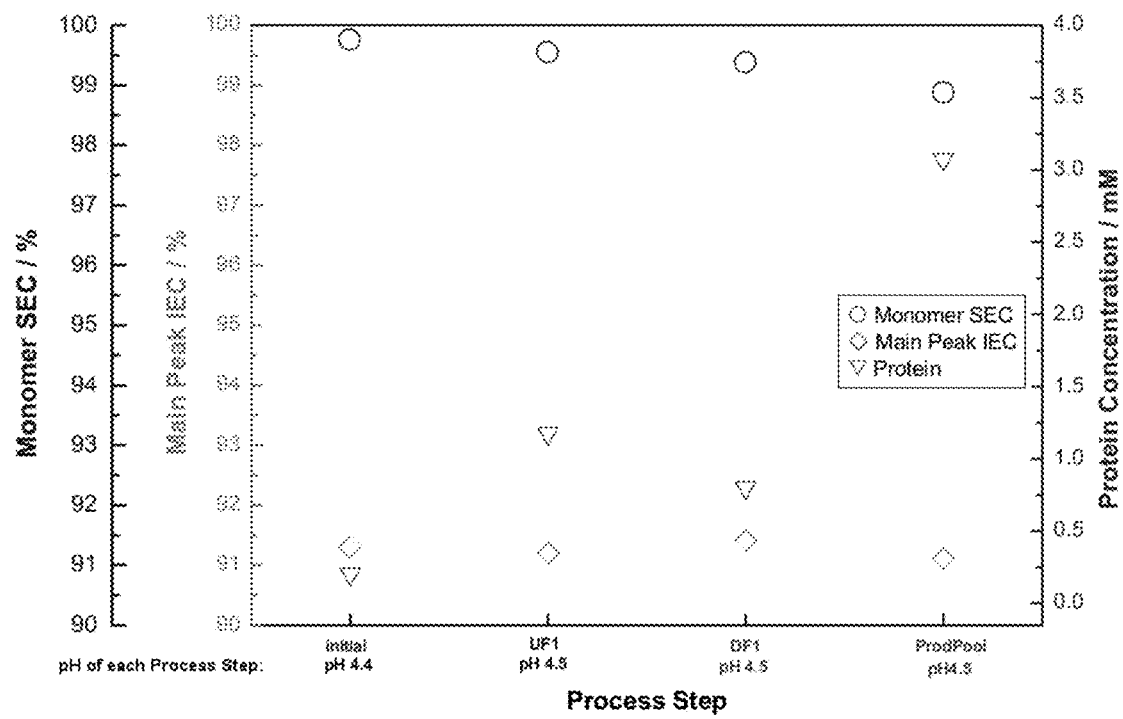
FIG. 13B a diagram wherein monomer content and IEC (ion-exchange chromatography) main peak during the UF/DF-process of protein 2 (Prot2) (y axis) of FIG. 10A are plotted against the pH value in each process step (step (a) to step (d)) (x axis) in a succinate-chloride exchange.

FIG. 13B shows the results of the monomer content and IEC main peak of the succinate-chloride exchange of example 10.

In example 10, it was tested the UF/DF process at the small scale, using Amicon ultra centrifugal filter units to condition and concentrate Protein 3, the nanobody. As example 10, it was assessed DF1 replacement of succinate with chloride (FIG. 13A). The initial protein solution is 8 mg/mL Protein 3 in 25 mM succinate under acidic conditions (pH 4.4).

The UF1 step increased concentration to more than 45 mg/mL Protein 3. Because Protein 3 showed solubility problems at high ionic strength, DF1 was run against 200 mM sodium chloride for 8 cycles; this was sufficient to fully remove succinate.

Five DF2 cycles against pure water reduced the chloride content to 13 mM. UF2 brought the concentration of the final product pool to 125 mg/mL Protein 3 in ~30 mM chloride, with a chloride/protein ratio between 10:1 and 14:1.

Under these process conditions the main peak of the ionic exchange peak is unchanged and the amount of aggregates as measured by high performance size exclusion chromatography (HP-SEC) is just reduced by 0.5%-0.8%, which is considered highly acceptable for a nanobody (FIG. 13B).

FIG. 5B also illustrates the good product quality with regard to the high degree of monomer content throughout the steps of the process.

Example 11

-Phosphate-Chloride Exchange-

According to example 11 an embodiment of the 4-step UF/DF process according to the present invention was applied to concentrate a protein and replace initial phosphate buffer ions with chloride.

The used biomolecule (designated as "Prot4" hereafter) was a Fc fusion protein.

The amino acid sequence of the FC fusion protein was as follows:

The sequence is listed as SEQ ID NO. 3 ("Artificial Sequence", "FC fusion protein") in the accompanying sequence listing.

The detailed conditions of example 11 were as follows:

UF1: 5 mg·ml$^{-1}$ Prot4/27 mM Phosphate/5 mM Chloride/water/pH 7.6;

DF1: 4 cycles with 500 mM NaCl/water/pH 7.0;

DF2: 8 cycles with water/0.002 wt % NaCl;

UF2 (Product Pool): 212 mg·ml$^{-1}$ Prot4/water/pH 7.2.

Figure 14:
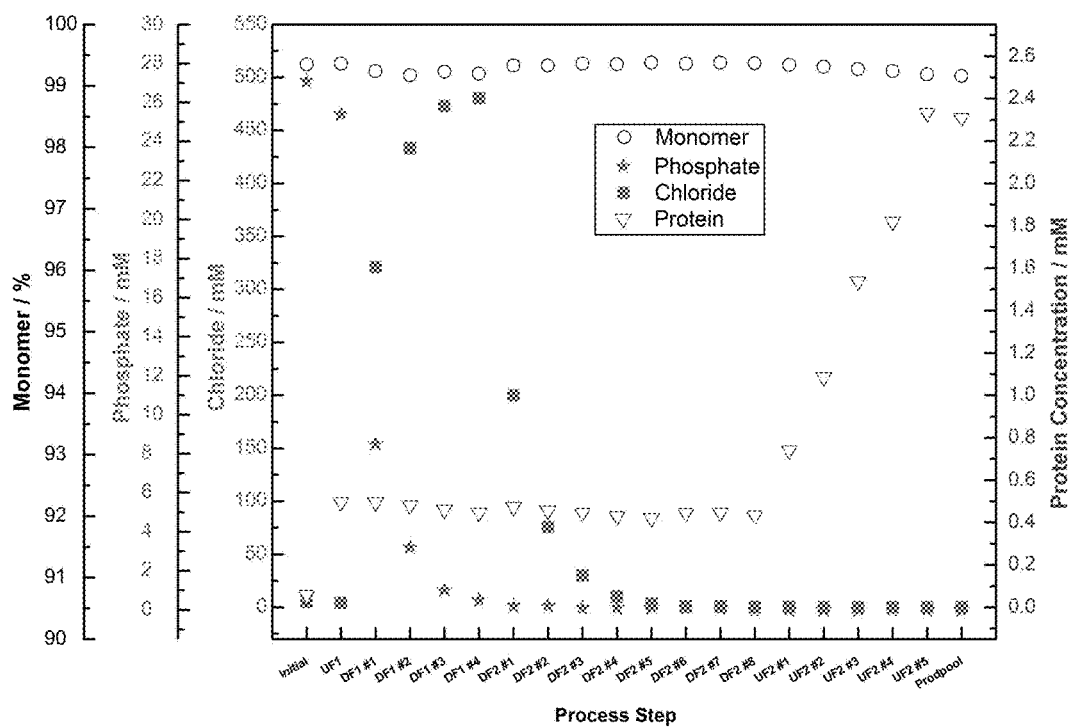
FIG. 14 a diagram of an exemplary embodiment of the ultrafiltration/diafiltration (UF/DF) process according to the present invention: the excipient and protein concentrations during the UF/DF-process of protein 4 (Prot4) (y axis) are indicated in each process step (step (a) to step (d)) (x axis) in a phosphate-chloride exchange.

FIG. 14 shows the results of the phosphate-chloride exchange according to example 11. On the y axis the monomer content, the excipient and protein concentrations during the UF/DF-process of protein 4 (Prot4) are entered, the UF/DF-process including a diafiltration step with 4 cycles of 500 mM NaCl pH 7.0 (DF1) followed by 8 cycles of diafiltration with ultrapure water of type 1 (e.g. MilliQ® water of Merck Millipore) including 0.002 wt % NaCl (pH 7) (DF2) to provide an entire exchange of the excipients from the initial solution towards the anion component (chloride) of DF1.

The x axis indicates the process steps. The respective points on the x axis are: initial, end of UF1, cycle #1/#2/#3/#4 of DF1, cycle #1/#2/#3/#4/#5/#6/#7/#8 of DF2, sampling point #1/#2/#3/#4/#5 of UF2 and the final product (ProdPool) at the end of UF2.

Phosphate can be completely removed by exchange with chloride at a final protein concentration in the product pool of 212 mg·ml$^{-1}$. From the initial solution at 5 mg·ml$^{-1}$ to the product pool at 212 mg·ml$^{-1}$ a total loss in monomer content of 0.2% could be observed which is considered highly acceptable for a fusion-protein (FIG. 14).

FIG. 14 also illustrates the good product quality with regard to the high degree of monomer content throughout the steps of the process.

Example 12

-Acetate/Succinate/Citrate-Chloride Exchange-

According to example 12 an embodiment of the 4-step UF/DF process according to the present invention was applied to concentrate a protein and replace initial acetate, succinate and citrate buffer ions with chloride.

The used biomolecule (designated as "Prot5" hereafter) had a sequence which was 100% identical to the published sequence of Rituximab comprising this heavy chain (amino acid single letter code, N to C-terminus):

```
  1 MGVLLTQRTL LSLVLALLFP SMASMAMHVA QPAVVLASSR GIASFVCEYA

51 SPGKATEVRV TVLRQADSQV TEVCAATYMM GNELTFLDDS ICTGTSSGNQ

101 VNLTIQGLRA MDTGLYICKV ELMYPPPYYL GIGNGTQIYV IDPEPCPDSD

151 QEPKSSDKTH TSPPSPAPEL LGGSSVFLFP PKPKDTLMIS RTPEVTCVVV

201 DVSHEDPEVK FNWYVDGVEV HNAKTKPREE QYNSTYRVVS VLTVLHQDWL

251 NGKEYKCKVS NKALPAPIEK TISKAKGQPR EPQVYTLPPS RDELTKNQVS

301 LTCLVKGFYP SDIAVEWESN GQPENNYKTT PPVLDSDGSF FLYSKLTVDK

351 SRWQQGNVFS CSVMHEALHN HYTQKSLSLS PGK
```

```
  1 QVQLQQPGAE LVKPGASVKM SCKASGYTFT SYNMHWVKQT PGRGLEWIGA

51 IYPGNGDTSY NQKFKGKATL TADKSSSTAY MQLSSLTSED SAVYYCARST

101 YYGGDWYFNV WGAGTTVTVS AASTKGPSVF PLAPSSKSTS GGTAALGCLV

151 KDYFPEPVTV SWNSGALTSG VHTFPAVLQS SGLYSLSSVV TVPSSSLGTQ

201 TYICNVNHKP SNTKVDKKAE PKSCDKTHTC PPCPAPELLG GPSVFLFPPK

251 PKDTLMISRT PEVTCVVVDV SHEDPEVKFN WYVDGVEVHN AKTKPREEQY

301 NSTYRVVSVL TVLHQDWLNG KEYKCKVSNK ALPAPIEKTI SKAKGQPREP

351 QVYTLPPSRD ELTKNQVSLT CLVKGFYPSD IAVEWESNGQ PENNYKTTPP

401 VLDSDGSFFL YSKLTVDKSR WQQGNVFSCS VMHEALHNHY TQKSLSLSPG

451 K
``` and this light chain (amino acid single letter code, N to C-terminus):

```
  1 QIVLSQSPAI LSASPGEKVT MTCRASSSVS YIHWFQQKPG SSPKPWIYAT

51 SNLASGVPVR FSGSGSGTSY SLTISRVEAE DAATYYCQQW TSNPPTFGGG

101 TKLEIKRTVA APSVFIFPPS DEQLKSGTAS VVCLLNNFYP REAKVQWKVD

151 NALQSGNSQE SVTEQDSKDS TYSLSSTLTL SKADYEKHKV YACEVTHQGL

201 SSPVTKSFNR GEC
```

The sequences are listed as SEQ ID NO. 4 ("Artificial Sequence", "Rituximab HC") and SEQ ID NO. 5 ("Artificial Sequence", "Rituximab LC") in the accompanying sequence listing.

The detailed conditions of example 12 were as follows:
UF1: 16 mg·ml$^{-1}$ Prot5/50 mM Acetate/53 mM Succinate/51 mM Citrate/water/pH 5.0;
DF1: 4 cycles with 500 mM NaCl/water/pH 7.0;
DF2: 8 cycles with water/0.002 wt % NaCl;
UF2 (Product Pool): 160 mg·ml$^{-1}$ Prot5/water/pH 4.9.

Figure 15:
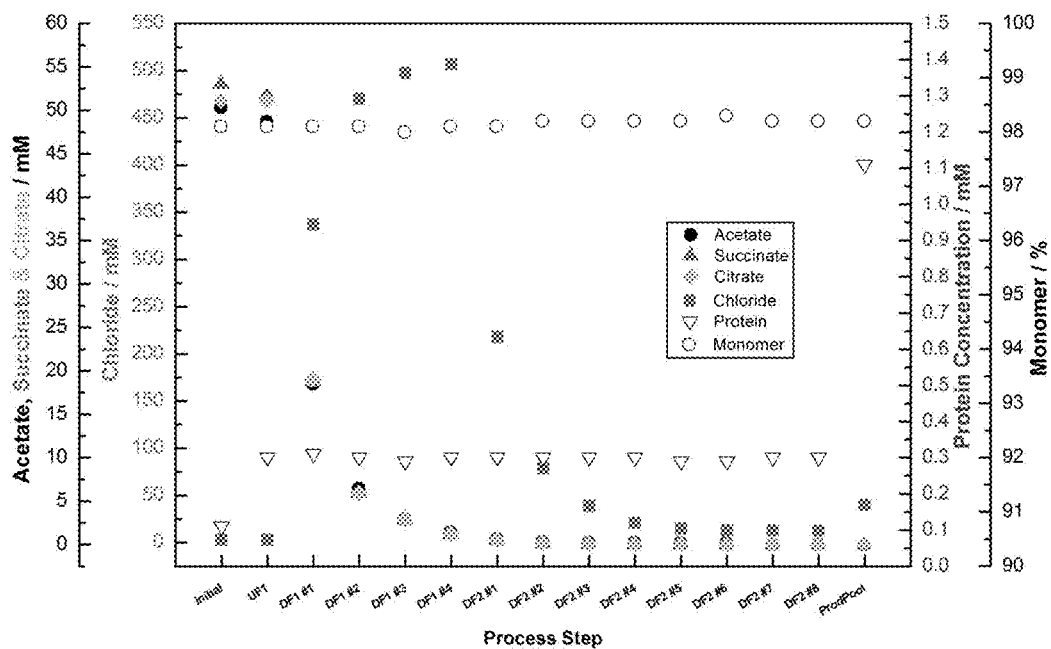
FIG. 15 a diagram of an exemplary embodiment of the ultrafiltration/diafiltration (UF/DF) process according to the present invention: the excipients and protein concentrations during the UF/DF-process of protein 5 (Prot5) (y axis) are indicated in each process step (step (a) to step (d)) (x axis) in an acetate/succinate/citrate-chloride exchange.

FIG. 15 shows the results of the acetate/succinate/citrate-chloride exchange according to example 12. On the y axis the excipient concentrations, the protein concentrations and the monomer content during the UF/DF-process of protein 5 (Prot5) are entered, the UF/DF-process including a diafiltration step with 4 cycles of 500 mM NaCl pH 7.0 (DF1) followed by 8 cycles of diafiltration with ultrapure water of type 1 (e.g. MilliQ® water of Merck Millipore) including 0.002 wt % NaCl (pH 7) (DF2) to provide an entire exchange of the excipients from the initial solution towards the anion component (chloride) of DF1.

The x axis indicates the process steps. The respective points on the x axis are: initial, end of UF1, cycle #1/#2/#3/#4 of DF1, cycle #1/#2/#3/#4/#5/#6/#7/#8 of DF2, and the final product (ProdPool) at the end of UF2.

The three carboxylic acids acetate, succinate and citrate can be completely removed by exchange with chloride. During the final concentration step (UF2) only the chloride ions get concentrated in the same way the protein was concentrated. The concentration of the anions acetate, succinate and citrate remains under the limit of quantification (LOQ). Due to the acid pH of 4.9 at the end of UF2 the amount of the counterions chloride showed a high level of 40 mM.

Under these process conditions the monomer content as measured by ultra-performance size exclusion chromatography (UP-SEC) is remaining at the initial percentage and did not change during the process.

FIG. 15 also illustrates the good product quality with regard to the high degree of monomer content throughout the steps of the process.

As a result, the presented examples show that the process according to the present invention can be used for antibodies as well as non-antibody formats. It allows to conditioning clearly defined formulations and by spiking additional excipients specific, well defined formulations can be generated.

Example 13

Robustness of the Process
-Exemplarily Demonstrated in an Acetate-Chloride Exchange- In order to determine whether the process according to the present invention represents a reliable method which leads to consistent results, the process was repeated 3 times to verify the robustness of the process. That is, at first, the process of the present invention including steps (a) to (d) comprising the order UF1/DF1/DF2/UF2 was performed and the resulting (first) biomolecule formulation investigated. Then, the same process using the same starting material and the same conditions was repeated and the resulting (second) biomolecule formulation investigated. Finally, the same process using the same starting material and the same conditions was again repeated and the resulting (third) biomolecule formulation investigated. A comparison of all three formulations show whether the results of the three biomolecule formulations obtained are the same or practically the same (within the tolerance possible) if the same starting materials and the same process conditions are used so that it can be concluded that the process is a trustworthy method.

Carrying Out the First Run

According to example 13 an embodiment of the 4-step UF/DF process according to the present invention was applied to concentrate a protein and replace initial acetate buffer ions with chloride. The same procedure as already described in example 6 was performed but the detailed conditions were selected to be as follows:

UF1: 10 mg ml$^{-1}$ Prot1/≈150 mM Acetate/≈170 mM NaCl/water/pH 5.9;
DF1: 4 cycles with 500 mM NaCl/water/pH 6;
DF2: 6 cycles with water/0.002 wt % NaCl.

In the last step (d) the product obtained was as follows:
UF2-1 (Product Pool): 198 mg ml$^{-1}$ Prot1/21 mM Chloride/water/pH 5.7.

It was found that the amount of acetate after UF2 was removed and being close to the LOQ of the assay.

Carrying Out the Second Run

The above 4-step UF/DF process was repeated with the same starting materials and the same conditions as before. In the last step (d) the product obtained was as follows:
UF2-2 (Product Pool): 195 mg ml$^{-1}$ Prot1/21 mM Chloride/water/pH 5.7.

It was found that the amount of acetate after UF2 was removed and being close to the LOQ of the assay.

Carrying Out the Third Run

The above 4-step UF/DF process was again repeated with the same starting materials and the same conditions as before. In the last step (d) the product obtained was as follows:
UF2-3 (Product Pool): 202 mg ml$^{-1}$ Prot1/20 mM Chloride/water/pH 5.7.

It was found that the amount of acetate after UF2 was removed and being close to the LOQ of the assay.

As a result, all 3 runs lead to the same or nearly the same results (within an acceptable tolerance) so that the process according to the present invention has been demonstrated to be a reliable process which provides consistent results.

The invention comprises aspects which are disclosed in the sentences below:

Sentences

1. A process for the preparation of a highly concentrated liquid formulation containing biomolecules comprising the steps of
   (a) a first ultrafiltration UF1;
   (b) a first diafiltration DF1;
   (c) a second diafiltration DF2; and
   (d) a second ultrafiltration UF2;
   whereby an aqueous solution of one or more salts as liquid medium B is used for step (b) and water or an aqueous solution of one or more salts as liquid medium C is used for step (c), whereby the salts used for step (b) are the same or different from the salts used for step (c), the liquid medium B has an ionic strength which is higher than the ionic strength of the liquid medium C.

2. The process according to sentence 1,
   characterized in that
   the liquid medium B has a high ionic strength indicated in form of a concentration which is in the range of from about 20 mM up to the limit of solubility of the salt, particularly preferred from about 100 mM to 1000 mM, more preferred about 150 mM to 750 mM, most preferred from about 200 mM to 500 mM
   and preferably
   the liquid medium C has a low ionic strength indicated in form of a concentration which is in the range of from about 0 mM to 150 mM, particularly preferred from about 0 mM to 100, more preferred about 0 mM to 75 mM, most preferred from about 0 mM to 50 mM.

3. The process according to sentence 1 or 2,
   characterized in that
   the liquid medium B has an ionic strength which is higher than the ionic strength of the liquid medium C so that the difference between the ionic strength of the liquid medium B and the ionic strength of the liquid medium C indicated in form of a concentration is at least about 100 mM, more preferred at least about 200 mM, most preferred at least about 500 mM.

4. The process according to any of the preceding sentences 1 to 3,
   characterized in that
   the liquid biomolecule formulation used in step (a) contains a liquid medium A which is an aqueous solution and contains one or more excipients, the liquid medium A is exchanged with liquid medium C by means of liquid medium B in steps (b) and (c), whereby the liquid biomolecule formulation obtained in step (c) and (d) has a reduced content of said excipient(s).

5. The process according to sentence 4,
   characterized in that
   the excipients are selected from a group consisting of excipients charged or neutral in aqueous solution;
   preferably the excipients being selected from the group consisting of additives used in the preparation or processing of biomolecules; unwanted substances or compounds such as impurities contained in the starting liquid biomolecule formulation; undesired side-products formed during the manufacturing process of the biomolecule; decomposition or degradation products of starting, intermediate or end products formed during the production of the biomolecule;
   particularly preferred cell components or debris, degradation products of bacteria such as endotoxines, DNA, RNA, undesired lipids, HCP (Host cell proteins), lipopolysaccharides (LPS) or parts thereof; sugars; detergents such as positively charged, negatively charged and also non-ionic species; any kind of negatively or positively charged ions, preferably resulting from salts.

6. The process according to any of the preceding sentences 1 to 5,
   characterized in that
   the salts are selected from organic salts and/or inorganic salts.

7. The process according to any of the preceding sentences 1 to 6,
   characterized in that
   the inorganic salt is selected from the group consisting of alkali salts or alkaline earth salts of sulfates, nitrates, phosphates, carbonates, halogenides, borates, silkates and the like
   or
   the inorganic salt is selected from the group of pharmaceutically acceptable inorganic salts, preferably sodium salts such as sodium halides, particularly preferred sodium chloride, sodium sulfate, sodium borate; calcium salts such as calcium halides, particularly preferred calcium chloride, calcium sulfate, calcium borate; magnesium salts such as magnesium halides, particularly preferred magnesium chloride, magnesium sulfate, magnesium borate, and combinations thereof, most preferred the inorganic salt is sodium chloride.

8. The process according to any of the preceding sentences 1 to 7,
characterized in that
liquid medium B comprises sodium chloride in a concentration from about 150 to about 900 mM, increasingly preferred from about 200 to about 700 mM, from about 400 to about 600 mM, and from about 450 to about 550 mM.

9. The process according to any of the preceding sentences 1 to 7,
characterized in that
the salt is an organic and/or inorganic buffer salt.

10. The process according to any of the preceding sentences 1 to 9,
characterized in that
the buffer salt is the basis of a buffer, preferably biological buffer, selected from the group consisting of N-(2-acetamido)-aminoethanesulfonic acid (ACES) and salts thereof, acetic acid and salts thereof, aconitic acid and salts thereof, adipic acid and salts thereof, ascorbic acid and salts thereof, N-(2-Acetamido)-iminodiacetic acid (ADA) and salts thereof, ammonia and salts thereof, ammonium chloride, 2-amino-2-methyl-1-propanol (AMP), 2-amino-2-methyl-1,3-propanediol, ammediol (AMPD), N-(1,1-Dimethyl-2-hydroxyethyl)-3-amino-2-hydroxypropanesulfonic acid (AMPSO) and salts thereof, N,N-bis-(2-hydroxyethyl)-2-aminoethanesulfonic acid (BES) and salts thereof, benzoic acid and salts thereof, bicarbonates such as sodium hydrogen carbonate, N,N'-bis(2-hydroxyethyl)-glycine (bicine), Tris buffers such as tris(hydroxymethyl)-aminomethane, [bis-(2-hydroxyethyl)-imino]-tris-(hydroxymethylmethane) (Bis-Tris), 1,3-bis[tris(hydroxymethyl)-methylamino]propane (Bis-Tris-Propane), boric acid and salts thereof, dimethylarsinic acid (Cacodylate) and salts thereof, 3-(cyclohexylamino)-propanesulfonic acid (CAPS) and salts thereof, 3-(cyclohexylamino)-2-hydroxy-1-propanesulfonic acid (CAPSO) and salts thereof, carbonic acid and salts thereof, carbonates such as sodium carbonate, cyclohexylaminoethanesulfonic acid (CHES) and salts thereof, citric acid and salts thereof, 3-[N-bis(hydroxyethyl)amino]-2-hydroxypropanesulfonic acid (DIPSO) and salts thereof, formic acid and salts thereof, gluconic acid and salts thereof, glyceric acid and salts thereof, glutamic acid and salts thereof, glycines such as glycylglycine, N-(2-hydroxyethyl)-piperazine-N'-ethanesulfonic acid (HEPES) and salts thereof, N-(2-hydroxyethyl)-piperazine-N'-3-propanesulfonic acid (HEPPS, EPPS) and salts thereof, N-(2-hydroxyethyl)-piperazine-N'-2-hydroxypropanesulfonic acid (HEPPSO) and salts thereof, imidazoles, lactic acid and salts thereof, malic acid and salt thereof, maleic acid and salts thereof, 2-(N-morpholino)-ethanesulfonic acid (MES) and salts thereof, 3-(N-morpholino)-propanesulfonic acid (MOPS) and salts thereof, 3-(N-morpholino)-2-hydroxypropanesulfonic acid (MOPSO) and salts thereof, phosphoric acid and salts thereof, piperazine-N,N'-bis(2-ethanesulfonic acid) (PIPES) and salts thereof, piperazine-N,N'-bis(2-hydroxypropanesulfonic acid) (POPSO) and salts thereof, pyridines, succinic acid and salts thereof, 3-{[tris(hydroxymethyl)-methyl]-amino}-propanesulfonic acid (TAPS) and salts thereof, 3-[N-tris(hydroxymethyl)-methylamino]-2-hydroxypropanesulfonic acid (TAPSO) and salts thereof, tartaric acid and salts thereof, taurine (2-aminoethanesulfonic acid, AES and salts thereof), triethanolamine (TEA), 2-[tris(hydroxymethyl)-methylamino]-ethanesulfonic acid (TES) and salts thereof, and N-[tris(hydroxymethyl)-methyl]-glycine (tricine);
or the biological buffer is an amino acid in an aqueous solution, the amino acid being selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine;
particularly preferred biological buffers are selected from the group consisting of phosphoric acid and salts thereof, citric acid and salts thereof, tris, succinic acid and salts thereof, malic acid and salts thereof, tartaric and salts thereof, acetic acid and salts thereof, lactic acid and salts thereof, aconitic acid and salts thereof, ascorbic acid and salts thereof, glutamic acid and salts thereof, ammoniumchloride, triethanolamine, alanine, arginine, glutamine, glycine, histidine, lysine, and proline.

11. The process according to any of the preceding sentences 1 to 10,
characterized in that
the liquid medium C consists or essentially consist of water.

12. The process according to any of the preceding sentences 1 to 11,
characterized in that
the biomolecule and the excipient(s) to be removed from the liquid biomolecule formulation have opposite charges,
preferably the biomolecule is positively charged and the excipient(s) to be removed by the process are negatively charged excipient(s),
most preferably the biomolecule is a positively charged protein and the negatively charged excipient(s) are anions.

13. The process according to any of the preceding sentences 1 to 12,
characterized in that
the process step (b) may be repeated several times prior to perform the subsequent step (c), preferably the exchange of liquid medium B may be performed with x medium cycles, whereby x=2 to 10, more preferably x=2 to 8, most preferably x=2 to 6.

14. The process according to any of the preceding sentences 1 to 13,
characterized in that
the process step (c) may be repeated several times prior to perform the subsequent step (d), preferably the exchange of liquid medium C may be performed with y medium cycles, whereby y=2 to 10, more preferably y=2 to 8, most preferably y=2 to 6.

15. The process according to any of the preceding sentences 1 to 14,
characterized in that
the ultrafiltration UF1 of step (a) is used to concentrate the liquid biomolecule formulation, preferably up to about 10%-70%, more preferably about 15%-60%, most preferably about 25%-50% compared with the initial concentration of the liquid biomolecule formulation.

16. The process according to any of the preceding sentences 1 to 15,
characterized in that
the ultrafiltration UF2 of step (d) is used to concentrate the liquid biomolecule formulation to the desired value.

17. The process according to any of the preceding sentences 1 to 16,
characterized in that
step (b) and step (c) follow directly one after the other whereby no intermediate process step is performed in between,
preferably also step (a) and step (b) follow directly one after the other whereby no intermediate process step is performed in between, and
preferably also step (c) and step (d) directly follow one after the other whereby no intermediate process step is performed in between.

18. The process according to any of the preceding sentences 1 to 17,
characterized in that
the biomolecules are selected from the group consisting of small molecules, preferably lipds such as phospholipids, glycolipids, sterols; vitamins; hormones; neurotransmitter;
Monomers, preferably amino acids, nucleotides, monosaccharides;
biopolymers, preferably proteins or peptides; nucleic acids such as DNA, RNA; oligosaccharides, polysaccharides such as glycogen, starch, chitin, cellulose, fructane, dextrane;
particularly preferred are proteins or peptides, nucleic acids, oligosaccharides, and polysaccharides;
most preferred are proteins or peptides.

19. The process according to any of the preceding sentences 1 to 18,
characterized in that
the process steps (a) to (d) are performed at room temperature (20-25° C.).

20. The process according to any of the preceding sentences 1 to 19,
characterized in that
the process steps (a) to (d) are performed using a tangential flow filtration (TFF) system or a centrifugal filtration system.

21. Highly concentrated liquid formulation containing biomolecules prepared by a process according to any of sentences 1 to 20.

The invention claimed is:

1. A process for the preparation of a concentrated liquid formulation containing biomolecules from a liquid biomolecule formulation comprising the steps of
    (a) a first ultrafiltration UF1;
    (b) a first diafiltration DF1;
    (c) a second diafiltration DF2; and
    (d) a second ultrafiltration UF2;
    wherein an aqueous solution of one or more salts, as liquid medium B, is used for step (b) and water or an aqueous solution of one or more salts, as liquid medium C, is used for step (c); wherein the one or more salts used for step (b) are the same or different from the one or more salts used for step (c), wherein the liquid medium B has an ionic strength which is higher than the ionic strength of the liquid medium C, and
    wherein the biomolecules comprise positively charged biomolecules and excipient(s) to be removed by the process comprise negatively charged excipient(s).

2. The process according to claim 1,
characterized in that
the liquid medium B has a high ionic strength in the range of from about 20 mM up to 6 M, or from about 100 mM to 1000 mM, or from about 150 mM to 750 mM, or from about 200 mM to 500 mM and
the liquid medium C has a low ionic strength indicated in form of a concentration which is in the range of from about 0 mM to 150 mM, or from about 0 mM to 100 mM, or from about 0 mM to 75 mM, or from about 0 mM to 50 mM.

3. The process according to claim 1,
characterized in that
the liquid medium B has an ionic strength which is higher than the ionic strength of the liquid medium C so that the difference between the ionic strength of the liquid medium B and the ionic strength of the liquid medium C is at least about 100 mM, or at least about 200 mM, or at least about 500 mM.

4. The process according to claim 1,
characterized in that
the liquid biomolecule formulation used in step (a) contains a liquid medium A which is an aqueous solution and contains one or more excipients, the liquid medium A is exchanged with liquid medium C by means of liquid medium B in steps (b) and (c), whereby the liquid biomolecule formulation obtained in step (c) and (d) has a reduced content of said excipient(s).

5. The process according to claim 4,
characterized in that
the excipients are selected from a group consisting of excipients charged in aqueous solution;
the excipients being selected from the group consisting of additives used in the preparation or processing of biomolecules; unwanted substances or ions such as impurities contained in the starting liquid biomolecule formulation; undesired side-products formed during the manufacturing process of the biomolecule; and decomposition or degradation products of starting, intermediate or end products formed during the production of the biomolecule.

6. The process according to claim 5,
characterized in that
the additives, unwanted substances or ions originate from cell components or debris, degradation products of bacteria such as endotoxins, DNA, RNA, undesired lipids, HCP (Host cell proteins), lipopolysaccharides (LPS) or parts thereof; sugars; detergents, negatively charged species; any kind of negatively charged ions resulting from salts.

7. The process according to claim 1,
characterized in that
the salts are inorganic salts.

8. The process according to claim 7,
characterized in that
the inorganic salt is selected from the group consisting of alkali salts and alkaline earth salts of sulfates, nitrates, phosphates, carbonates, halogenides, borates, and silicates.

9. The process according to claim 7,
characterized in that
the inorganic salt is a pharmaceutically acceptable salt and is selected from the group consisting of sodium salts; calcium salts; magnesium salts and combinations thereof.

10. The process according to claim 9,
characterized in that
the sodium salts comprise sodium halides, sodium sulfate, or sodium borate;
the calcium salts comprise calcium halides, calcium sulfate, or calcium borate;

the magnesium salts comprise magnesium halides, magnesium sulfate or magnesium borate.

11. The process according to claim 10,
characterized in that
the halides comprise chlorides.

12. The process according to claim 1,
characterized in that
liquid medium B comprises sodium chloride from about 150 to about 900 mM, or from about 200 to about 700 mM, or from about 400 to about 600 mM, or from about 450 to about 550 mM.

13. The process according to claim 1,
characterized in that
the salt comprises an organic and/or inorganic buffer.

14. The process according to claim 13,
characterized in that
the buffer is selected from the group consisting of N-(2-acetamido)-aminoethanesulfonic acid (ACES) and salts thereof, acetic acid and salts thereof, aconitic acid and salts thereof, adipic acid and salts thereof, ascorbic acid and salts thereof, N-(2-Acetamido)-iminodiacetic acid (ADA) and salts thereof, ammonia and salts thereof, ammonium chloride, 2-amino-2-methyl-1-propanol (AMP), 2-amino-2-methyl-1,3-propanediol, ammediol (AMPD), N-(1,1-Dimethyl-2-hydroxyethyl)-3-amino-2-hydroxypropanesulfonic acid (AMPSO) and salts thereof, N,N-bis-(2-hydroxyethyl)-2-aminoethanesulfonic acid (BES) and salts thereof, benzoic acid and salts thereof, bicarbonates such as sodium hydrogen carbonate, N,N'-bis(2-hydroxyethyl)-glycine (bicine), Tris buffers such as tris(hydroxymethyl)-aminomethane, [bis-(2-hydroxyethyl)-imino]-tris-(hydroxymethylmethane) (Bis-Tris), 1,3-bis[tris(hydroxymethyl)-methylamino]propane (Bis-Tris-Propane), boric acid and salts thereof, dimethylarsinic acid (Cacodylate) and salts thereof, 3-(cyclohexylamino)-propanesulfonic acid (CAPS) and salts thereof, 3-(cyclohexylamino)-2-hydroxy-1-propanesulfonic acid (CAPSO) and salts thereof, carbonic acid and salts thereof, carbonates such as sodium carbonate, cyclohexylaminoethanesulfonic acid (CHES) and salts thereof, citric acid and salts thereof, 3-[N-bis(hydroxyethyl)amino]-2-hydroxypropanesulfonic acid (DIPSO) and salts thereof, formic acid and salts thereof, gluconic acid and salts thereof, glyceric acid and salts thereof, glutamic acid and salts thereof, glycines such as glycylglycine, N-(2-hydroxyethyl)-piperazine-N'-ethanesulfonic acid (HEPES) and salts thereof, N-(2-hydroxyethyl)-piperazine-N'-3-propanesulfonic acid (HEPPS, EPPS) and salts thereof, N-(2-hydroxyethyl)-piperazine-N'-2-hydroxypropanesulfonic acid (HEPPSO) and salts thereof, imidazoles, lactic acid and salts thereof, malic acid and salt thereof, maleic acid and salts thereof, 2-(N-morpholino)-ethanesulfonic acid (MES) and salts thereof, 3-(N-morpholino)-propanesulfonic acid (MOPS) and salts thereof, 3-(N-morpholino)-2-hydroxypropanesulfonic acid (MOPSO) and salts thereof, phosphoric acid and salts thereof, piperazine-N,N'-bis(2-ethanesulfonic acid) (PIPES) and salts thereof, piperazine-N,N'-bis(2-hydroxypropanesulfonic acid) (POPSO) and salts thereof, pyridines, succinic acid and salts thereof, 3-{[tris(hydroxymethyl)-methyl]-amino}-propanesulfonic acid (TAPS) and salts thereof, 3-[N-tris(hydroxymethyl)-methylamino]-2-hydroxypropanesulfonic acid (TAPSO) and salts thereof, tartaric acid and salts thereof, taurine (2-aminoethanesulfonic acid, AES and salts thereof), triethanolamine (TEA), 2-[tris(hydroxymethyl)-methylamino]-ethanesulfonic acid (TES) and salts thereof, and N-[tris(hydroxymethyl)-methyl]-glycine (tricine).

15. The process according to claim 13,
characterized in that
the buffer salt or the buffer being a biological buffer which is an amino acid, in an aqueous solution, selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine;
or the buffer salt or the buffer being a biological buffer which is selected from the group consisting of phosphoric acid and salts thereof, citric acid and salts thereof, tris, succinic acid and salts thereof, malic acid and salts thereof, tartaric and salts thereof, acetic acid and salts thereof, lactic acid and salts thereof, aconitic acid and salts thereof, ascorbic acid and salts thereof, glutamic acid and salts thereof, ammoniumchloride, triethanolamine, alanine, arginine, glutamine, glycine, histidine, lysine, and proline.

16. The process according to claim 1,
characterized in that
the liquid medium C consists essentially of water.

17. The process according to claim 1,
characterized in that
the biomolecules comprise a positively charged protein.

18. The process according to claim 1,
characterized in that
the process step (b) is repeated several times prior to step (c), or the exchange of liquid medium B is performed with x medium cycles, wherein x=2 to 10, or x=2 to 8, or x=2 to 6.

19. The process according to claim 1,
characterized in that
the process step (c) is repeated several times prior to step (d), or the exchange of liquid medium C is performed with y medium cycles, wherein y=2 to 10, or y=2 to 8, or y=2 to 6.

20. The process according to claim 1,
characterized in that
the ultrafiltration UF1 of step (a) is used to concentrate the liquid biomolecule formulation, up to about 10%-70%, or about 15%-60%, or about 25%-50% compared with the initial concentration of the liquid biomolecule formulation.

21. The process according to claim 1,
characterized in that
the ultrafiltration UF2 of step (d) is used to concentrate the liquid biomolecule formulation to the desired value.

22. The process according to claim 1,
characterized in that
step (b) and step (c) follow directly one after the other whereby no intermediate process step is performed in between, and/or step (a) and step (b) follow directly one after the other whereby no intermediate process step is performed in between, and/or step (c) and step (d) directly follow one after the other whereby no intermediate process step is performed in between.

23. The process according to claim 1,
characterized in that
the biomolecules are selected from the group consisting of small molecules, monomers, biopolymers; lipids, vitamins; hormones, neurotransmitter; amino acids, proteins, and peptides.

24. The process according to claim 1,
characterized in that
the process steps (a) to (d) are performed at room temperature of about 20° C. to about 25° C.

25. The process according to claim 1,
characterized in that
the process steps (a) to (d) are performed using a tangential flow filtration (TFF) system or a centrifugal filtration system.

26. A concentrated liquid formulation containing biomolecules prepared by a process according to claim 1.

27. The process according to claim 1,
characterized in that
the salts are organic salts.

* * * * *

UNITED STATES PATENT AND TRADEMARK OFFICE
CERTIFICATE OF CORRECTION

PATENT NO. : 11,572,385 B2
APPLICATION NO. : 16/325763
DATED : February 7, 2023
INVENTOR(S) : Patrick Garidel et al.

It is certified that error appears in the above-identified patent and that said Letters Patent is hereby corrected as shown below:

In the Specification

Figure 1A:
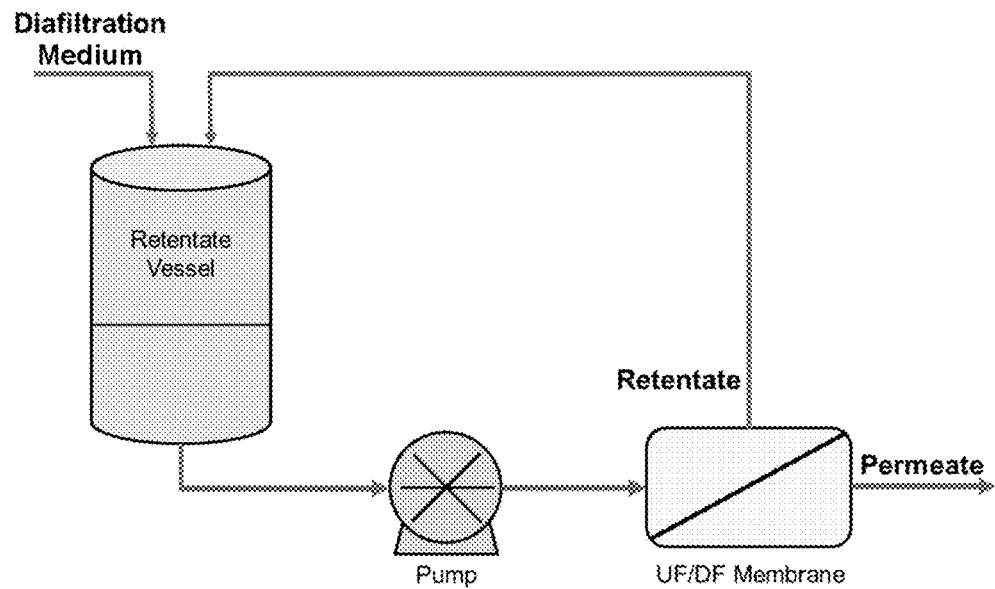
Figure 1B:
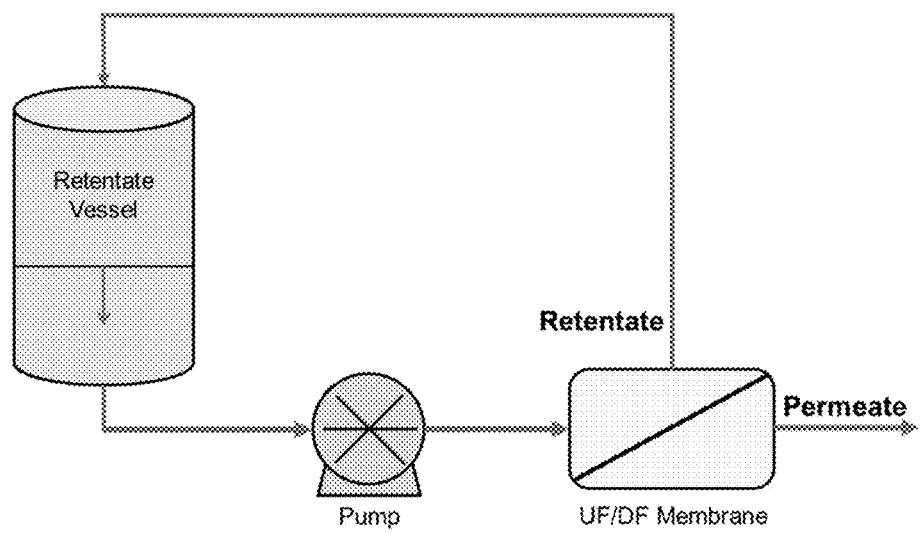
FIG. 1B a schematic representation of an ultrafiltration (UF) step.
Figure 2:
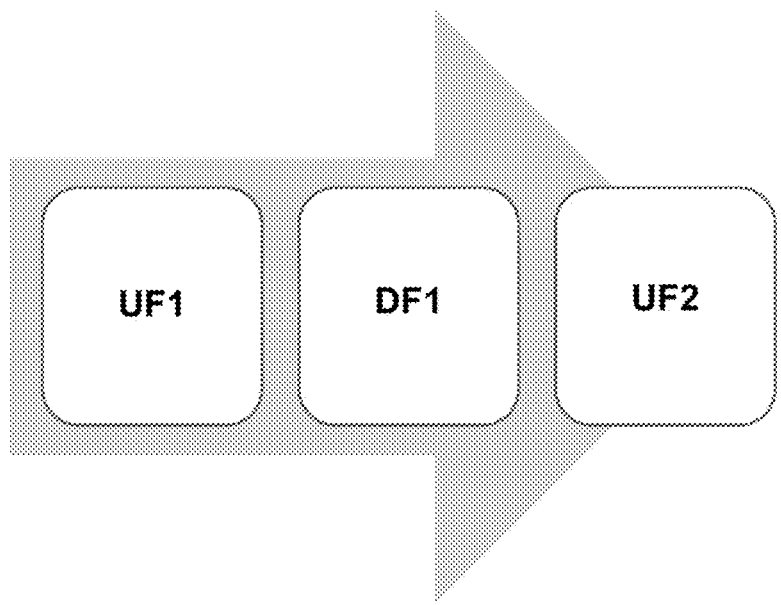
FIG. 2 a schematic representation of an ultrafiltration/diafiltration (UF/DF) process according to prior art.
Figure 3:
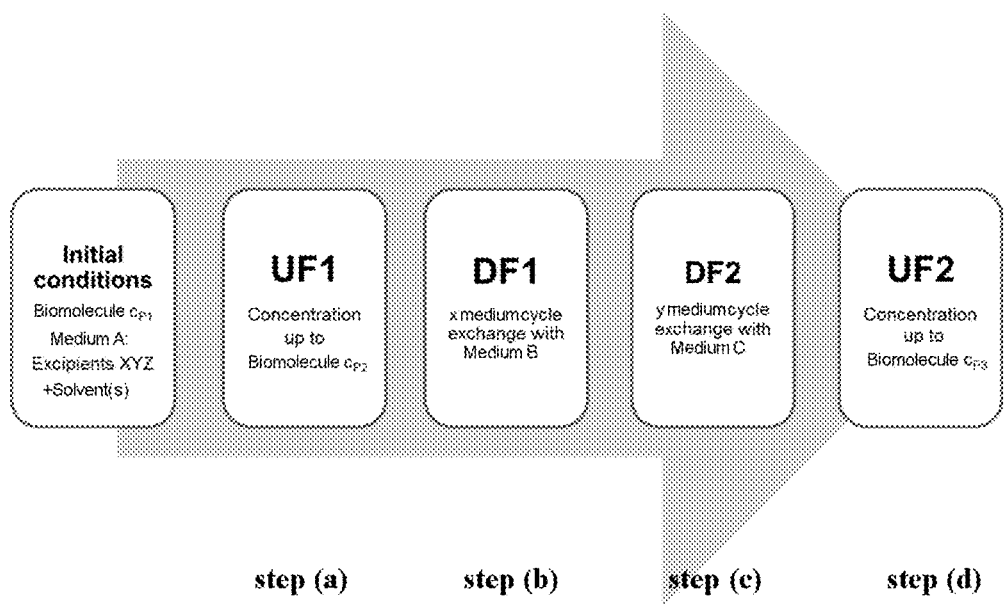
FIG. 3 a schematic representation of an exemplary embodiment of the ultrafiltration/diafiltration (UF/DF) process according to the present invention.

At Column 25, Line 22, replace "FIG. 2A" with --FIG. 1A--
At Column 25, Line 46, replace "FIG. 2A" with --FIG. 1A--

Signed and Sealed this
Tenth Day of September, 2024

Katherine Kelly Vidal
*Director of the United States Patent and Trademark Office*